(12) United States Patent
Iwazawa et al.

(10) Patent No.: US 9,211,266 B2
(45) Date of Patent: Dec. 15, 2015

(54) CELL CONSTRUCT FOR CELL TRANSPLANTATION AND CELL AGGREGATE FOR CELL TRANSPLANTATION

(75) Inventors: Reiko Iwazawa, Ashigarakami-gun (JP); Kentaro Nakamura, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 13/599,597

(22) Filed: Aug. 30, 2012

(65) Prior Publication Data
US 2013/0071441 A1 Mar. 21, 2013

(30) Foreign Application Priority Data

| Aug. 31, 2011 | (JP) | 2011-188596 |
| Apr. 16, 2012 | (JP) | 2012-092928 |
| Jun. 8, 2012 | (JP) | 2012-130582 |
| Jul. 31, 2012 | (JP) | 2012-169449 |

(51) Int. Cl.
| A61L 27/14 | (2006.01) |
| A61K 9/70 | (2006.01) |
| A61L 27/22 | (2006.01) |
| A61L 27/38 | (2006.01) |
| A61L 27/54 | (2006.01) |
| C07K 14/78 | (2006.01) |

(52) U.S. Cl.
CPC .............. *A61K 9/7007* (2013.01); *A61L 27/14* (2013.01); *A61L 27/227* (2013.01); *A61L 27/38* (2013.01); *A61L 27/3808* (2013.01); *A61L 27/54* (2013.01); *C07K 14/78* (2013.01); *A61L 2300/252* (2013.01); *A61L 2300/40* (2013.01); *A61L 2300/80* (2013.01); *A61L 2400/06* (2013.01)

(58) Field of Classification Search
None
See application file for complete search history.

(56) References Cited

U.S. PATENT DOCUMENTS

| 4,642,117 | A | * | 2/1987 | Nguyen et al. | 623/23.72 |
| 4,791,067 | A | * | 12/1988 | Sheiman et al. | 436/513 |
| 8,198,086 | B2 | | 6/2012 | Koga et al. | |
| 2006/0088569 | A1 | | 4/2006 | Kawata et al. | |
| 2008/0131473 | A1 | * | 6/2008 | Brown et al. | 424/423 |
| 2008/0220521 | A1 | | 9/2008 | Kawata et al. | |
| 2009/0228027 | A1 | | 9/2009 | Yamanaka et al. | |
| 2010/0158982 | A1 | | 6/2010 | Kawata et al. | |
| 2011/0200559 | A1 | | 8/2011 | Koga et al. | |
| 2012/0329157 | A1 | * | 12/2012 | Nakamura | 435/397 |
| 2013/0004549 | A1 | * | 1/2013 | Nakamura et al. | 424/400 |
| 2013/0084638 | A1 | * | 4/2013 | Iwazawa et al. | 435/375 |

FOREIGN PATENT DOCUMENTS

| JP | 2003-275294 A | 9/2003 |
| JP | 2004-267562 A | 9/2004 |
| JP | 2006-116212 A | 5/2006 |
| JP | 2009-112233 A | 5/2009 |
| JP | 2009-520501 A | 5/2009 |
| JP | 2009-240766 A | 10/2009 |
| WO | 03/051283 A2 | 6/2003 |
| WO | 2007/070660 A2 | 6/2007 |
| WO | 2007/073190 A1 | 6/2007 |
| WO | 2008/103041 A1 | 8/2008 |
| WO | 2008/123614 A1 | 10/2008 |
| WO | 2009/066468 A1 | 5/2009 |
| WO | WO 2010003104 A2 * | 1/2010 |
| WO | WO 2010147109 A1 * | 12/2010 |
| WO | 2011/108517 A1 | 9/2011 |

OTHER PUBLICATIONS

Machine translation of WO2010147109.*
Singh, Bhagirath et al; "Minimum peptide sequences necessary for priming and triggering of humoral and cell mediated immune responses in mice: use of synthetic peptide antigens of defined structure." J. Immun. (1980) 124(3) pp. 1336-1343.*
Asahara, Takayuki et al; "Isolation of putative prgenitor endothelial cells for angiogenesis." Science (1997) 275 pp. 964-967.*
Carmeliet, Peter; "Mechanims of angiogenesis and arteriogenesis." Nature Med. (2000) 6(3) pp. 389-395.*
Machine translation of WO 2010147109.*
Masami Harimoto et al., "Novel approach for achieving double-layered cell sheets co-cultures: overlaying endothelial cell sheets onto monolayer hepatocytes utilizing temperature-responsive culture dishes", J. Biomed. Mater. Res., 2002, 62: 464-470.
Ai Kushida et al., "Decrease in culture temperature releases monolayer endothelial cell sheets together with deposited fibronectin matrix from temperature-responsive culture surfaces", J. Biomed. Mater. Res., 1999, 45: 355-362.
Ai Kushida et al., "Temperature-responsive culture dishes allow nonenzymatic harvest of differentiated Madin-Darby canine kidney", J. Biomed. Mater. Res., 2000, 51: 216-223.
Teruo Okano, "Fusion of Inflammation and Regeneration Researches", Inflammation and Regeneration Editorial, 2005, 25(3): 158-159.

(Continued)

*Primary Examiner* — Maury Audet
*Assistant Examiner* — Fred Reynolds
(74) *Attorney, Agent, or Firm* — Sughrue Mion, PLLC

(57) ABSTRACT

An object of the present invention is to provide a cell construct for cell transplantation capable of having a thickness suitable for cell transplantation, preventing the necrosis of transplanted cells, and forming blood vessels in the transplantation site after transplantation. The present invention provides a cell construct for cell transplantation which comprises polymer blocks having biocompatibility and cells of at least one type, wherein the plural polymer blocks are arranged in spaces between the plural cells.

12 Claims, 37 Drawing Sheets
(20 of 37 Drawing Sheet(s) Filed in Color)

(56) References Cited

OTHER PUBLICATIONS

Tatsuya Shimizu, M.D. et al., "Two-Dimensional Manipulation of Cardiac Myocyte Sheets Utilizing Temperature-Responsive Culture Dishes Augments the Pulsatile Amplitude", Tissue Engineering, 2001, 7(2): 141-151.

Tatsuya Shimizu et al., "Electrically communicating three-dimensional cardiac tissue mimic fabricated by layered cultured cardiomyocyte sheets", J. Biomed. Mater. Res., 2002, 60: 110-117.

Tatsuya Shimizu et al., "Fabrication of Pulsatile Cardiac Tissue Grafts Using a Novel 3-Dimensional Cell Sheet Manipulation Technique and Temperature-Responsive Cell Culture Surfaces", Circ. Res., 2002, 90:e40-e48.

Tatsuya Shimizu et al., "Cell sheet engineering for myocardial tissue reconstruction", Biomaterials, 2003, 24: 2309-2316.

Jason Yang et al., "Sustained growth and three-dimensional organization of primary mammary tumor epithelial cells embedded in collagen gels", PNAS, 1979, 76(7): 3401-3405.

Extended Search Report issued in corresponding European Patent Application No. 12182571.5 on Oct. 25, 2012.

Andreina Parisi-Amon et al., "Using Peptide Hetero-Assembly to Trigger Physical Gelation and Cell Encapsulation", Mater. Res. Soc. Symp. Proc., 2010, vol. 1272, 6 pages.

Office Action, dated Jun. 30, 2014, issued in counterpart European Patent Application No. 12182571.5.

Communication from the Japanese Patent Office issued Jan. 6, 2015 in counterpart Japanese Patent Application No. 2012-169449.

Lao, Lihong, et al., "Colloids and Surfaces B: Biointerfaces," 2008, vol. 66, pp. 218-225.

Wu, Ying-Nan, et al., "Cartilaginous ECM Component-Modification of the Micro-Bead Culture System for Chondrogenic Differentiation of Mesenchymal Stem Cells," Biomaterials, 2007, vol. 28, pp. 4056-4067.

Chung, Hyun Jung, et al., "Injectable Cellular Aggregates Prepared from Biodegradable Porous Microspheres for Adipose Tissue Engineering," Tissue Engineering, 2009, vol. 15, No. 5 pp. 1391-1400.

\* cited by examiner

Figure 1    Stereoscopic microscope photograph of Day 7 (chondrogenic differentiation medium) of a mosaic cell mass prepared using recombinant gelatin micro-blocks.
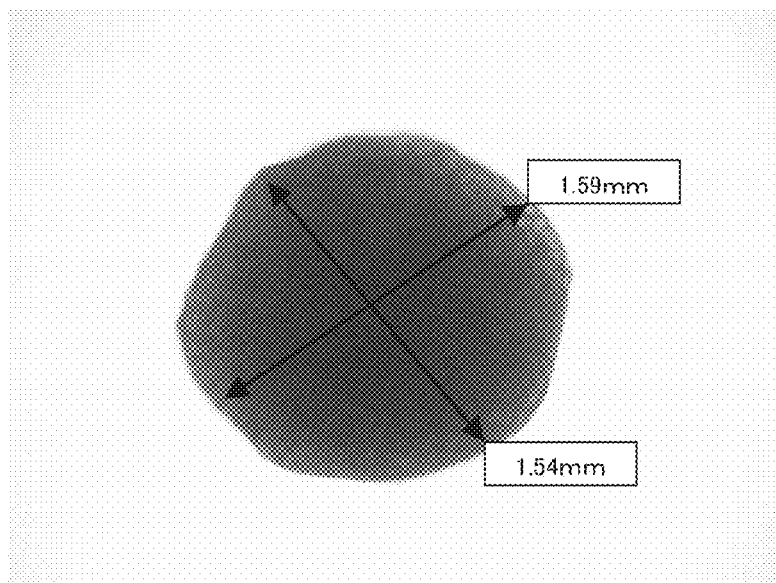
Figure 2    Stereoscopic microscope photograph of Day 7 (chondrogenic differentiation medium) of a mosaic cell mass prepared using natural gelatin micro-blocks
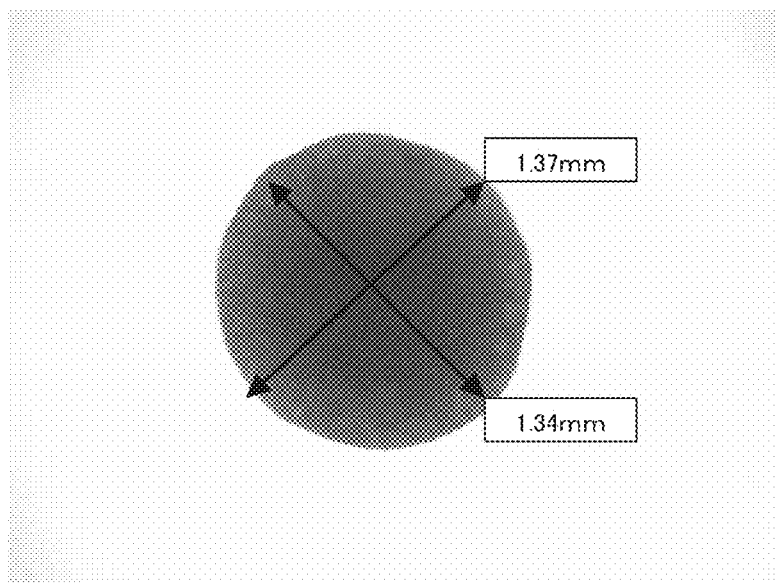

Figure 3  Photograph of a slice (HE-stained, magnification: ×5) of the mosaic cell mass containing the recombinant gelatin micro-blocks
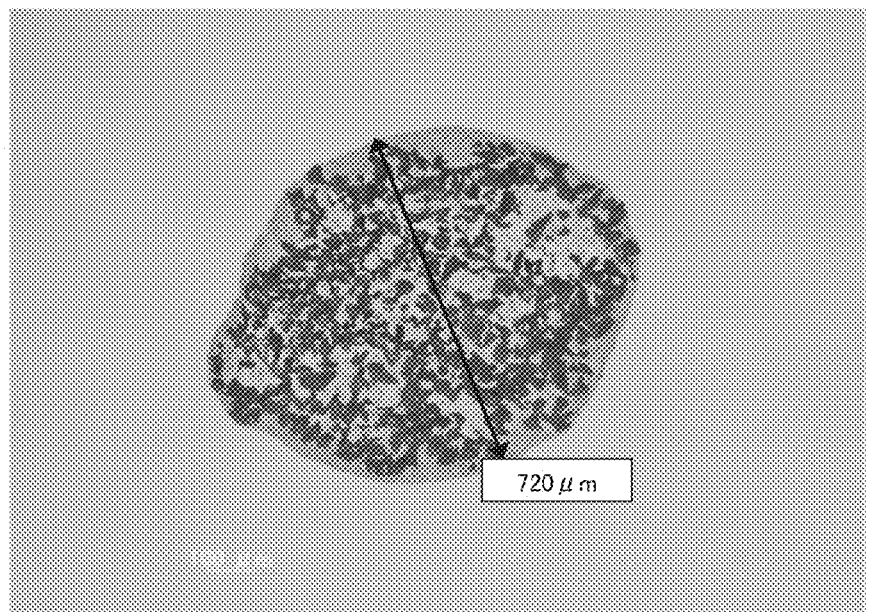
Figure 4  Photograph of a slice (HE-stained, magnification: ×10) of the mosaic cell mass containing the recombinant gelatin micro-blocks
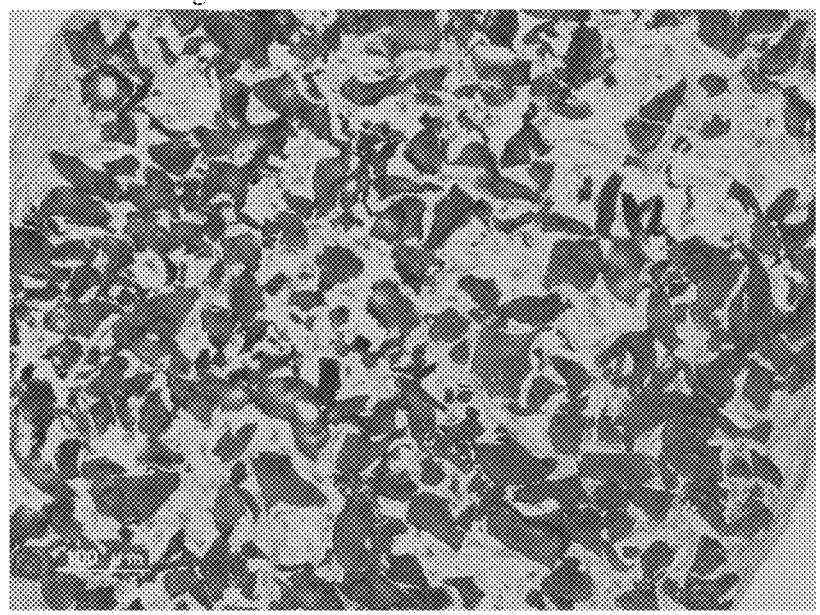

Figure 5  Photograph of a slice (HE-stained, magnification: ×40) of the mosaic cell mass containing the recombinant gelatin micro-blocks
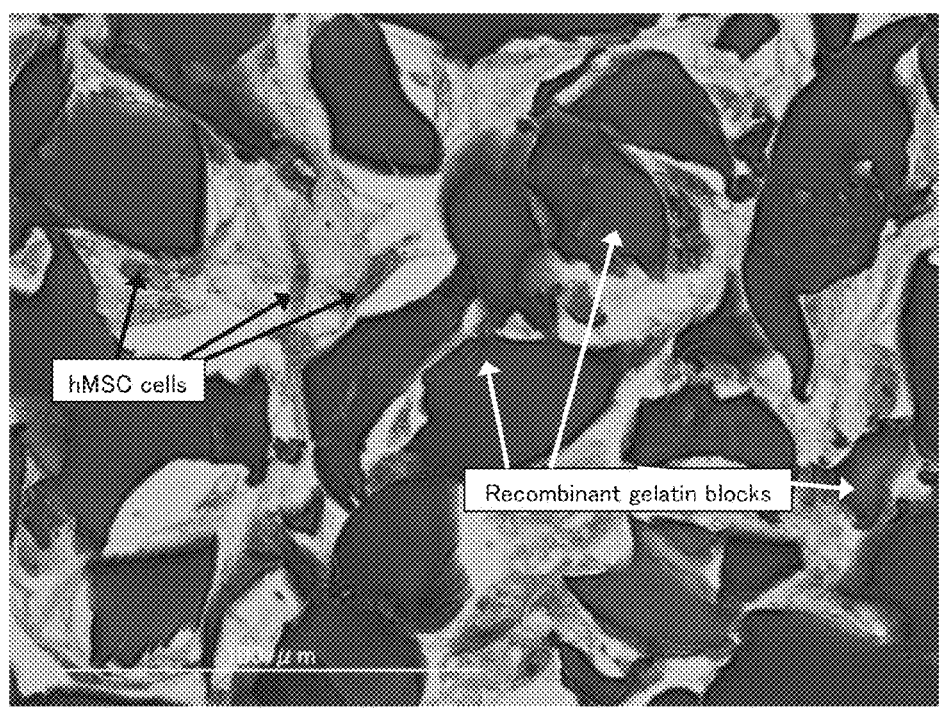

Figure 6  Fusion of the mosaic cell masses
Day 6 (first day of fusion)
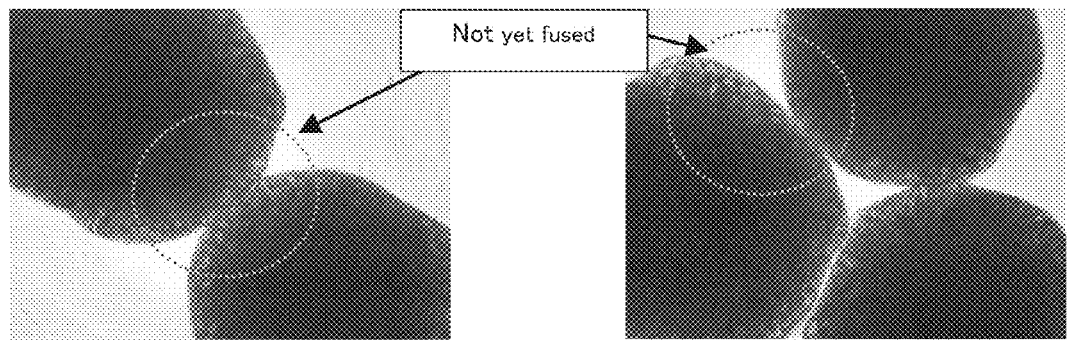
Day 11 (fifth day from the fusion)
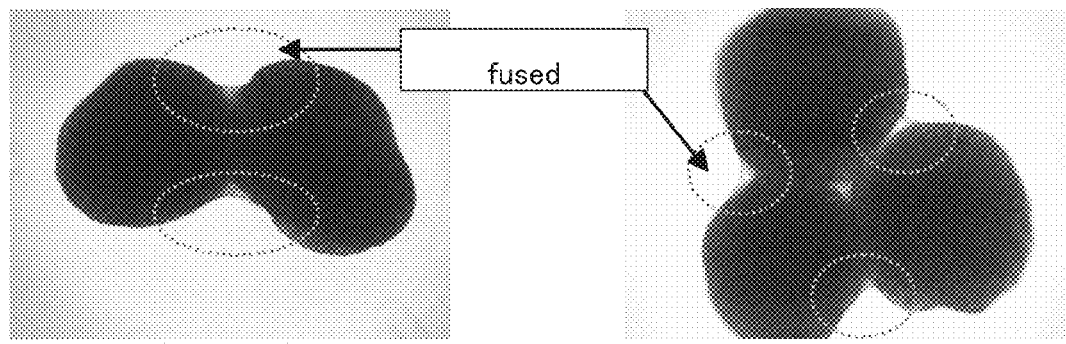
Magnified photograph at Day 11 (fifth day from the fusion)
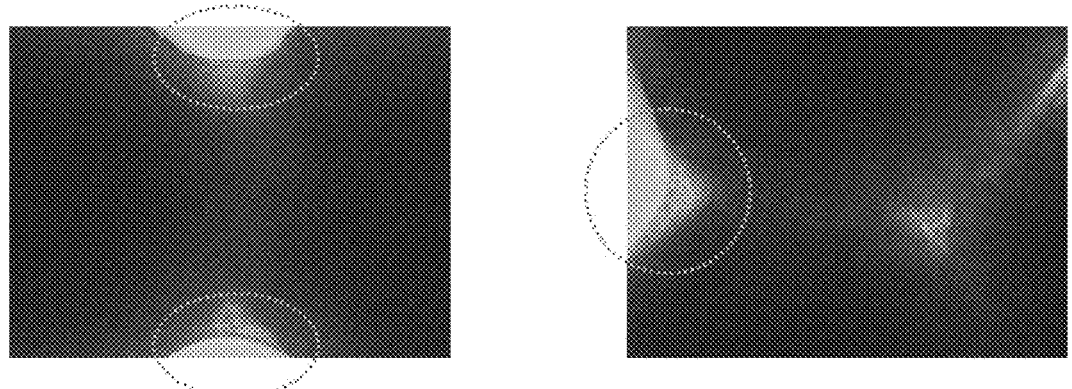

Figure 7  Photograph of a HE-stained slice (magnification: ×5) from the fusion of the mosaic cell masses (fusion of three mosaic cell masses)
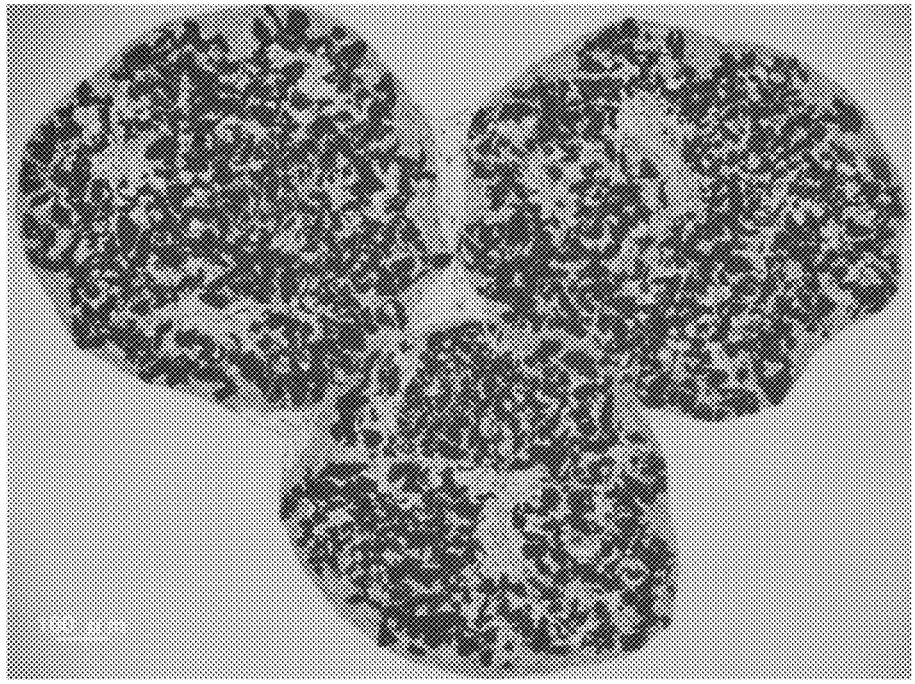
Figure 8  Photograph of a HE-stained slice (magnification: ×10) from the fusion of the mosaic cell masses (fusion of three mosaic cell masses)
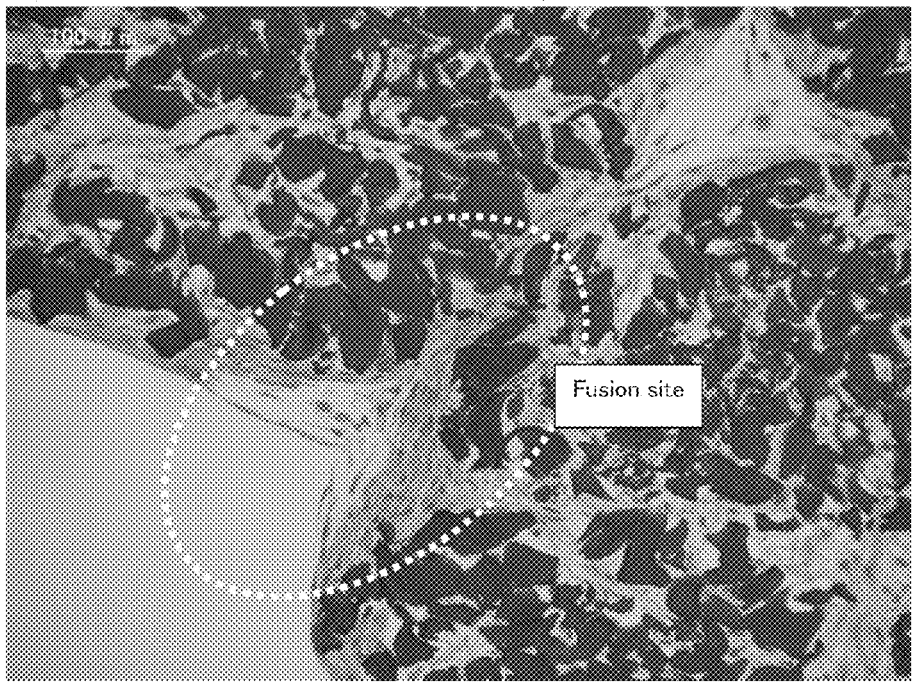

Figure 9   Photograph of a HE-stained slice (magnification: ×20) from the fusion of the mosaic cell masses (fusion of three mosaic cell masses)
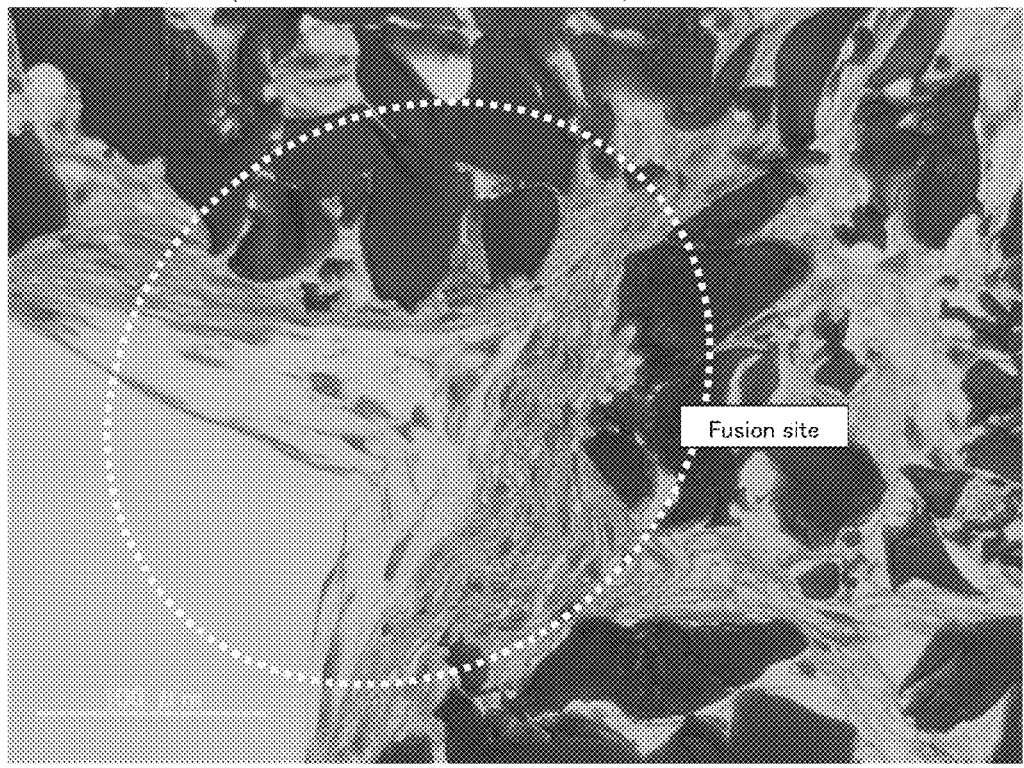

Figure 10  Photograph of a HE-stained slice (magnification: ×5) from the fusion of the mosaic cell masses (fusion of three mosaic cell masses)
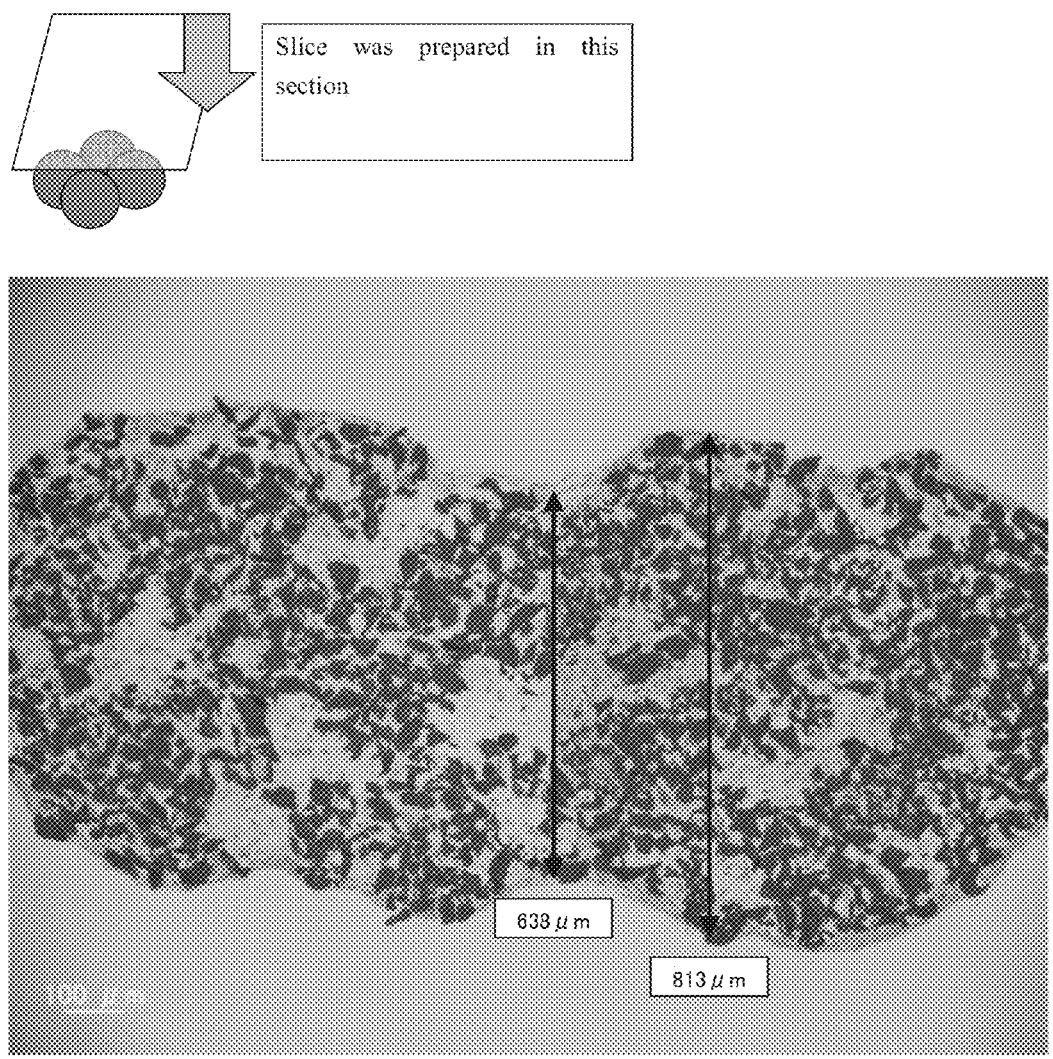

Figure 11  Photograph of a HE-stained slice (magnification: ×10) from the fusion of the mosaic cell masses (fusion of three mosaic cell masses)
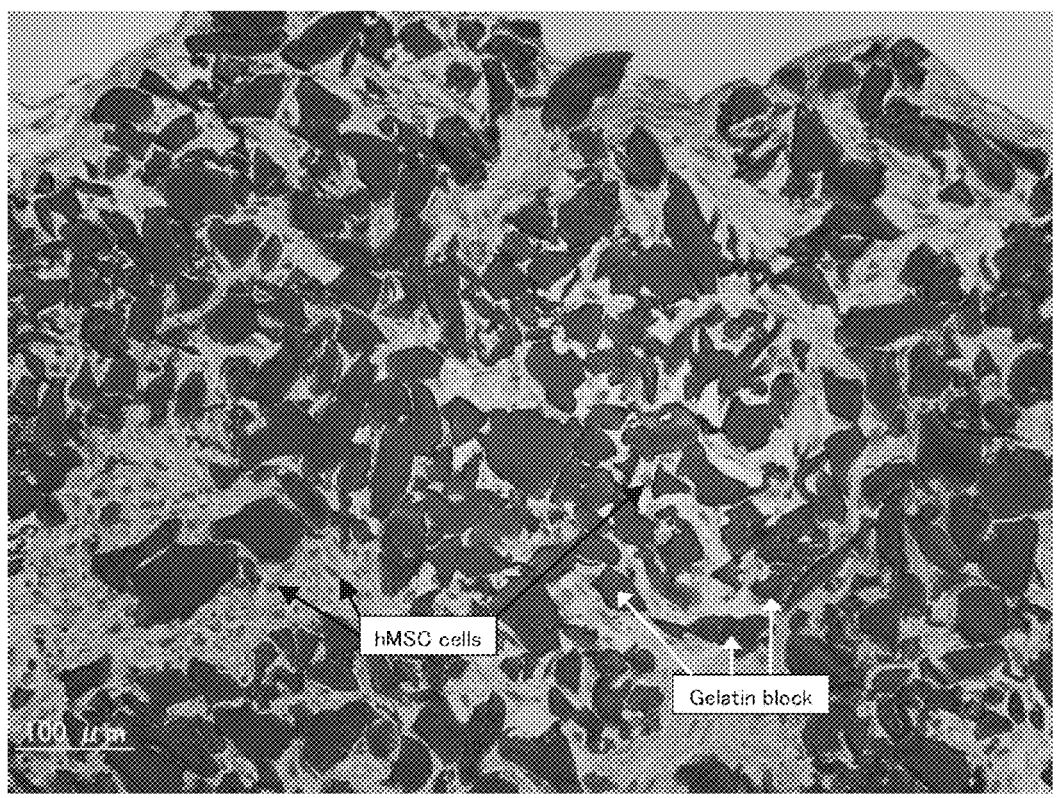

Figure 12 Stereoscopic microscope photograph (time-dependent change) of a mosaic cell mass with an increased volume.

| | In chondrogenic differentiation medium without addition of gelatin block | In chondrogenic differentiation medium with addition of recombinant gelatin block (0.1mg per medium change) | In growth medium without addition of gelatin block | In growth medium with addition of recombinant gelatin block (0.1mg per medium change) |
|---|---|---|---|---|
| Day 7 | 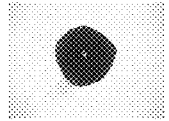 |  | 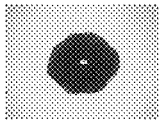 |  |
| Day 10 | 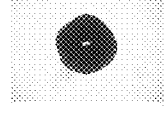 | 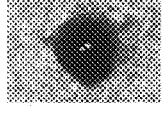 | 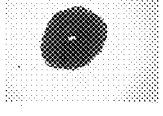 |  |
| Day 14 | 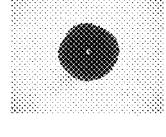 |  | 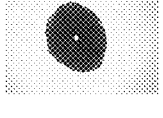 |  |
| Day 17 |  |  | 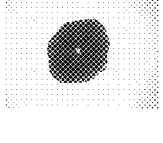 |  |
| Day 21 | 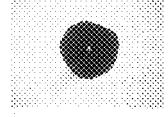 | 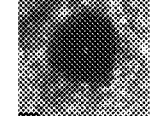 | 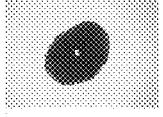 |  |

Figure 13  Time-dependent change in diameter from the stereoscopic microscope photograph of the mosaic cell mass with an increased volume
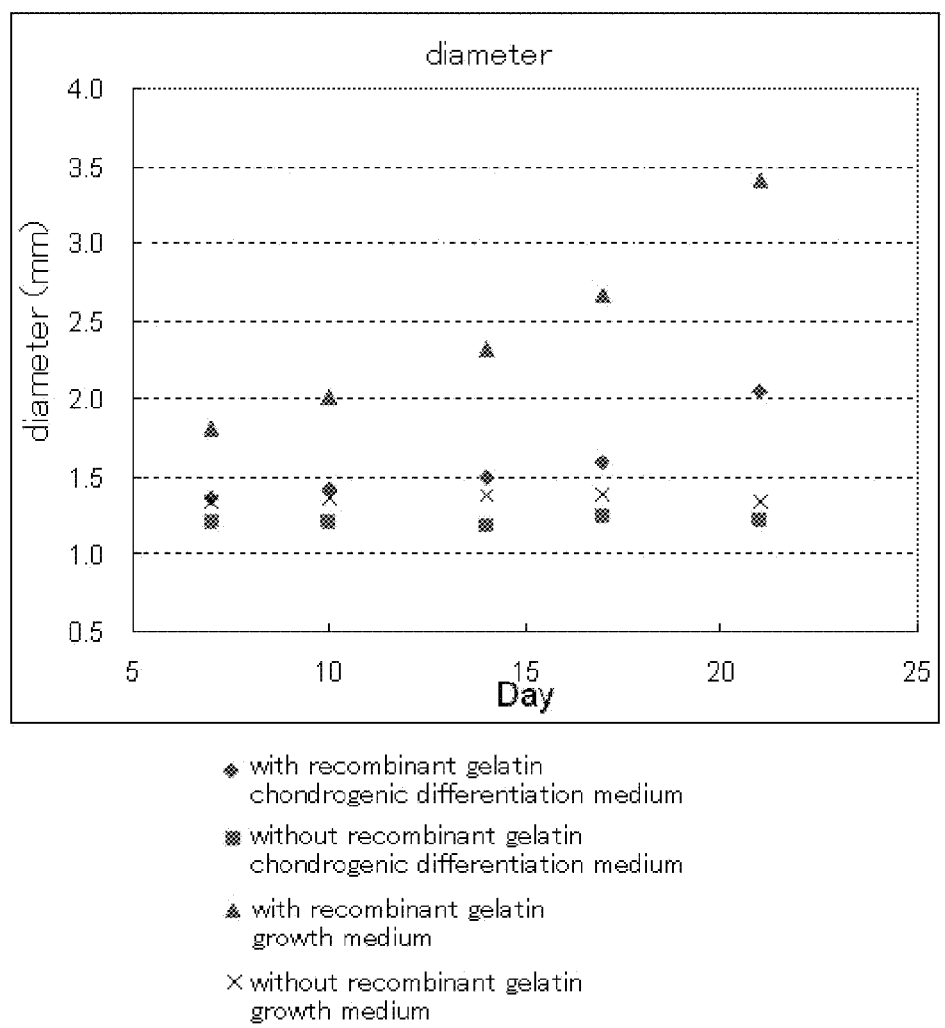

Figure 14 Time-dependent change in area from the stereoscopic microscope photograph of the mosaic cell mass with an increased volume
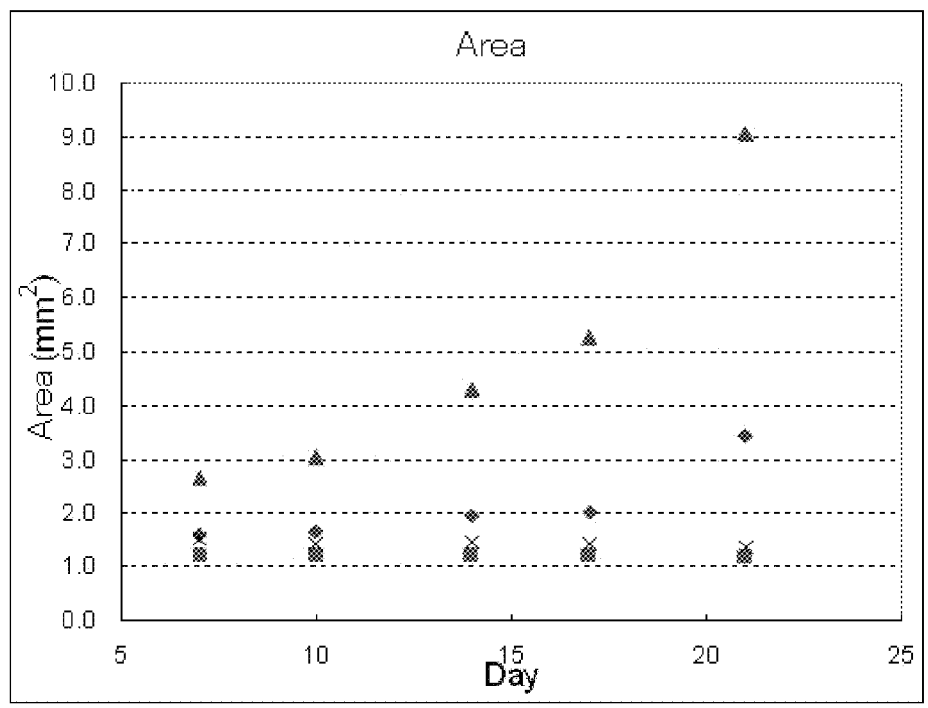

Figure 15  Time-dependent change in volume ($4/3\pi r^3$) determined by calculation from the stereoscopic microscope photograph of the mosaic cell mass with an increased volume
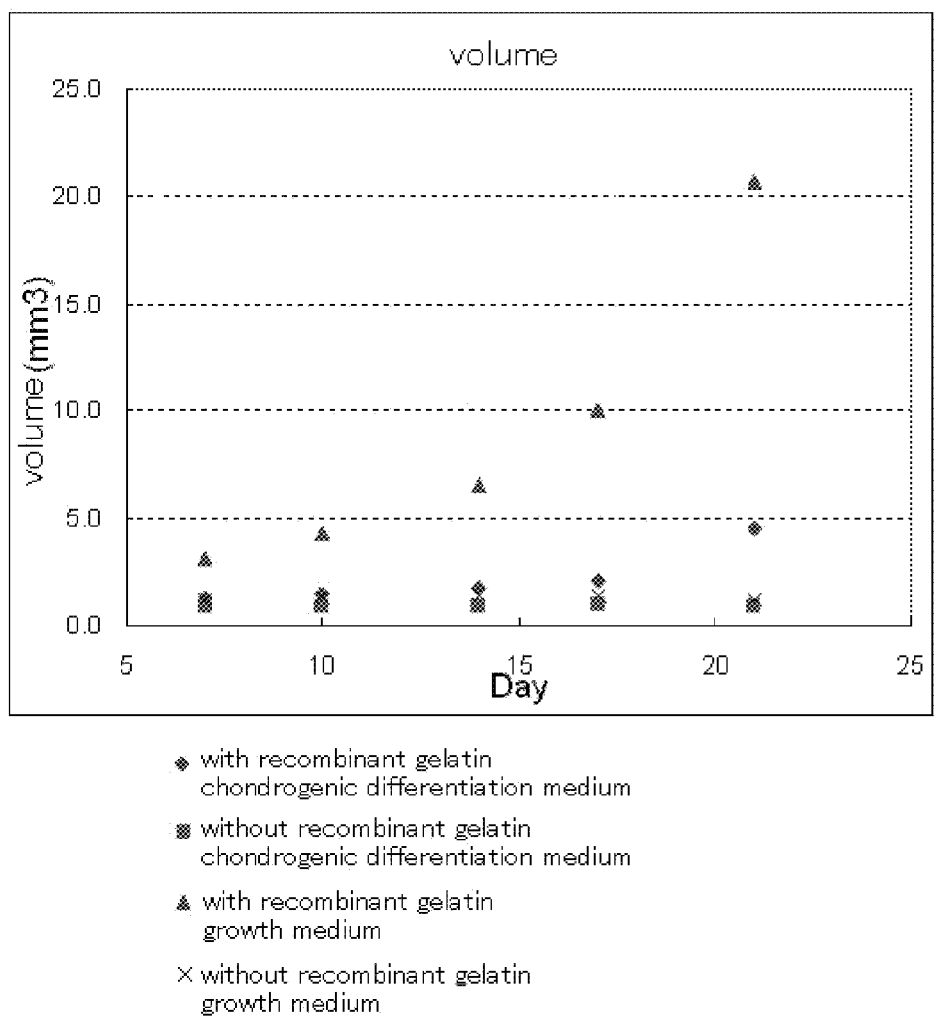

Figure 16 Slice (Day 7 (under the growth medium), magnification: ×5) of a mosaic cell mass containing the recombinant gelatin micro-blocks
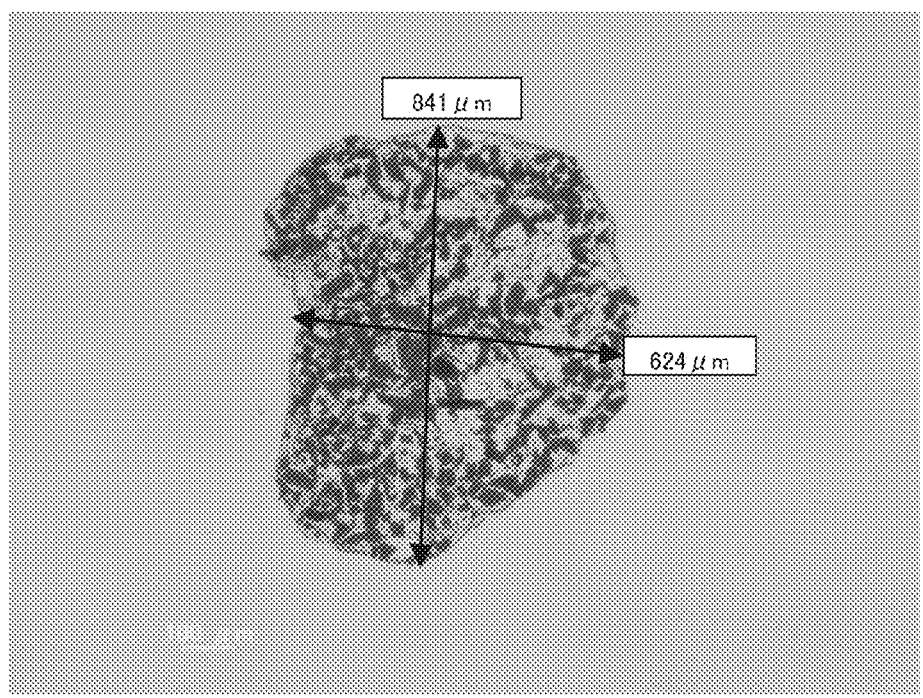

Figure 17 Slice (Day 7 (under the growth medium), magnification: ×10) of a mosaic cell mass containing the recombinant gelatin micro-blocks
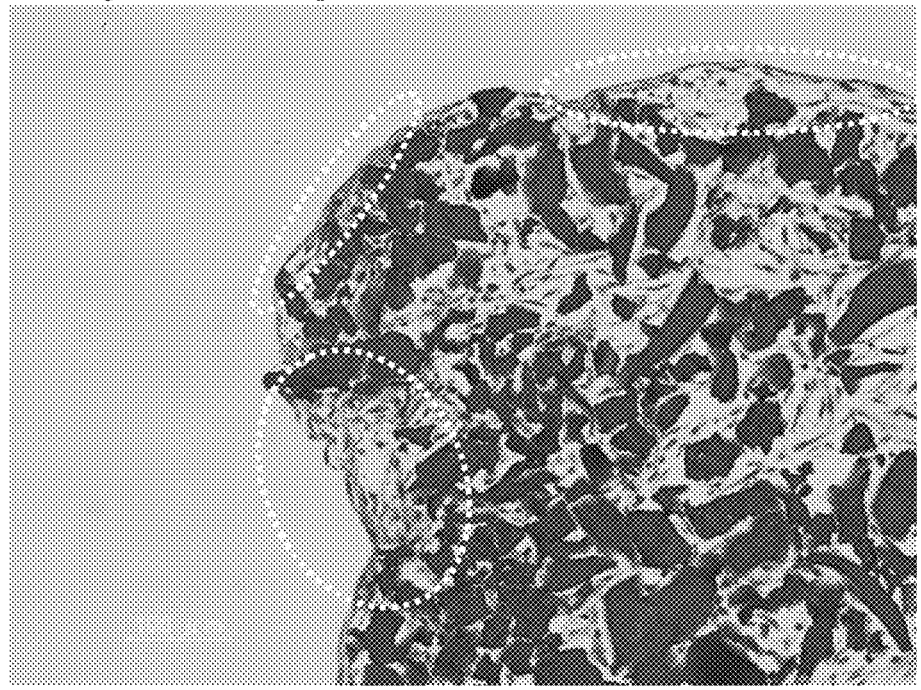
Figure 18 Photograph (magnification: ×5) of a HE slice of Day 21 with an increased volume (the recombinant gelatin blocks were added under the growth medium)
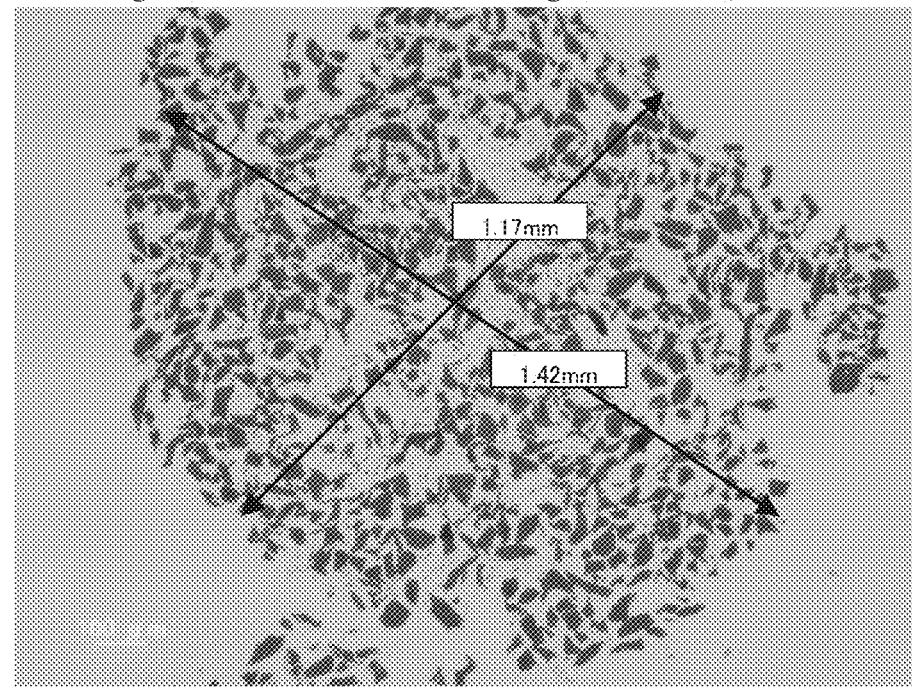

Figure 19 Photograph (magnification: ×40) of a HE slice of Day 21 with an increased volume (the recombinant gelatin blocks were added under the growth medium)
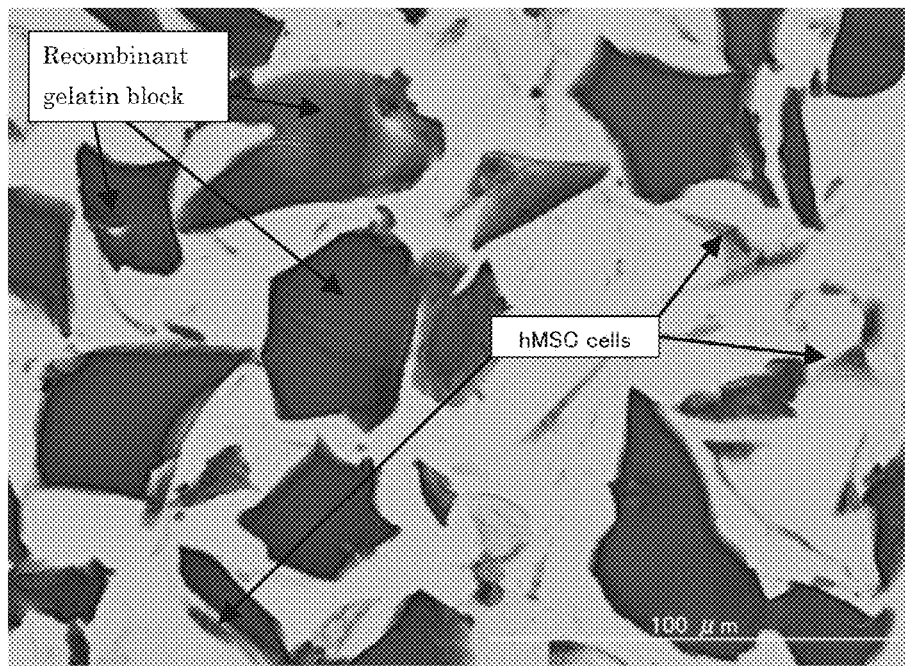

Figure 20A  Photograph of a HE slice of Day 21 with an increased volume (the recombinant gelatin blocks were added under the chondrogenic differentiation medium)(magnification: ×5)
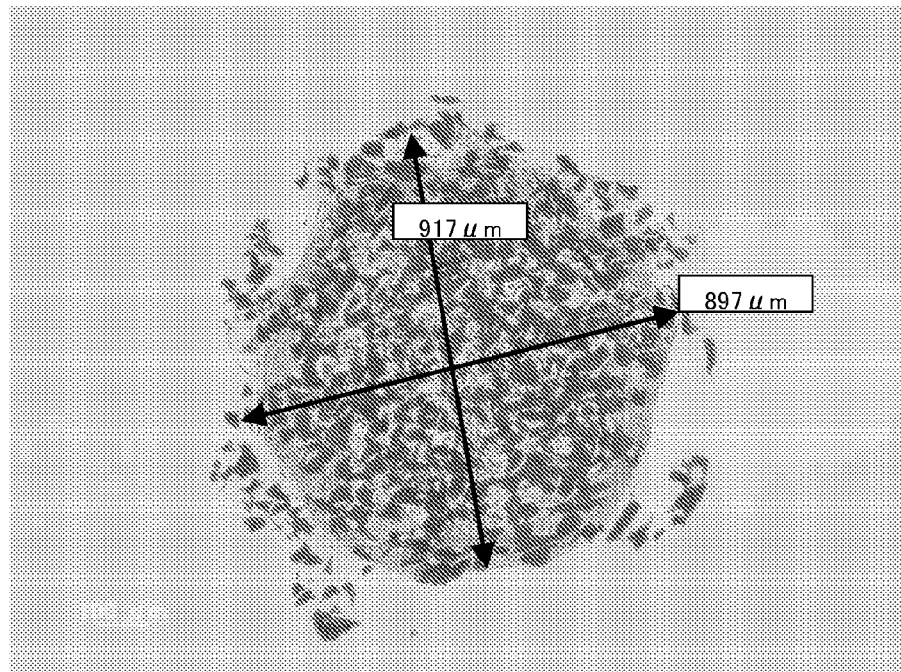
Figure 20B  Photograph of a HE slice of Day 21 with an increased volume (the recombinant gelatin blocks were added under the chondrogenic differentiation medium)(magnification: ×20)
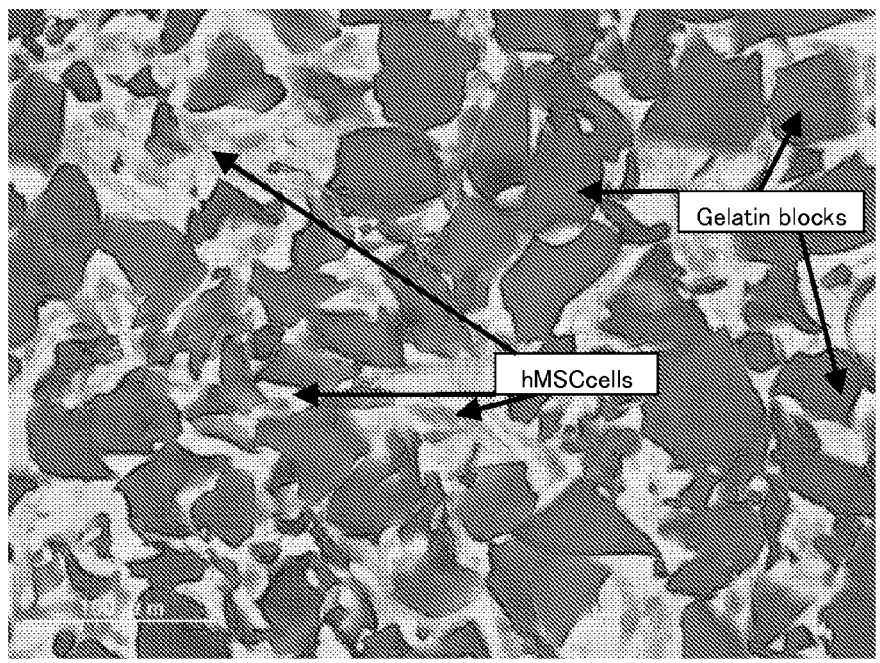

Figure 21    Spectral data of GAG.
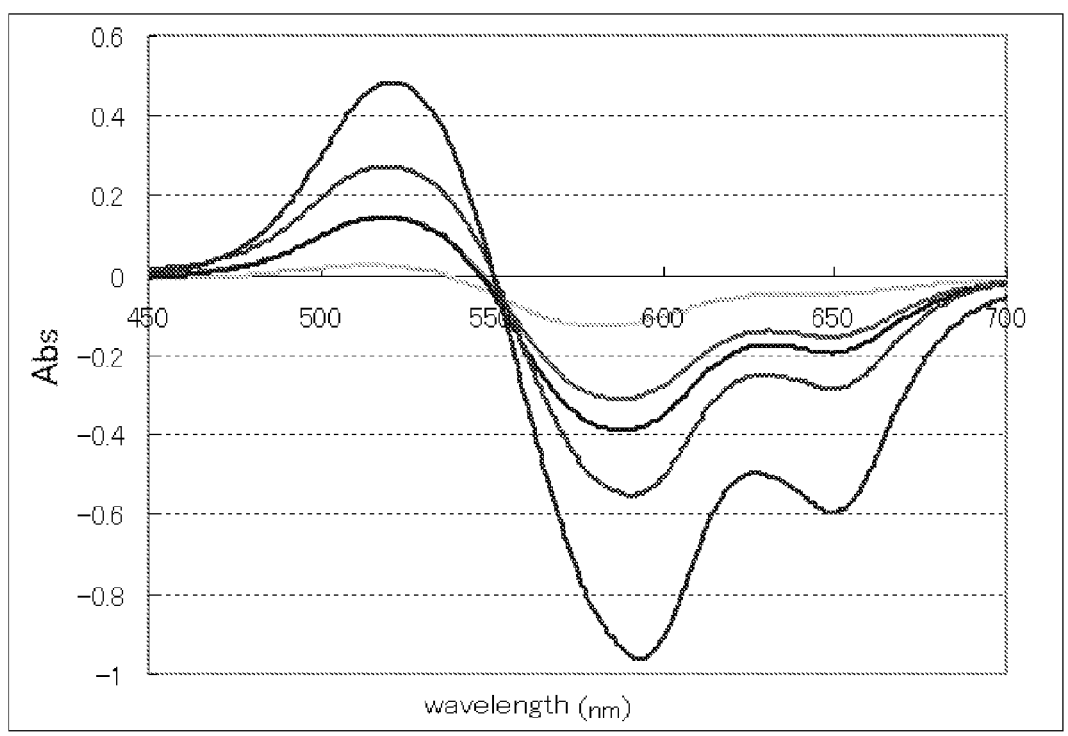

Figure 22 Time-dependent change in the amount of GAG produced in the mosaic cell mass
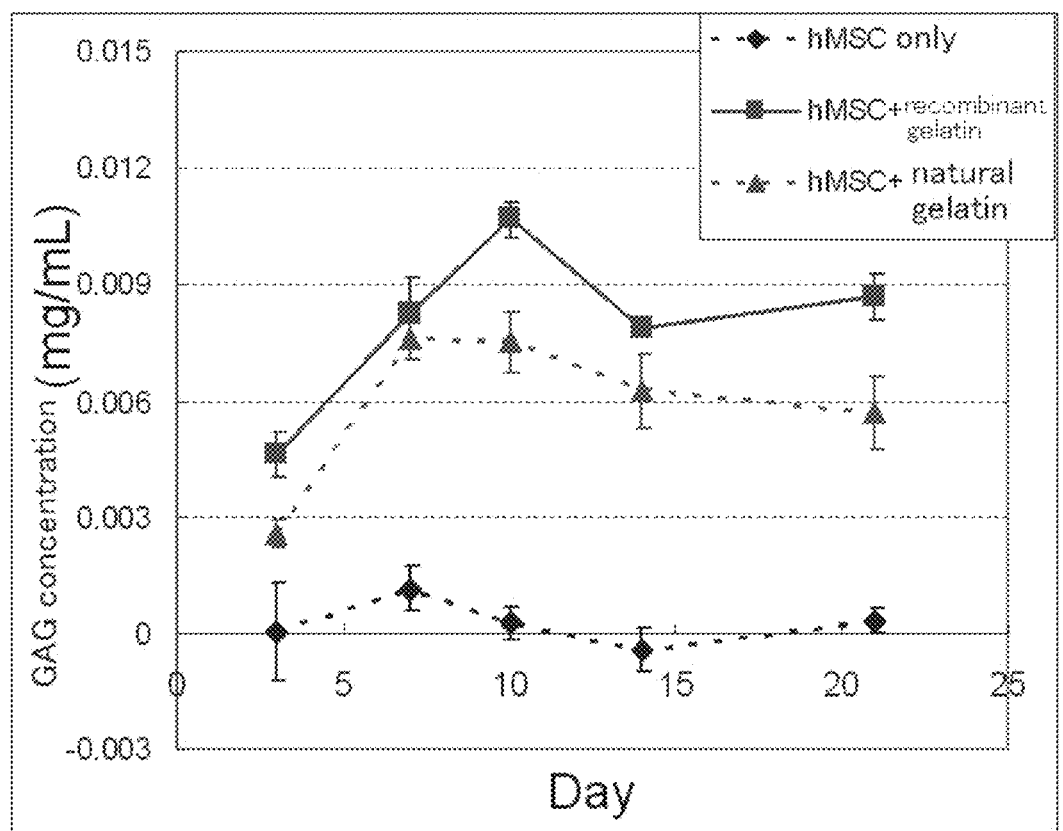

Figure 23  Amount of ATP produced/retained by the cells in the mosaic cell mass (Day 7).
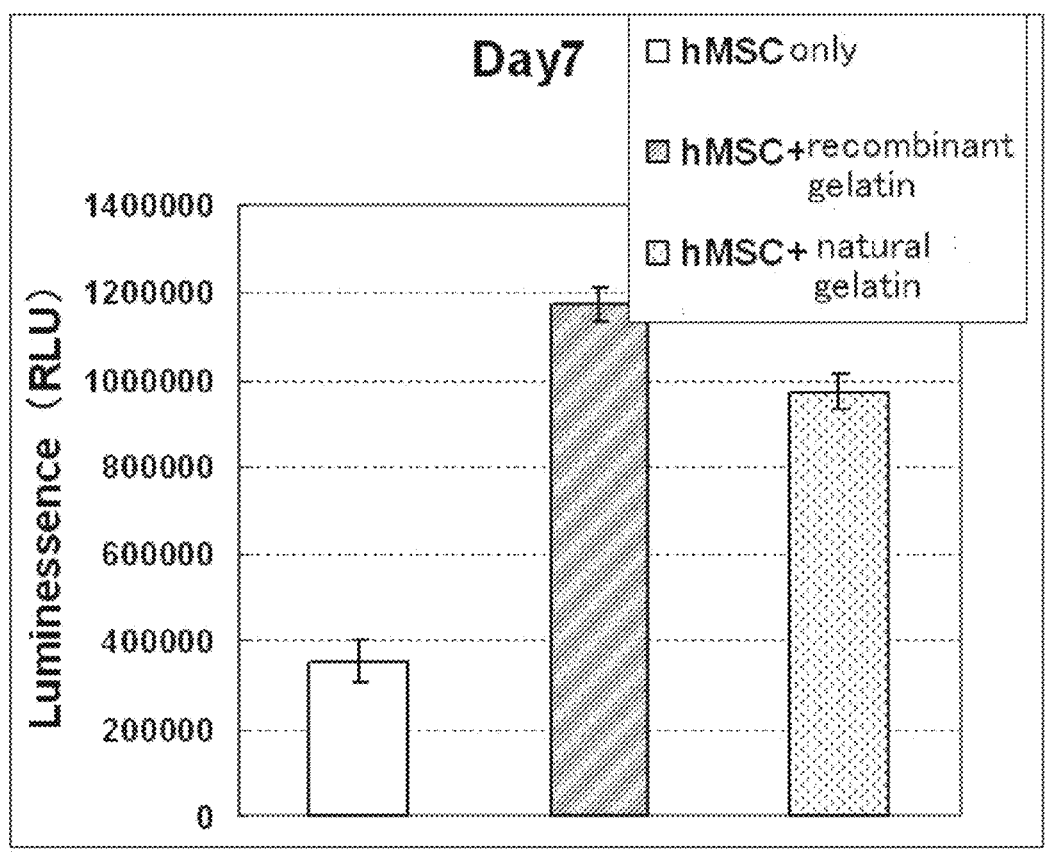

Figure 24  Stereoscopic microscope photograph of Day 2 (growth medium) of a mosaic cell mass prepared using PLGA micro-blocks
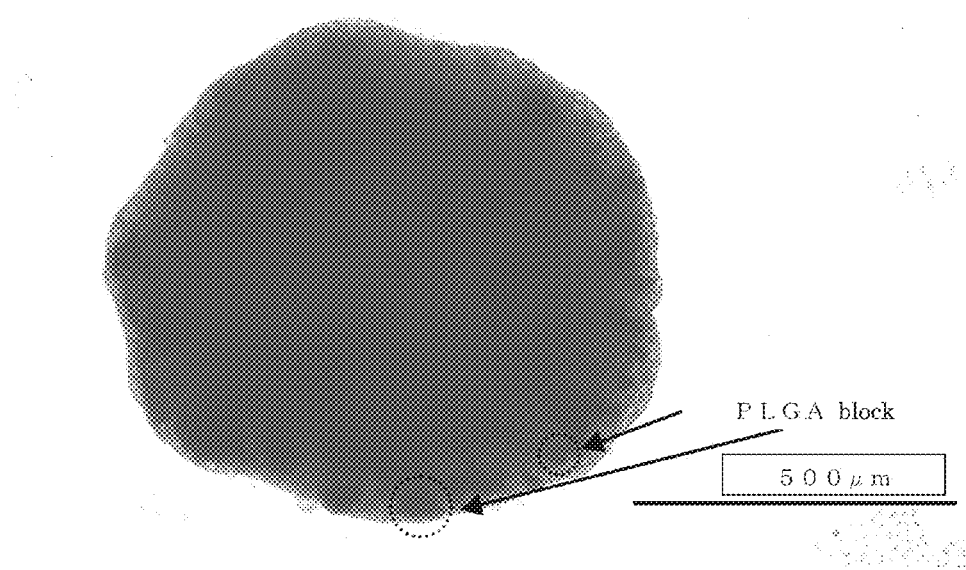

Figure 30
CD29
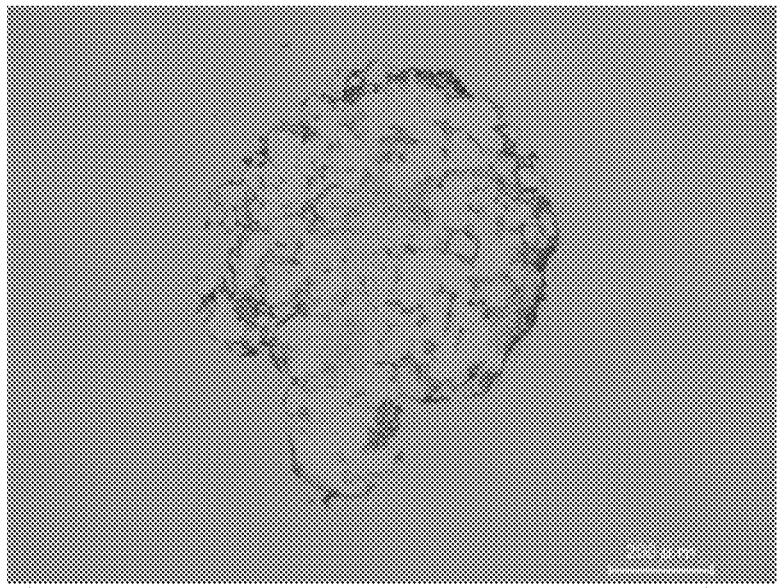
CD31
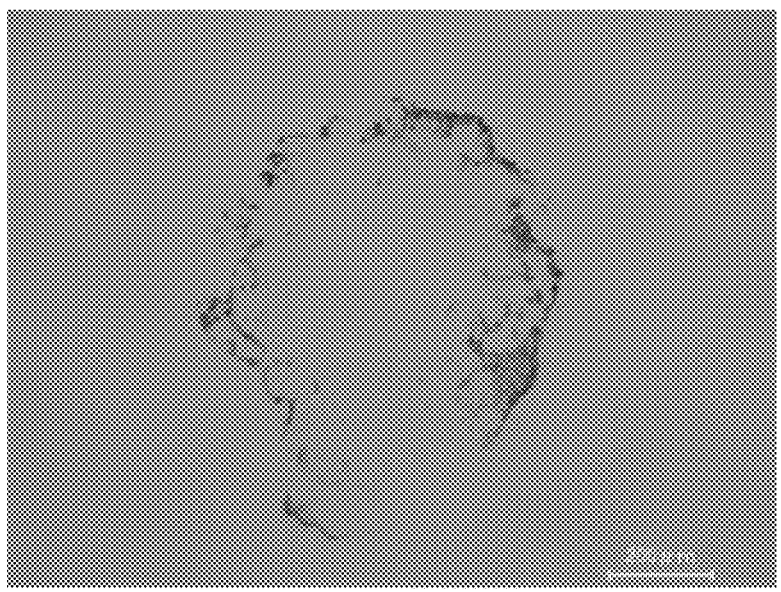

Figure 31
CD29
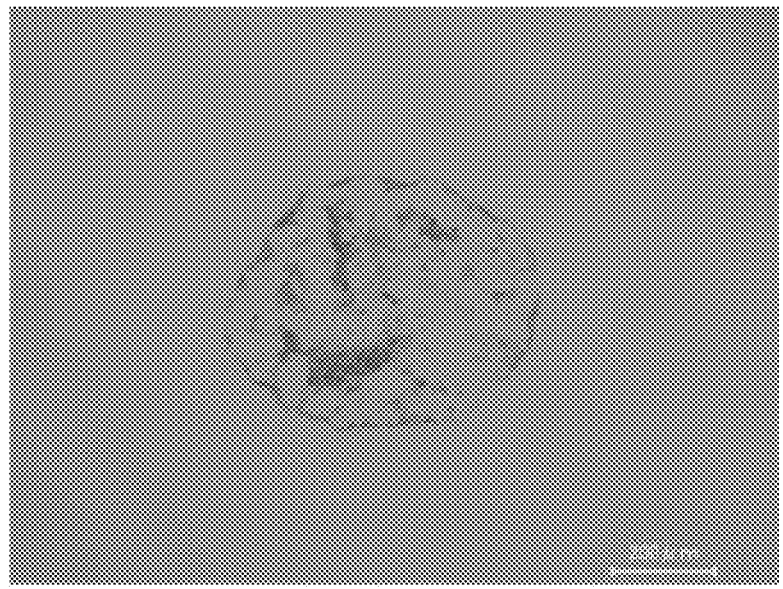
CD31
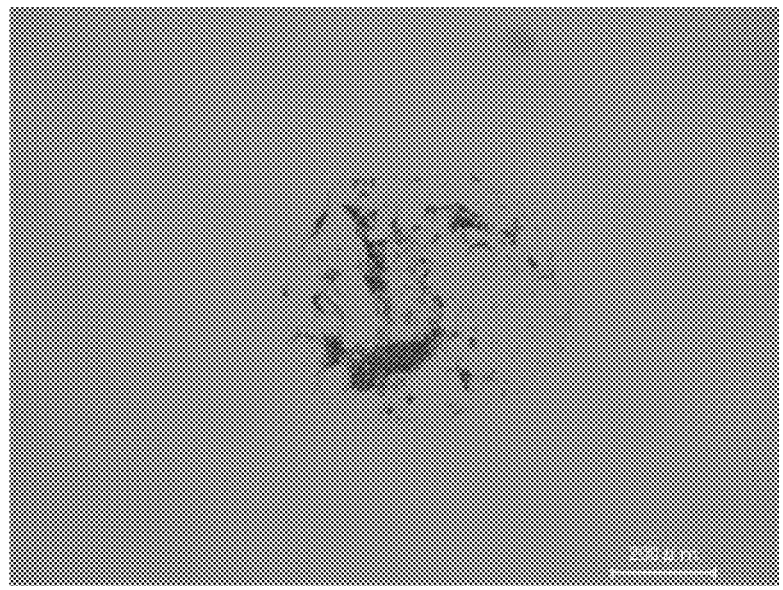

Figure 33
CD29
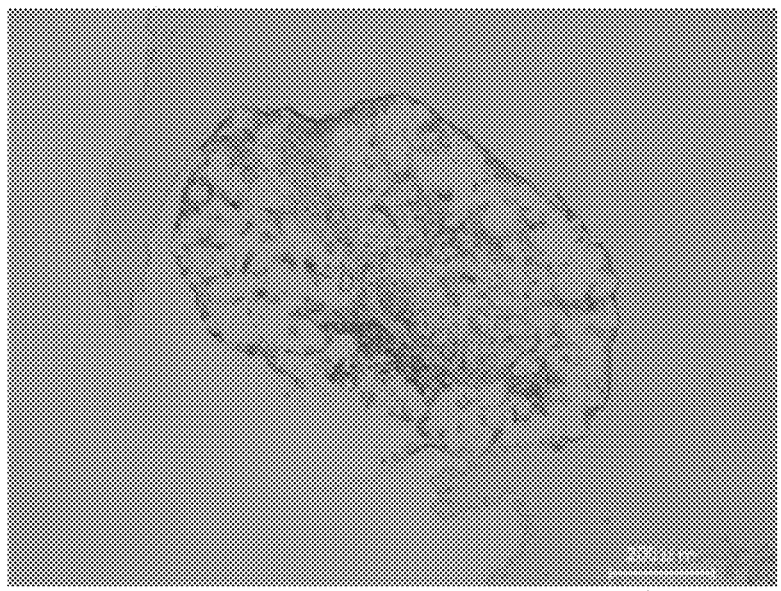
CD31
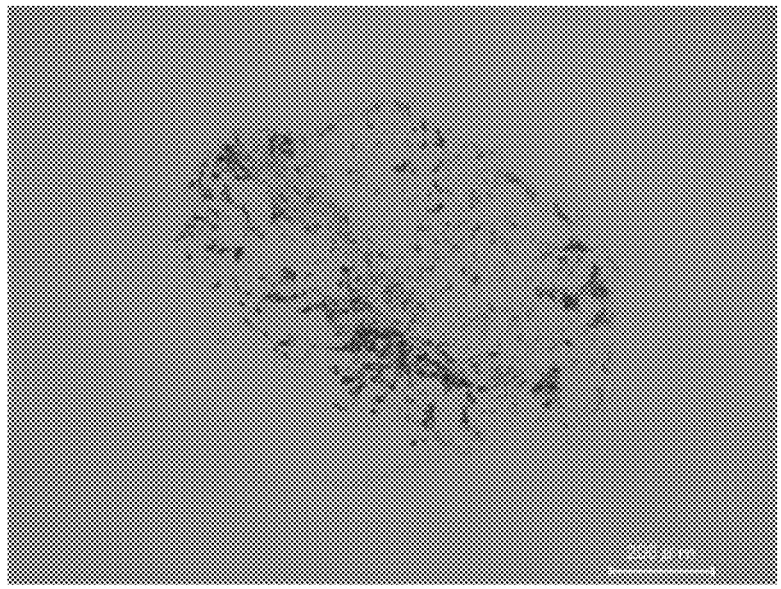

Figure 37
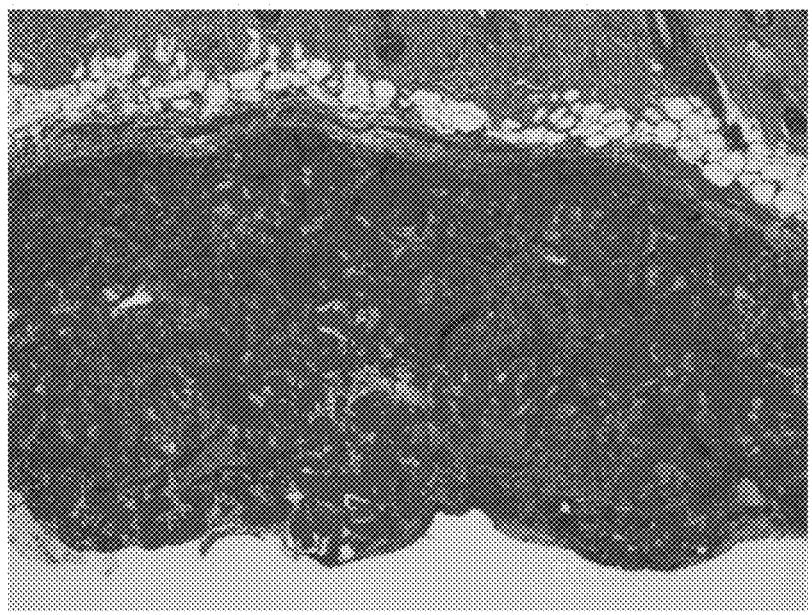
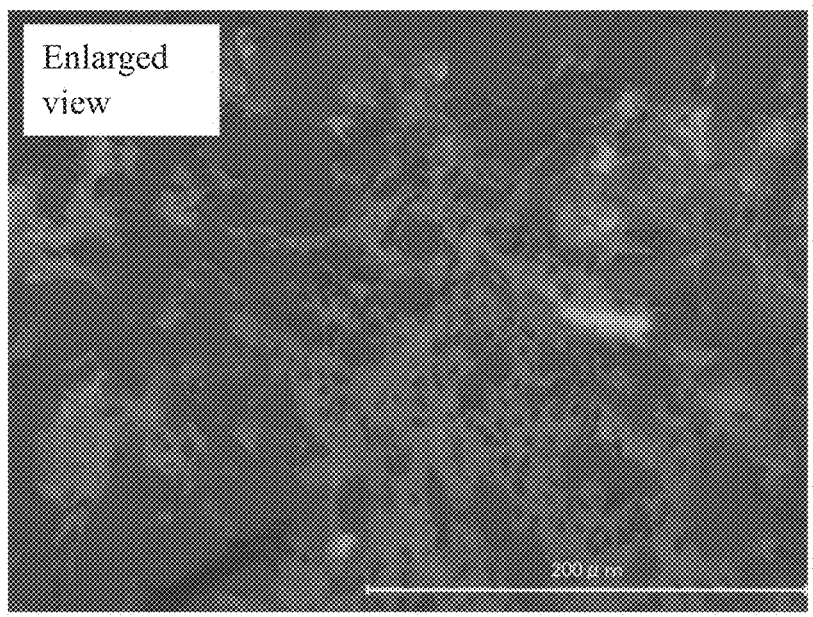

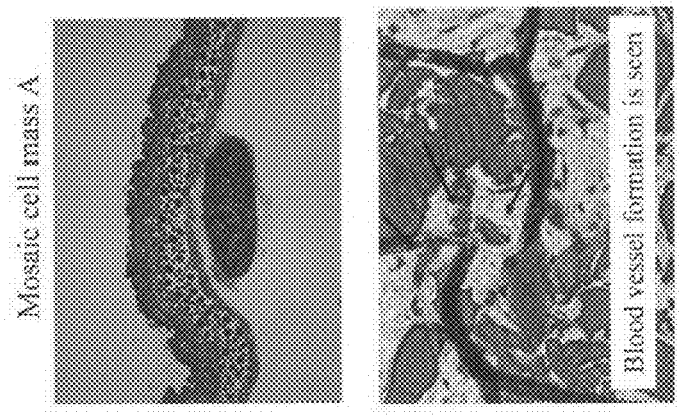
Figure 39: Evaluation of blood vessel formation in the HE-stained slice (14d) of hMSC + hECFC mosaic cell mass

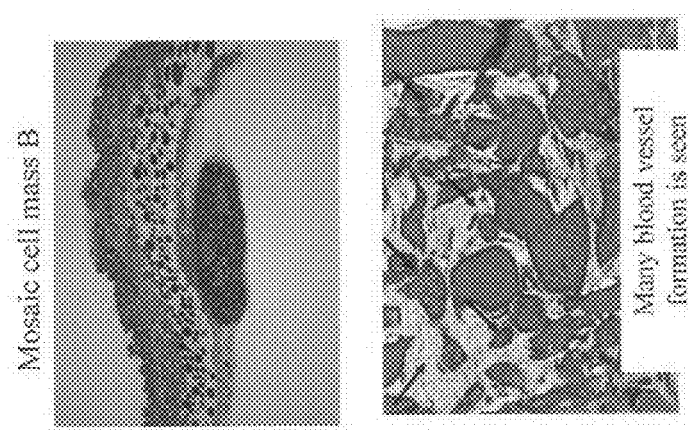
Figure 40. Evaluation of blood vessel formation in the HE-stained slice (14d) of hMSC + hECFC mosaic cell mass

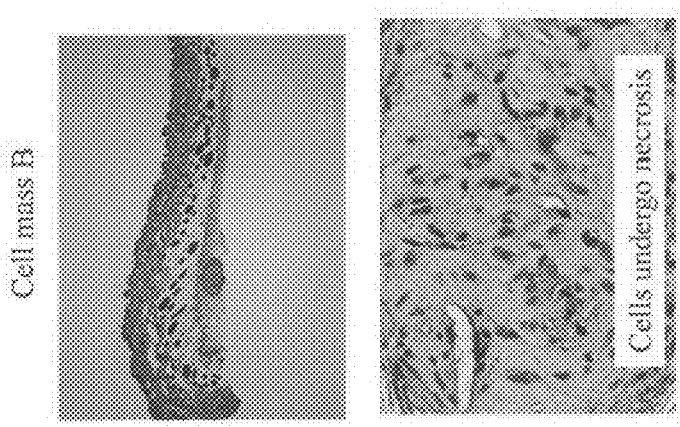
Figure 41: Evaluation of blood vessel formation in the HE-stained slice (14d) of hMSC + hECFC mosaic cell mass

CELL CONSTRUCT FOR CELL TRANSPLANTATION AND CELL AGGREGATE FOR CELL TRANSPLANTATION

TECHNICAL FIELD

The present invention relates to a cell construct for cell transplantation and a cell aggregate for cell transplantation. Specifically, the present invention relates to a cell construct for cell transplantation capable of preventing the necrosis of transplanted cells after transplantation and forming blood vessels at the transplantation site, and a cell aggregate for cell transplantation capable of forming blood vessels at its transplantation site.

BACKGROUND ART

The practical utilization of regenerative medicine, which helps regenerate living tissues/organs that have fallen into functional disorder or functional incompetence, is currently proceeding. The regenerative medicine is novel medical technology of re-creating the same or similar forms or functions as in original tissues using 3 factors, i.e., cells, scaffolds, and growth factors, for living tissues that no longer recover by only natural healing ability intrinsically possessed by organisms. In recent years, treatments using cells have been being gradually realized. Examples thereof include cultured epidermis using autologous cells, cartilage treatment using autologous cartilage cells, bone regeneration treatment using mesenchymal stem cells, cardiac muscle cell sheet treatment using myoblasts, corneal regeneration treatment using corneal epithelial sheets, and nerve regeneration treatment. These novel treatments, unlike conventional alternative medicine based on artificial materials (bone prosthetic materials or hyaluronic acid injection), help repair or regeneration of living tissues and therefore produce high therapeutic effects. In fact, some products such as cultured epidermis or cultured cartilage using autologous cells have been launched.

In this context, for example, the regeneration of cardiac muscle using cell sheets is considered to require a multilayer construct of cell sheets for regenerating thick tissues. Okano et al. have recently developed cell sheets using a temperature-responsive culture dish. The cell sheets do not require treatment with an enzyme such as trypsin and thus retain cell-to-cell binding and adhesion proteins (Non Patent Documents 1 to 6). Such a cell sheet production technique is expected to be useful in the regeneration of cardiac muscle tissues (Non Patent Document 7). Okano et al. have also thought that a thickness of 200 μm or larger is impossible to achieve, and are developing cell sheets also containing vascular endothelial cells introduced therein in order to form vascular network in the cell sheets (Non Patent Document 8).

Also for bone regeneration, bone regeneration sheets comprising cultured cells added to matrices have been developed.

A bone regeneration sheet prepared by layering a cultured cell sheet comprising mesenchymal stem cells cultured into a sheet-like shape and a biodegradable sheet comprising biodegradable substances formed into a sheet-like shape (Patent Document 1) has been proposed. Moreover, there is a sheet for induction of mesenchymal tissue regeneration in which mesenchymal tissue precursor cells differentiated from mesenchymal cells and extracellular matrices are attached onto a porous sheet (Patent Document 2). Then, Patent Document 3 has reported that a sheet of 200 μm or larger in thickness can be formed by the development/optimization of a culture approach, and has also disclosed that the formation of approximately 210 μm cortical bone tissue layer was confirmed.

Furthermore, gel-embedding culture using collagen has been devised as one means of solving insufficient penetration of nutrients by only diffusion into a three-dimensional construct composed of cells (Non Patent Document 9). Moreover, Patent Document 4 states that three-dimensional culture is achieved by linking cells using inorganic ceramic beads.

PRIOR ART DOCUMENTS

[Patent Document 1] JP Patent Publication (Kokai) No. 2003-275294A (2003)
[Patent Document 2] JP Patent Publication (Kokai) No. 2006-116212A (2006)
[Patent Document 3] JP Patent Publication (Kokai) No. 2009-240766A (2009)
[Patent Document 4] JP Patent Publication (Kokai) No. 2004-267562A (2004)
[Non Patent Document 1] Shimizu, T. et al., Circ. Res. 90, e40-48 (2002)
[Non Patent Document 2] Kushida, A. et al., J. Biomed. Mater. Res. 51, 216-223 (2000)
[Non Patent Document 3] Kushida, A. et al., J. Biomed. Mater. Res. 45, 355-362 (1999)
[Non Patent Document 4] Shimizu, T., Yamato, M., Kikuchi, A. & Okano, T., Tissue Eng. 7, 141-151 (2001)
[Non Patent Document 5] Shimizu, T et al., J. Biomed. Mater. Res. 60, 110-117 (2002)
[Non Patent Document 6] Harimoto, M. et al., J. Biomed. Mater. Res. 62, 464-470 (2002)
[Non Patent Document 7] Shimizu, T., Yamato, M., Kikuchi, A. & Okano, T., Biomaterials 24, 2309-2316 (2003)
[Non Patent Document 8] Inflammation and Regeneration vol. 25 No. 3 2005, p. 158-159. The 26th annual meeting of the Japanese Society of Inflammation and Regeneration—Pursuing fusion between inflammation research and regenerative medicine—Mitsuo Okano
[Non Patent Document 9] Sustained growth and three-dimensional organization of primary mammary tumor epithelial cells embedded in collagen gel. J Yang, J Richards, P Bowman, R Guzman, J Enami, K McCormick, S Hamamoto, D Pitelka, and S Nandi. PNAS Jul. 1, 1979 vol. 76 no. 7 3401-3405

SUMMARY OF INVENTION

Object to be Solved by the Invention

Current techniques relating to regenerative medicine cannot provide tissues having a sufficient thickness, because cells to be transplanted are mainly transplanted in a thin sheet form or transplanted in the state of a suspension. Living tissues are originally thick and enable muscle force to allow the heart to beat or permit smooth movement at articular cartilage because of being thick. For general tissue regeneration using cells, the inability to provide thick tissues is considered as a major problem.

Since previous cell sheets cannot form vascular network, sufficiently thick tissues have been difficult to regenerate (Non Patent Documents 5 and 7). This is because nutrition supply to cells in the central portion is lost in a cell sheet allowed to be thick, whereby the cells are killed. Alternatively, cell sheets also containing vascular endothelial cells introduced therein (Non Patent Document 8) have been developed. However, this cannot serve as a realistic solution due to many problems: in addition to the cells of interest, another cell source, i.e., vascular endothelial cells, must be prepared; it is difficult to uniformly induce blood vessels in the cell sheet; and even if the delivery pathway of nutrients can be provided by this means, the prepared nutrition delivery pathway must be precisely connected to an external nutrition delivery pathway in this approach.

In addition, the inventions described in Patent Documents 1 and 2 above are methods involving placing a cultured osteoblast-attached sheet into the body and forming cortical bone from the osteoblast through membranous ossification in vivo. However, osteoblast-like cells cannot be cultured in a layered state, and due to this problem, sheets having an osteoblast layer have failed to provide regeneration sheets in which the thickness of a cell layer exceeds 100 μm.

As described above, it was a difficult challenge in the past to provide cells as a thick composition for many tissue repairs. The leading cause thereof is the insufficient penetration of nutrients by only diffusion into a three-dimensional construct composed of cells. Gel-embedding culture using collagen has been devised as one means of solving this (Non Patent Document 9). However, cells embedded in a gel cannot solve this problem at its source, because the cells are moved from the central portion of the gel toward the outer region and thus, are not uniformly present in the gel to reduce the cell density of the central portion. Moreover, the three-dimensional cell construct prepared by gel embedding cannot be bound/fused to another three-dimensional construct and thus, cannot form a three-dimensional construct above the size prepared at the time of cell inoculation. Thus, the means of preparing small gels and then fusing the gels to each other to prepare a construct in which cells are uniformly distributed cannot be adopted.

Moreover, as described above, Patent Document 4 states that three-dimensional culture is achieved by linking cells using inorganic ceramic beads. However, inorganic ceramics are inferior in water retention, solution exchange, diffusion of nutrition, and buffer capacity and cannot actually provide a thick cell composition. In fact, in Examples of Patent Document 4, cells were bonded to 150 to 460 μm particles, over which a thick PLLA nonwoven fabric (1 cm) was layered to merely increase an apparent thickness. The actual cell-containing layer was merely a layer of tens of μm at the thickest on the surface of the inorganic ceramic beads. Even if the 1 cm PLLA nonwoven fabric having no cell is regarded as a construct, it is merely a construct having significantly nonuniform cell distribution. Thus, only the three-dimensional cell construct having nonuniform cell distribution in the construct or the construct having a substantially thin cell layer has been provided so far.

As described above, the conventional techniques have failed to provide biological materials that sufficiently meet requirements for a sufficient thickness suitable for cell transplantation, prevention of the necrosis of transplanted cells, and blood vessel formation. Biological materials for cell transplantation that satisfy these requirements have been demanded.

Thus, an object of the present invention is to provide a cell construct for cell transplantation capable of having a thickness suitable for cell transplantation, preventing the necrosis of transplanted cells, and forming blood vessels in the transplantation site after transplantation.

Means for Solving the Object

As a result of conducting diligent studies to attain the object, the present inventors have completed the present invention by finding that the object can be attained by using a construct in which polymer blocks having biocompatibility (blocks containing a polymer material having biocompatibility) and cells are arranged in a particular pattern as a cell construct for cell transplantation intended for use in cell transplantation.

The cell construct for cell transplantation according to the present invention is characterized in that it comprises polymer blocks having biocompatibility and cells of at least one type, wherein the plural polymer blocks are arranged in spaces between the plural cells.

In the present invention, the polymer blocks each preferably have a size from 1 μm to 700 μm, and more preferably from 10 μm to 300 μm. In the cell construct for cell transplantation according to the present invention, the thickness or diameter thereof is preferably from 400 μm to 3 cm, and more preferably from 720 μm to 1 cm. The ratio between the polymer blocks and the cells is preferably from 0.0000001 μg to 1 μg of the polymer blocks per cell. Preferably, the cell construct for cell transplantation is produced by incubating a mixture of the polymer blocks having biocompatibility and a culture solution comprising the cells.

Preferably, the polymer having biocompatibility is a biodegradable material. Examples of the polymer having biocompatibility include polypeptide, polylactic acid, polyglycolic acid, PLGA, hyaluronic acid, glycosaminoglycan, proteoglycan, chondroitin, cellulose, agarose, carboxymethylcellulose, chitin, or chitosan. Preferred examples include gelatin, collagen, elastin, fibronectin, ProNectin, laminin, tenascin, fibrin, fibroin, entactin, thrombospondin, or RetroNectin.

Preferably, the polymer having biocompatibility is cross-linked. More preferably, the cross-linking is performed with an aldehyde, a condensing agent, or an enzyme.

Preferably, the polymer having biocompatibility is a recombinant peptide. Preferably, the polymer having biocompatibility has two or more cell adhesion signals in a molecule. Preferably, the recombinant peptide is represented by the formula:

A-[(Gly-X-Y)$_n$]$_m$-B wherein A represents any amino acid or amino acid sequence; B represents any amino acid or amino acid sequence; each X of total n independently represents any amino acid; each Y of total n independently represents any amino acid; n represents an integer of 3 to 100; m represents an integer of 2 to 10; and each Gly-X-Y of total n may be the same as or different from each other.

More preferably, the recombinant peptide is represented by the formula:

Gly-Ala-Pro-[(Gly-X-Y)$_{63}$]$_3$-Gly wherein each X of total 63 independently represents any amino acid; each Y of total 63 independently represents any amino acid; and each Gly-X-Y of total 63 may be the same as or different from each other.

Preferably, the recombinant peptide has (1) the amino acid sequence represented by SEQ ID NO: 1, or (2) an amino acid sequence having 80% or higher homology to the amino acid sequence represented by SEQ ID NO: 1 and having biocompatibility. Preferably, the cell construct for cell transplantation according to the present invention further comprises an angiogenesis factor.

Preferably, the cells in the present invention are cells selected from the group consisting of pluripotent cells, somatic stem cells, precursor cells, and mature cells. A cell construct for cell transplantation comprising non-vascular cells can be preferably used as the cell construct for cell transplantation according to the present invention. The cell construct for cell transplantation wherein the cells are only non-vascular cells, can be also preferably used. Preferably, the cells are of two or more types comprising both non-vascular cells and vascular cells. In this case, the cell construct for cell transplantation preferably has a region wherein the area of the vascular cells in the central portion of the cell construct is larger than the area of the vascular cells in the peripheral portion. Further preferably, the cell construct for cell transplantation has a region wherein the ratio of the vascular cells in the central portion is 60% to 100% to the whole areas of the vascular cells. Preferably, the cell construct for cell transplantation has a region wherein the density of the vascular cells in the central portion is $1.0 \times 10^{-4}$ cells/$\mu m^3$ or more. The cell construct for cell transplantation according to the present invention may include a cell construct for cell transplantation in which blood vessels have been formed by using the cell construct for cell transplantation according to the present invention wherein the cells are of two or more types comprising both non-vascular cells and vascular cells.

The cell aggregate for cell transplantation according to the present invention is characterized in that it comprises non-vascular cells and vascular cells, wherein the cell aggregate for cell transplantation satisfies at least one of the requirements:
(1) the cell aggregate has a region wherein the area of the vascular cells in the central portion of the cell aggregate is larger than the area of the vascular cells in the peripheral portion, and
(2) the cell aggregate has a region wherein the density of the vascular cells in the central portion is $1.0 \times 10^{-4}$ cells/$\mu m^3$ or more.

Preferably, the cell aggregate for cell transplantation according to the present invention satisfies both of the requirements (1) and (2). Preferably, the cell aggregate for cell transplantation has a region wherein the ratio of the vascular cells in the central portion is 60% to 100% to the whole area of the vascular cells.

The present invention further provides a method for transplanting cells, which comprises transplanting the cell construct for cell transplantation of the present invention.

The present invention further provides a method for transplanting cells, which comprises transplanting the cell aggregate for cell transplantation of claim 17 to a subject.

Effect of the Invention

The cell construct for cell transplantation of the present invention can have a thickness suitable for cell transplantation. In addition, polymer blocks having biocompatibility (blocks containing a polymer material having biocompatibility) and cells are three-dimensionally arranged in a mosaic pattern, whereby a three-dimensional cell construct in which the cells are uniformly present can be formed to enable nutrition delivery into the three-dimensional cell construct from outside. As a result, when cell transplantation is performed using the cell construct for cell transplantation of the present invention, transplantation with the necrosis of the transplanted cells prevented can be achieved. Furthermore, even in the case where vascular cells are not used as a cell species used, the cell construct is capable of forming blood vessels at the transplantation site after transplantation. Moreover, the cell aggregate for cell transplantation of the present invention is capable of forming blood vessels at its transplantation site after transplantation.

BRIEF DESCRIPTION OF DRAWINGS

The patent or application file contains at least one drawing executed in color. Copies of this patent or patent application publication with color drawing(s) will be provided by the Patent and Trademark Office upon request and payment of the necessary fee.

FIG. 1 shows a stereoscopic microscope photograph of Day 7 (chondrogenic differentiation medium) of a mosaic cell mass prepared using recombinant peptide micro-blocks.

FIG. 2 shows a stereoscopic microscope photograph of Day 7 (chondrogenic differentiation medium) of a mosaic cell mass prepared using natural gelatin micro-blocks.

FIG. 3 shows a photograph of a slice (HE-stained, magnification: ×5) of the mosaic cell mass containing the recombinant peptide micro-blocks.

FIG. 4 shows a photograph of a slice (HE-stained, magnification: ×10) of the mosaic cell mass containing the recombinant peptide micro-blocks.

FIG. 5 shows a photograph of a slice (HE-stained, magnification: ×40) of the mosaic cell mass containing the recombinant peptide micro-blocks.

FIG. 6 shows the fusion of the mosaic cell masses.

FIG. 7 shows a photograph of a HE-stained slice (magnification: ×5) from the fusion of the mosaic cell masses (fusion of three mosaic cell masses).

FIG. 8 shows a photograph of a HE-stained slice (magnification: ×10) from the fusion of the mosaic cell masses (fusion of three mosaic cell masses).

FIG. 9 shows a photograph of a HE-stained slice (magnification: ×20) from the fusion of the mosaic cell masses (fusion of three mosaic cell masses).

FIG. 10 shows a photograph of a HE-stained slice (magnification: ×5) from the fusion of the mosaic cell masses (fusion of three mosaic cell masses).

FIG. 11 shows a photograph of a HE-stained slice (magnification: ×10) from the fusion of the mosaic cell masses (fusion of three mosaic cell masses).

FIG. 12 shows a stereoscopic microscope photograph (time-dependent change) of a mosaic cell mass with an increased volume.

FIG. 13 shows time-dependent change in diameter from the stereoscopic microscope photograph of the mosaic cell mass with an increased volume.

FIG. 14 shows time-dependent change in area from the stereoscopic microscope photograph of the mosaic cell mass with an increased volume.

FIG. 15 shows time-dependent change in volume ($4/3\pi r^3$) determined by calculation from the stereoscopic microscope photograph of the mosaic cell mass with an increased volume.

FIG. 16 shows a slice (Day 7 (under the growth medium), magnification: ×5) of a mosaic cell mass containing the recombinant peptide micro-blocks.

FIG. 17 shows a slice (Day 7 (under the growth medium), magnification: ×10) of a mosaic cell mass containing the recombinant peptide micro-blocks.

FIG. 18 shows a photograph (magnification: ×5) of a HE slice of Day 21 with an increased volume (the recombinant peptide blocks were added under the growth medium).

FIG. 19 shows a photograph (magnification: ×40) of a HE slice of Day 21 with an increased volume (the recombinant peptide blocks were added under the growth medium).

FIGS. 20A and 20B show photographs (magnification: ×5 (FIG. 20A) and ×20 (FIG. 20B)) of a HE slice of Day 21 with an increased volume (the recombinant peptide blocks were added under the chondrogenic differentiation medium).

FIG. 21 shows spectral data of GAG.

FIG. 22 shows time-dependent change in the amount of GAG produced in the mosaic cell mass.

FIG. 23 shows the amount of ATP produced/retained by the cells in the mosaic cell mass (Day 7).

FIG. 24 shows a stereoscopic microscope photograph of Day 2 (growth medium) of a mosaic cell mass prepared using PLGA micro-blocks.

FIG. 30 shows a photograph of a slice (immunostained with an anti-CD29 antibody and an anti-CD31 antibody) of a mosaic cell mass produced in Example 20-(1) using the recombinant peptide.

FIG. 31 shows a photograph of a slice (immunostained with an anti-CD29 antibody and an anti-CD31 antibody) of a mosaic cell mass produced in Example 20-(2)A using the recombinant peptide.

FIG. 33 shows a photograph of a slice (immunostained with an anti-CD29 antibody and an anti-CD31 antibody) of a mosaic cell mass produced in Example 20-(3) using the recombinant peptide.

FIG. 37 shows a photograph of a tissue slice (HE-stained) of a transplantation site after transplantation of the mosaic cell mass A (Example 20-(2)) containing the recombinant peptide micro-blocks.

FIG. 39 shows a photograph of a tissue slice (HE-stained) of a transplantation site after transplantation of the mosaic cell mass A (Example 20-(2)) containing the recombinant peptide micro-blocks.

FIG. 40 shows a photograph of a tissue slice (HE-stained) of a transplantation site after transplantation of the mosaic cell mass B (Example 20-(2)) containing the recombinant peptide micro-blocks.

FIG. 41 shows a photograph of a tissue slice (HE-stained) of a transplantation site after transplantation of a cell mass (B of Comparative Example 2).

DESCRIPTION OF EMBODIMENTS

Figure 25:
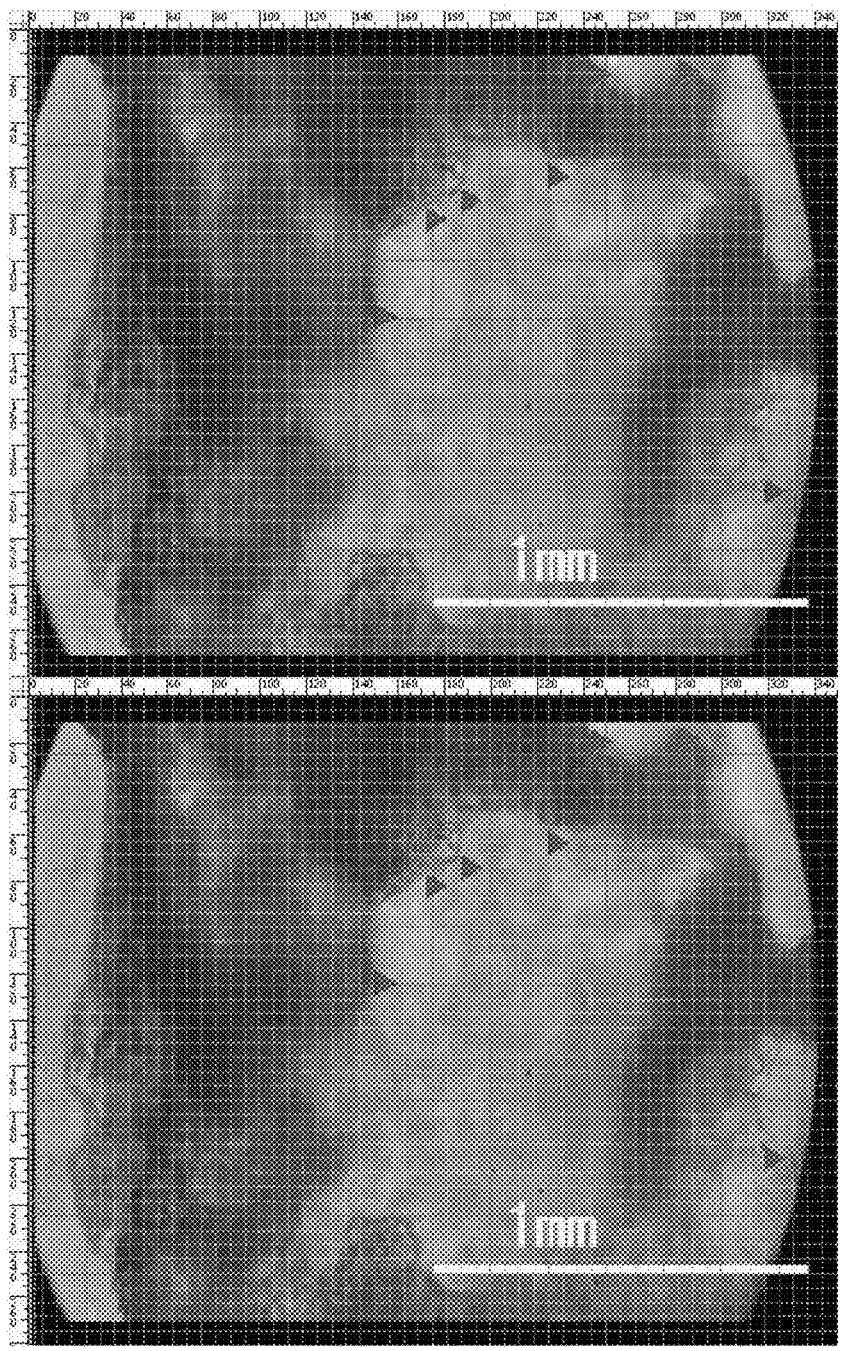
FIG. 25 shows the manner in which a mosaic cell mass consisting of cardiac muscle cells and the recombinant peptide micro-blocks beats in synchronization as a whole.

Hereinafter, the embodiments of the present invention will be described in detail.

The cell construct for cell transplantation of the present invention comprises polymer blocks having biocompatibility and cells of at least one type, wherein the plural polymer blocks are arranged in spaces between the plural cells. Examples of an aspect thereof include a cell construct comprising plural polymer blocks having biocompatibility and plural cells, wherein one or plural polymer blocks are arranged in each of some or all of plural spaces formed by the plural cells.

The shape of the polymer blocks according to the present invention is not particularly limited and is, for example, amorphous, spherical, particulate, powdery, porous, fibrous, spindle-like, flat, and sheet-like shapes, preferably amorphous, spherical, particulate, powdery, and porous shapes, more preferably an amorphous shape. The term "amorphous" represents a nonuniform surface shape, for example, matter having surface irregularities, such as rocks.

In the cell construct for cell transplantation of the present invention, plural polymer blocks are arranged in spaces between plural cells. In this context, the "spaces between the cells" do not have to be closed spaces created by the constituent cells and need only to be flanked by the cells. It is not required that all the cells should create such spaces therebetween. There may be a region in which the cells are in contact with each other. The distance of each space between the cells via the polymer block(s), i.e., the distance of the space from a certain cell to a selected cell located nearest from the certain cell, is not particularly limited and is preferably, the size of polymer block(s). The preferable distance is also in the range of preferable sizes of the polymer block(s).

Moreover, the polymer blocks according to the present invention are flanked by the cells in the constitution. It is not required that all the polymer blocks should be flanked by the cells. There may be a region in which the polymer blocks are in contact with each other. The distance between the polymer blocks via the cell(s), i.e., the distance from a certain polymer block to a selected polymer block located nearest from the certain polymer block, is not particularly limited and is preferably the size of one cell used or a cell mass containing a cell population, for example, from 10 μm to 1000 μm, preferably from 10 μm to 100 μm, more preferably from 10 μm to 50 μm.

In the present specification, the phrase "uniformly present" is used, as described in a "three-dimensional cell construct in which the cells are uniformly present". However, this phrase does not mean complete uniformity but means that the cells are distributed in a range that achieves the effects of the present invention, i.e., enables nutrition delivery into the three-dimensional cell construct from outside, prevents the necrosis of transplanted cells, and allows blood vessel formation at the transplantation site after transplantation.

(1) Polymer Material Having Biocompatibility (1-1) Polymer Material

The polymer having biocompatibility used in the present invention is not particularly limited by whether or not the polymer is degraded in vivo as long as it has affinity for organisms. It is preferred to be composed of a biodegradable material. A non-biodegradable material is specifically at least one material selected from the group consisting of PTFE, polyurethane, polypropylene, polyester, vinyl chloride, polycarbonate, acryl, stainless, titanium, silicone, and MPC (2-methacryloyloxyethyl phosphorylcholine). A biodegradable material is specifically at least one material selected from the group consisting of polypeptide, polylactic acid, polyglycolic acid, PLGA (poly(lactic-co-glycolic acid)), hyaluronic acid, glycosaminoglycan, proteoglycan, chondroitin, cellulose, agarose, carboxymethylcellulose, chitin, and chitosan. Among them, polypeptide is particularly preferable. In this context, these polymer materials may be given a contrivance to enhance cell adhesiveness. Methods such as [1] "coating of matrix surface with a cell-adhesive substrate (fibronectin, vitronectin, and laminin) or a cell adhesion sequence (RGD sequence, LDV sequence, REDV (SEQ ID NO: 2) sequence, YIGSR (SEQ ID NO: 3) sequence, PDSGR (SEQ ID NO: 4) sequence, RYVVLPR (SEQ ID NO: 5) sequence, LGTIPG (SEQ ID NO: 6) sequence, RNIAEIIKDI (SEQ ID NO: 7) sequence, IKVAV (SEQ ID NO: 8) sequence, LRE sequence, DGEA (SEQ ID NO: 9) sequence, and HAV sequence, indicated by single letter codes for amino acids) peptide", [2] "amination or cationization of matrix surface", and [3] "plasma treatment or corona discharge-based hydrophilic treatment of matrix surface" may be used as specific methods.

The type of the polypeptide is not particularly limited as long as it has biocompatibility. The polypeptide is preferably, for example, gelatin, collagen, elastin, fibronectin, ProNectin, laminin, tenascin, fibrin, fibroin, entactin, thrombospondin, or RetroNectin, most preferably gelatin, collagen, or atelocollagen. Natural gelatin or a recombinant peptide is preferable as gelatin for use in the present invention. A recombinant peptide is more preferable. In this context, the natural gelatin means gelatin formed from naturally derived collagen. The recombinant peptide will be described later in the present specification.

The hydrophilicity value "1/IOB" value of the polymer having biocompatibility used in the present invention is preferably 0 to 1.0, more preferably 0 to 0.6, further preferably 0 to 0.4. IOB is an index for hydrophilicity and hydrophobicity based on the organic conception diagram representing the polarity/non-polarity of organic compounds proposed by Atsushi Fujita. The details thereof are described in, for example, "Pharmaceutical Bulletin", vol. 2, 2, pp. 163-173 (1954), "Journal of Japanese Chemistry" vol. 11, 10, pp. 719-725 (1957), and "Fragrance Journal", vol. 50, pp. 79-82 (1981). In short, this process involves assuming that methane ($CH_4$) is the source of all organic compounds and all of the other compounds are methane derivatives, selecting a certain numerical value for each of the number of carbon atoms, substituents, modified moieties, rings, and the like thereof, adding the scores to determine an organic value (OV) and an inorganic value (IV), and plotting this value on a diagram with the organic value on the X axis and the inorganic value on the Y axis. IOB on the organic conception diagram refers to the ratio of the inorganic value (IV) to the organic value (OV), i.e., "inorganic value (IV)/organic value (OV)", on the organic conception diagram. For the details of the organic conception diagram, see "Shinban Yuuki Gainenzu—Kiso to Ouyou—(New Edition, The Organic Conceptual Diagram, its Fundamentals and Applications in English)", (Yoshio Koda et al., Sankyo Publishing Co., Ltd., 2008)". In the present specification, hydrophilicity and hydrophobicity are indicated by "1/IOB" values, reciprocals of IOB. This notation represents that the smaller the "1/IOB" value becomes (the more the "1/IOB" value approaches 0), the more hydrophilic it is.

The "1/IOB" value of the polymer used in the present invention is set to within the range described above, whereby hydrophilicity is enhanced and water absorbability is enhanced. The resulting polymer is presumed to effectively act on retention of nutrients and, as a result, contribute to cell stabilization and viability in the three-dimensional cell construct (mosaic cell mass) of the present invention.

In the case where the polymer having biocompatibility used in the present invention is polypeptide, its index for hydrophilicity and hydrophobicity indicated by Grand average of hydropathicity (GRAVY) values is preferably from −9.0 to 0.3, more preferably from −7.0 to 0.0. The Grand average of hydropathicity (GRAVY) value can be obtained by the methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)".

The GRAVY value of the polymer used in the present invention is set to within the range described above, whereby hydrophilicity is enhanced and water absorbability is enhanced. The resulting polymer is presumed to effectively act on retention of nutrients and, as a result, contribute to cell stabilization and viability in the three-dimensional cell construct (mosaic cell mass; cell mass exhibiting a mosaic pattern) of the present invention.

(1-2) Cross-linking

The polymer material having biocompatibility used in the present invention may be cross-linked or may not be cross-linked. Those cross-linked are preferable. A method known in the art, such as thermal cross-linking, chemical cross-linking, cross-linking using an aldehyde (e.g., formaldehyde and glutaraldehyde), cross-linking using a condensing agent (carbodiimide, cyanamide, etc.), enzymatic cross-linking, photo-crosslinking, UV cross-linking, hydrophobic interaction, hydrogen bond, or ionic interaction can be used as a cross-linking method. A cross-linking method using glutaraldehyde or a thermal cross-linking method is preferable.

Examples of the photocrosslinking include those based on light irradiation of a polymer containing a photoreactive group introduced therein, or light irradiation in the presence of a photosensitizer. Examples of the photoreactive group include a cinnamyl group, a coumarin group, a dithiocarbamyl group, a xanthene dye, and camphorquinone.

In the case of performing cross-linking using an enzyme, the enzyme is not particularly limited as long as it has the effect of cross-linking between polymer materials. The cross-linking can be performed using preferably transglutaminase and laccase, most preferably transglutaminase. Specific examples of proteins that may be subjected to enzymatic cross-linking with transglutaminase are not particularly limited as long as they are proteins having a lysine residue and a glutamine residue. The transglutaminase may be derived from a mammal or may be derived from a microbe. Specific examples thereof include ACTIVA series manufactured by Ajinomoto Co., Inc., mammal-derived transglutaminase sold as reagents, for example, guinea pig liver-derived transglutaminase, goat-derived transglutaminase, and rabbit-derived transglutaminase manufactured by Oriental Yeast Co., ltd., Upstate USA Inc., or Biodesign International, and human-derived blood coagulation factor (Factor XIIIa, Haematologic Technologies, Inc.).

The cross-linking of the polymer material involves two steps: the step of mixing a polymer material solution with a cross-linking agent and the step of reacting the resulting solution.

In the present invention, the mixing temperature for the treatment of polymer materials with a cross-linking agent is not particularly limited as long as the solution can be mixed. The temperature is preferably 0° C. to 100° C., more preferably 0° C. to 40° C., further preferably 0° C. to 30° C., further preferably 3° C. to 25° C., further preferably 3° C. to 15° C., further preferably 3° C. to 10° C., particularly preferably 3° C. to 7° C.

The temperature can be raised for the step of reacting the polymer materials with the cross-linking agent. The reaction temperature is not particularly limited as long as the cross-linking proceeds. In consideration of the denaturation or degradation of the polymer materials, the temperature is substantially −100° C. to 200° C., more preferably 0° C. to 60° C., more preferably 0° C. to 40° C., further preferably 3° C. to 25° C., further preferably 3° C. to 15° C., further preferably 3° C. to 10° C., particularly preferably 3° C. to 7° C.

Even if the cross-linking agent is not used, the cross-linking of the polymer material can also be performed. Specific examples of the cross-linking method include, but not particularly limited to, a thermal cross-linking method.

The reaction temperature for the cross-linking method without using the cross-linking agent is not particularly limited as long as the cross-linking can be performed. The temperature is preferably −100° C. to 500° C., more preferably 0° C. to 300° C., further preferably 50° C. to 300° C., further preferably 100° C. to 250° C., further preferably 120° C. to 200° C.

(1-3) Recombinant Peptide

The recombinant peptide according to the present invention means a polypeptide or a protein-like substance that is prepared by a gene recombination technique and has an amino acid sequence similar to gelatin. For the recombinant peptide that can be used in the present invention, it is preferred to have repeats of the sequence represented by Gly-X-Y (X and Y each independently represent any amino acid) characteristic of collagen (a plurality of Gly-X-Y sequences may be the same as or different from each other). Preferably, two or more sequences of cell adhesion signals are contained in a molecule. A recombinant peptide having an amino acid sequence derived from a partial amino acid sequence of collagen can be used as the recombinant peptide used in the present invention. For example, those described in EP1014176, U.S. Pat. No. 6,992,172, WO2004/85473, and WO2008/103041 can be used, though the recombinant peptide is not limited to them. A preferable recombinant peptide used in the present invention is a recombinant peptide having the following aspect:

The recombinant peptide used in the present invention is excellent in biocompatibility based on the original performance of natural gelatin, is free from concerns about BSE or the like because of being not naturally derived, and is also excellent in non-infectious properties. Moreover, since the recombinant peptide used in the present invention is homogeneous compared with natural one and its sequence is determined, it can be designed precisely with a little variation in strength or degradability depending on cross-linking or the like described later.

The molecular weight of the recombinant peptide is preferably from 2 KDa to 100 KDa, more preferably from 2.5 KDa to 95 KDa, further preferably from 5 KDa to 90 KDa, most preferably from 10 KDa to 90 KDa.

The recombinant peptide has repeats of the sequence represented by Gly-X-Y characteristic of collagen. In this context, a plurality of Gly-X-Y sequences may be the same as or different from each other. In Gly-X-Y, Gly represents glycine, and X and Y each represent any amino acid (preferably, any amino acid other than glycine). The GXY sequence characteristic of collagen is a very specific partial structure in the amino acid composition and sequence of gelatin/collagen, compared with other proteins. In this moiety, glycine accounts for approximately ⅓ of the whole and appears at a rate of one out of three amino acids in the amino acid sequence. Glycine is the simplest amino acid. Its position in the molecular chain is less restricted, and glycine makes a significant contribution to the regeneration of the helix structure during gelatinization. It is preferred that imino acids (proline or oxyproline) should be included in large amounts in the amino acids represented by X and Y and account for 10% to 45% of all the amino acids. It is preferred that preferably 80% or more, more preferably 95% or more, most preferably 99% or more of the amino acids in the sequence should form the GXY repeat structures.

In general gelatin, of polar amino acids, those having an electric charge and those uncharged are present at a 1:1 ratio. In this context, the polar amino acids specifically refer to cysteine, aspartic acid, glutamic acid, histidine, lysine, asparagine, glutamine, serine, threonine, tyrosine, and arginine. Of them, polar uncharged amino acids refer to cysteine, asparagine, glutamine, serine, threonine, and tyrosine. The ratio of the polar amino acids is 10 to 40%, preferably 20 to 30%, to all amino acids constituting the recombinant peptide used in the present invention. In addition, it is preferred that the ratio of uncharged amino acids to the polar amino acids should be from 5% to less than 20%, preferably less than 10%. It is further preferred that of serine, threonine, asparagine, tyrosine and cysteine, any one amino acid, preferably two or more amino acids, should not be contained in the sequence.

In general, minimal ammo acid sequences that function as cell adhesion signals in polypeptides are known (e.g., "Medicina Philosophica", Vol. 9, No. 7 (1990), p. 527, Nagai Shoten Co., Ltd.). It is preferred that the recombinant peptide used in the present invention should have two or more of these cell adhesion signals in a molecule. Specific sequences are preferably RGD sequences, LDV sequences, REDV (SEQ ID NO: 2) sequences, YIGSR (SEQ ID NO: 3) sequences, PDSGR (SEQ ID NO: 4) sequences, RYVVLPR (SEQ ID NO: 5) sequences, LGTIPG (SEQ ID NO: 6) sequences, RNIAEIIKDI (SEQ ID NO: 7) sequences, IKVAV (SEQ ID NO: 8) sequences, LRE sequences, DGEA (SEQ ID NO: 9) sequences, and HAV sequences, more preferably RGD sequences, YIGSR (SEQ ID NO: 3) sequences, PDSGR (SEQ ID NO: 4) sequences, LGTIPG (SEQ ID NO: 6) sequences, IKVAV (SEQ ID NO: 8) sequences, and HAV sequences, particularly preferably RGD sequences, indicated by single letter codes for amino acids, in terms of many types of adhesive cells. Of the RGD sequences, an ERGD (SEQ ID NO: 10) sequence is preferable. The amount of substrates produced by the cells can be improved by using the recombinant peptide having cell adhesion signals. In the case of, for example, chondrogenic differentiation using mesenchymal stem cells as the cells, the production of glycosaminoglycan (GAG) can be improved.

For the arrangement of the RGD sequences in the recombinant peptide used in the present invention, it is preferred that the number of amino acids between the RGD sequences should be between 0 and 100, preferably between 25 and 60, and should not be uniformly determined.

From the viewpoint of cell adhesion/growth, the content of this minimal amino acid sequence is preferably 3 to 50 sequences, more preferably 4 to 30 sequences, particularly preferably 5 to 20 sequences, most preferably 12 sequences, per protein molecule.

In the recombinant peptide used in the present invention, the ratio of the RGD motifs to the total number of the amino acids is preferably at least 0.4%. In the case where the recombinant peptide contains 350 or more amino acids, it is preferred that each stretch of 350 amino acids should contain at least one RGD motif. The ratio of the RGD motifs to the total number of the amino acids is more preferably at least 0.6%, further preferably at least 0.8%, further preferably at least 1.0%, further preferably at least 1.2%, most preferably at least 1.5%. The number of the RGD motifs within the recombinant peptide is preferably at least 4, more preferably 6, further preferably 8, further preferably from 12 to 16, per 250 amino acids. The ratio of the RGD motifs of 0.4% corresponds to at least one RGD sequence per 250 ammo acids. Since the number of the RGD motifs is an integer, gelatin consisting of 251 amino acids must contain at least two RGD sequences in order to satisfy the feature of 0.4%. Preferably, the recombinant peptide of the present invention contains at least two RGD sequences per 250 amino acids, more preferably at least three RGD sequences per 250 amino acids, further preferably at least four RGD sequences per 250 amino acids. In a further aspect, the recombinant peptide of the present invention comprises at least 4 RGD motifs, preferably 6, more preferably 8, further preferably 12 to 16 RGD motifs.

Moreover, the recombinant peptide may be partially hydrolyzed.

It is preferred that the recombinant peptide used in the present invention should have repeat structures represented by A[(Gly-X-Y)n]mB. m is preferably 2 to 10, more preferably 3 to 5. n is preferably 3 to 100, more preferably 15 to 70, most preferably 50 to 65.

It is preferred that a plurality of naturally occurring collagen sequence units should be bonded to form repeat units. In this context, the naturally occurring collagen may be any naturally occurring collagen and is preferably type-I, type-II, type-III, type-IV, and type-V collagens, more preferably type-I, type-II, and type-III collagens. In another embodiment, the origin of the collagen is preferably a human, cattle, a pig, a mouse, or a rat, more preferably a human.

The isoelectric point of the recombinant peptide used in the present invention is preferably 5 to 10, more preferably 6 to 10, further preferably 7 to 9.5.

Preferably, the recombinant peptide is not deaminated.

Preferably, the recombinant peptide does not have telopeptide.

Preferably, the recombinant peptide is a material for substantially pure collagen prepared from a nucleic acid encoding natural collagen.

The recombinant peptide used in the present invention is particularly preferably a recombinant peptide having:
(1) the amino acid sequence represented by SEQ ID NO: 1; or
(2) an amino acid sequence having 80% or higher (more preferably 90% or higher, most preferably 95% or higher) homology to the amino acid sequence represented by SEQ ID NO: 1 and having biocompatibility.

The recombinant peptide used in the present invention can be produced by a gene recombination technique known by those skilled in the art and can be produced according to a method described in, for example, EP1014176A2, U.S. Pat. No. 6,992,172, WO2004-85473, or WO2008/103041. Specifically, a gene encoding the amino acid sequence of the predetermined recombinant peptide is obtained, and this is incorporated in an expression vector to prepare a recombinant expression vector, which is then introduced in appropriate hosts to prepare transformants. The obtained transformants are cultured in an appropriate medium, whereby the recombinant peptide is produced. Thus, the produced recombinant peptide can be collected from the cultures to prepare the recombinant peptide used in the present invention.

(1-4) Polymer Blocks Having Biocompatibility

In the present invention, blocks containing the above-described polymer material having biocompatibility are used. A production method for the polymer blocks is not particularly limited. For example, solid matter consisting of the polymer can be pulverized using a pulverizer (New Power Mill, etc.) and then sized through a sieve to obtain a block having the desired size.

The size of each polymer block is preferably from 1 µm to 700 µm, more preferably from 10 µm to 700 µm, further preferably from 10 µm to 300 µm, further preferably from 20 µm to 150 µm, particularly preferably from 25 µm to 106 µm. Moreover, the polymer block may be in a long string-like form equal to or longer than 700 µm having a thickness in the size range described above and may be in a sheet or gel form having a thickness in the size range described above. The cells can be more uniformly present in the construct by adopting this preferable range.

It is also preferred that the cell construct for cell transplantation of the present invention should further comprise an angiogenesis factor. In this context, examples of the angiogenesis factor can preferably include basic fibroblast growth factor (bFGF), vascular endothelial growth factor (VEGF), and hepatocyte growth factor (HGF). A method for producing the cell construct for cell transplantation comprising an angiogenesis factor is not particularly limited. For example, this cell construct can be produced by using polymer blocks impregnated with an angiogenesis factor.

(2) Cells

The cells used in the present invention can be used appropriately as long as they permit cell transplantation, which is the purpose of the cell construct of the present invention. The type thereof is not particularly limited. Moreover, the cells used may be of one type, or a combination of a plurality of types may be used. Furthermore, the cells used are preferably animal cells, more preferably vertebrate-derived cells, particularly preferably human-derived cells. The type of the vertebrate-derived cells (particularly, human-derived cells) may be any of pluripotent cells, somatic stem cells, precursor cells, and mature cells. For example, ES cells, GS cells, or iPS cells can be used as pluripotent cells. For example, mesenchymal stem cells (MSCs), hematopoietic stem cells, amnion cells, cord blood cells, bone marrow-derived cells, cardiac muscle stem cells, fat-derived stem cells, or neural stem cells can be used as somatic stem cells. For example, cells derived from the skin, dermis, epidermis, muscle, cardiac muscle, nerve, bone, cartilage, endothelium, brain, epithelium, heart, kidney, liver, pancreas, spleen, oral cavity, cornea, bone marrow, cord blood, amnion, or hair can be used as precursor cells and mature cells. For example, ES cells, iPS cells, MSCs, cartilage cells, osteoblasts, osteoprogenitor cells, mesenchyme cells, myoblasts, cardiac muscle cells, cardiac myoblasts, nerve cells, hepatic cells, beta cells, fibroblasts, corneal endothelial cells, vascular endothelial cells, corneal epithelial cells, amnion cells, cord blood cells, bone marrow-derived cells, or hematopoietic stem cells can be used as human-derived cells. Moreover, the origin of the cells may be any of autologous cells and heterologous cells.

Examples of cells suitable for heat diseases such as severe heart failure and severe myocardial infarction can preferably include autologously or heterologously extracted cardiac muscle cells, smooth muscle cells, fibroblasts, skeletal muscle-derived cells (particularly, satellite cells), and bone marrow cells (particularly, bone marrow cells differentiated into cardiac muscle-like cells). Furthermore, cells to be transplanted can be selected appropriately for other organs. Preferable examples thereof can include transplantation of neural precursor cells or cells capable of being differentiated into nerve cells into a cerebral ischemia/cerebral infarction site, and transplantation of vascular endothelial cells or cells capable of being differentiated into vascular endothelial cells into a myocardial infarction/skeletal muscle ischemia site.

Further examples of the cells include cells for use in cell transplantation for diabetic organ damage. Specific examples thereof include cells for a cell transplantation treatment method variously studied on diseases such as kidney diseases, pancreas diseases, peripheral nerve diseases, eye diseases, or hematogenous disorder in the extremities. Specifically, an attempt to transplant insulin-secreting cells to the pancreas having the reduced ability to secrete insulin, transplantation of bone marrow-derived cells for hematogenous disorder in the extremities, or the like has been studied, and such cells can be used.

The cell construct for cell transplantation of the present invention comprising non-vascular cells can be used preferably. Moreover, the cell construct for cell transplantation of the present invention containing only non-vascular cell as its constituent cells can also be used preferably. The cell construct for cell transplantation of the present invention containing only non-vascular cells as the cells is capable of forming blood vessels at its transplantation site after transplantation. Furthermore, in the case where the cell construct for cell transplantation of the present invention contains two or more types of constituent cells comprising both non-vascular cells and vascular cells, this cell construct is more capable of forming blood vessels and thus more preferable than the cell construct containing only non-vascular cells as the constituent cells.

Furthermore, in the case where the cell construct for cell transplantation of the present invention contains two or more types of constituent cells and has a region wherein the volume of the vascular cells in the central portion of the cell construct is larger than the volume of the vascular cells in the peripheral portion, this cell construct is much more capable of forming blood vessels and thus much more preferable. The phrase "has a region wherein the volume of the vascular cells in the central portion of the cell construct is larger than the volume of the vascular cells in the peripheral portion" specifically refers to that, when slice samples having a thickness of 2 μm are prepared, there is a sample having a region as defined above. In this context, the central portion of the cell construct refers to a volume corresponding to a distance up to 80% from the center in the distance from the center to the surface of the cell construct. The peripheral portion of the cell construct refers to a volume from the position of 80% from the center to the surface of the construct. In this context, the central portion of the cell construct is defined as follows:

With regard to any cross section that passes the center of the cell construct, a radius X is determined such that, when the center of a circle with the radius X is moved around the cross section along with the external margin of the cross section, the area of a portion except for the overlap between the moved circle and the cross section accounts for 64% of the cross-sectional area of the cross section. The center of a circle with the determined radius X is moved therearound, and a portion except for the overlap between the moved circle and the cross section is defined as the central portion of the cell construct. At this time, the cross section which gives largest cross-section area is most preferable. As to the center of the cell construct, with regard to the cross section which gives largest cross-section area, a radius Y is determined such that, when the center of a circle with the radius Y is moved around the cross section along with the external margin of the cross section, the area of a portion except for the overlap between the moved circle and the cross section becomes one point. The center of a circle with the determined radius Y is moved therearound, and one point except for the overlap between the moved circle and the cross section is defined as the center of the cell construct. When the area does not become one point, and becomes a line segment, or when there are plural such line segments, the middle point of each such line segment is defined as the center.

Specifically, the cell construct preferably has a region wherein the ratio of the vascular cells in the central portion is preferably 60% to 100%, more preferably 65% to 100%, further preferably 80% to 100%, further preferably 90% to 100%, to the whole area of the vascular cells. The phrase "has a region wherein the ratio of the vascular cells in the central portion is 60% to 100% to the whole area of the vascular cells" specifically refers to that, when slice samples having a thickness of 2 μm are prepared, there is a sample having a region having the ratio as defined above. Blood vessel formation can be further promoted by adopting this range.

In this context, the ratio of the vascular cells in the central portion can be determined, for example, by: staining vascular cells to be assayed when a thin section sample is prepared; determining an average value of the color density (strength) of the central portion using image processing software ImageJ; calculating area×strength for the central portion; further determining an average value of color density (strength) as a whole; calculating area×strength as a whole; and determining the ratio of the value of area×strength for the central portion to the value of area×strength as a whole. In this context, a staining method known in the art can be used appropriately as a method for staining the vascular cells. For example, in the case of using hECFCs as the cells, an anti-CD31 antibody can be used.

It is also preferred that the cell construct should have a region in which the density of the vascular cells in the central portion is $1.0 \times 10^{-4}$ cells/μm$^3$ or more. It is more preferred that the whole central portion of the cell construct should have the cell density described above. In this context, the phrase "have a region in which the density is $1.0 \times 10^{-4}$ cells/μm$^3$ or more" specifically means that there is a sample having the region with the density as mentioned above, when section samples having a thickness of 2 μm are prepared. The cell density is more preferably $1.0 \times 10^{-4}$ to $1.0 \times 10^{-3}$ cells/μm$^3$, further preferably $1.0 \times 10^{-4}$ to $2.0 \times 10^{-4}$ cells/μm$^3$, further preferably $1.1 \times 10^{-4}$ to $1.8 \times 10^{-4}$ cells/μm$^3$, further preferably $1.4 \times 10^{-4}$ to $1.8 \times 10^{-4}$ cells/μm$^3$. Blood vessel formation can be further promoted by adopting this range.

In this context, the density of the vascular cells in the central portion can be determined by actually counting the number of cells in a thin section sample and dividing the number of cells by volume. In this context, the central portion is defined as follows: it is defined as a portion obtained by cutting out a portion corresponding to the thickness of the thin section sample in the perpendicular direction in the central portion described above. In order to determine the cell density, the number of the vascular cells in the central portion can be calculated, for example, by superimposing a thin section sample in which the vascular cells to be assayed have been stained and a thin section sample in which cell nuclei have been stained and counting the number of overlapping cell nuclei, and the volume can be determined by determining the area of the central portion using ImageJ and multiplying the area by the thickness of the thin section sample.

In the present specification, the vascular cells mean cells related to blood vessel formation and include cells constituting blood vessels or blood, and precursor cells or somatic stem cells capable of being differentiated into these cells. In this context, the vascular cells do not include pluripotent cells such as ES cells, GS cells, or iPS cells, or cells that are not spontaneously differentiated into cells constituting blood vessels or blood, such as mesenchymal stem cells (MSC). The vascular cells are preferably cells constituting blood vessels. Examples of the cells constituting blood vessels among vertebrate-derived cells (particularly, human-derived cells) can preferably include vascular endothelial cells and vascular smooth muscle cells. The vascular endothelial cells include both venous endothelial cells and arterial endothelial cells. Vascular endothelial precursor cells can be used as precursor cells for the vascular endothelial cells. Vascular endothelial cells and vascular endothelial precursor cells are preferable. Blood cells can be used as cells constituting blood, and white blood cells such as lymphocytes or neutrophils, monocytes, or hematopoietic stem cells as their stem cells can be used. Moreover, in the present specification, the non-vascular cells mean cells other than the vascular cells described above. For example, ES cells, iPS cells, mesenchymal stem cells (MSCs), cardiac muscle stem cells, cardiac muscle cells, fibroblasts, myoblasts, cartilage cells, myoblasts, hepatic cells, or nerve cells can be used. Preferably, mesenchymal stem cells (MSCs), cartilage cells, myoblasts, cardiac muscle stem cells, cardiac muscle cells, hepatic cells, or iPS cells can be used. Mesenchymal stem cells (MSCs), cardiac muscle stem cells, cardiac muscle cells, or myoblasts are more preferable.

The cell construct for cell transplantation of the present invention encompasses those in which blood vessels have been formed using the cell construct for cell transplantation of the present invention wherein the cells are of two or more types comprising both non-vascular cells and vascular cells. Moreover, in this context, the preferable ranges of the "cell construct for cell transplantation of the present invention wherein the cells are of two or more types comprising both non-vascular cells and vascular cells" are as described above. Examples of a method for constructing blood vessels include a method involving bonding a cell sheet containing a vascular cell mixture to a gel material of which a piece for a blood vessel moiety has been hollowed out in a tunnel shape, and culturing the cell sheet while flowing a culture solution to the tunnel. Alternatively, vascular cells may be sandwiched between cell sheets to construct blood vessels.

(3) Cell Construct

In the present invention, the above-described polymer blocks having biocompatibility and the above-described cells are used, and the plural polymer blocks are three-dimensionally arranged in spaces between the plural cells in a mosaic pattern, whereby the cell construct can have a thickness suitable for cell transplantation. In addition, the polymer blocks having biocompatibility and the cells are three-dimensionally arranged in a mosaic pattern, whereby a three-dimensional cell construct in which the cells are uniformly present can be formed to enable nutrition delivery into the three-dimensional cell construct from outside. As a result, when cell transplantation is performed using the cell construct for cell transplantation of the present invention, transplantation with the necrosis of the transplanted cells prevented can be achieved. In this context, the "prevention of necrosis" means that the degree of necrosis is low compared with the case where only the cells are transplanted without being contained in the cell construct of the present invention.

The thickness or diameter of the cell construct for cell transplantation of the present invention can be set to the desired thickness by a method described later in the present specification and is preferably 215 µm or larger, more preferably 400 µm or larger, most preferably 730 µm or larger, in terms of the lower limit. The upper limit of the thickness or diameter is not particularly limited and is preferably 3 cm or smaller, more preferably 2 cm or smaller, further preferably 1 cm or smaller, in terms of a general range in use. Moreover, the range of the thickness or diameter of the cell construct is preferably from 400 µm to 3 cm, more preferably from 500 µm to 2 cm, further preferably from 720 µm to 1 cm. In Examples, 720 µm or larger cell constructs (FIG. 3) were prepared and then fused to prepare a cell construct having a thickness of 813 µm (FIG. 10). A feature of the cell construct for cell transplantation of the present invention is that regions consisting of the polymer blocks and regions consisting of the cells are arranged in a mosaic pattern. In the present specification, the "thickness or diameter of the cell construct" represents the following: when a certain point A in the cell construct is selected, the length of a line segment that is located on a straight line passing through the point A and partitions the cell construct to give the shortest distance between the cell construct and the outside world is defined as a line segment A. The point A is selected such that the line segment A becomes longest in the cell construct. The length of this longest line segment A is defined as the "thickness or diameter of the cell construct".

Moreover, in the case of using the cell construct of the present invention as a cell construct before fusion or as a cell construct before addition of second polymer blocks in a method (described later) for producing the cell construct for cell transplantation of the present invention, the range of the thickness or diameter of the cell construct is preferably from 10 µm to 1 cm, more preferably from 10 µm to 2000 µm, further preferably from 15 µm to 1500 µm, most preferably from 20 µm to 1300 µm.

In the cell construct for cell transplantation of the present invention, the ratio between the cells and the polymer blocks is not particularly limited and is preferably a ratio of the polymer blocks per cell from 0.0000001 µg to 1 µg, more preferably from 0.000001 µg to 0.1 µg, further preferably from 0.00001 µg to 0.01 µg, most preferably from 0.00002 µg to 0.006 µg. The cells can be more uniformly present by adopting the range described above. Moreover, the cells can exert effects during use in the application described above by adopting the range described above as the lower limit. Components arbitrarily present in the polymer blocks can be supplied to the cells by adopting the range described above as the upper limit. In this context, examples of the components in the polymer blocks include, but not particularly limited to, components contained in a medium described later.

(4) Method for Producing Cell Construct

The cell construct of the present invention can be produced by placing the block(s) consisting of the polymer material having biocompatibility and the cell(s) in an alternating manner. A production method is not particularly limited and is preferably a method involving forming polymer blocks and then inoculating cells thereto. Specifically, the cell construct of the present invention can be produced by incubating a mixture of the polymer blocks having biocompatibility and a culture solution containing the cells. For example, the cells and the polymer blocks having biocompatibility prepared in advance are arranged in a mosaic pattern in a container or in a liquid retained in a container. Means of this arrangement is preferably use of natural aggregation, free fall, centrifugation, or stirring to promote or control the sequence formation of the mosaic pattern consisting of the cells and the biocompatible matrices.

The container used is preferably a container made of a low cell-adhesive material or a non-cell-adhesive material, more preferably a container made of polystyrene, polypropylene, polyethylene, glass, polycarbonate, or polyethylene terephthalate. It is preferred that the container should have a flat, U-shaped, or V-shaped bottom.

The mosaic-pattern cell construct obtained by the method described above can be produced into a cell construct having the desired size by a method, for example,
(1) fusing separately prepared mosaic-pattern cell masses with each other, or
(2) increasing the volume thereof under a differentiation medium or growth medium.
A method for this fusion or increase in volume is not particularly limited.

For example, in the step of incubating a mixture of the polymer blocks having biocompatibility and a culture solution containing the cells, the medium is replaced by a differentiation medium or growth medium, whereby the volume of the cell construct can be increased. Preferably, in the step of incubating a mixture of the polymer blocks having biocompatibility and a culture solution containing the cells, additional polymer blocks having biocompatibility can be added thereto to produce a cell construct of the desired size in which the cells are uniformly present.

The method involving fusing separately prepared mosaic-pattern cell masses with each other is specifically a method for producing the cell construct which comprises the step of fusing cell constructs with each other, the cell constructs each comprising plural polymer blocks having biocompatibility and plural cells, wherein one or more of the polymer blocks are placed in each of some or all of spaces formed by the plural cells.

The preferable ranges of the "polymer blocks (type, size, etc.) having biocompatibility", the "cells", the "spaces between the cells", the "obtained cell construct (size, etc.)", the "ratio between the cells and the polymer blocks", and the like according to the method for producing the cell construct of the present invention are similar to the preferable ranges relating to the cell construct of the present invention described above.

Moreover, the thickness or diameter of each cell construct before the fusion is preferably from 10 µm to 1 cm, and the thickness or diameter after the fusion is preferably from 400 µm to 3 cm. In this context, the thickness or diameter of each cell construct before the fusion is more preferably from 10 µm to 2000 µm, further preferably from 15 µm to 1500 µm, most preferably from 20 µm to 1300 µm, and the range of the thickness or diameter after the fusion is more preferably from 500 µm to 2 cm, further preferably from 720 µm to 1 cm.

The above-described method for producing the cell construct of the desired size by adding thereto additional polymer blocks having biocompatibility is specifically a method for producing the cell construct which comprises the steps of further adding second polymer blocks to a cell construct and incubating them, the cell construct comprising plural first polymer blocks having biocompatibility and plural cells, wherein one or more of the polymer blocks are placed in each of some or all of plural spaces formed by the plural cells. In this context, the preferable ranges of the "polymer blocks (type, size, etc.) having biocompatibility", the "cells", the "spaces between the cells", the "obtained cell construct (size, etc.)", the "ratio between the cells and the polymer blocks", and the like are similar to the preferable ranges relating to the cell construct of the present invention described above.

In this context, it is preferred that the cell constructs to be fused should be placed at a spacing from 0 to 50 µm, more preferably from 0 to 20 µm, further preferably from 0 to 5 µm. In the fusion of the cell constructs, the cells or substrates produced by the cells are considered to function as an adhesive by cell growth/spreading to connect the cell constructs. The adhesion between the cell constructs can be facilitated by adopting the range described above.

The size of each first polymer block according to the present invention is preferably from 1 µm to 700 µm, more preferably from 10 µm to 700 µm, further preferably from 10 µm to 300 µm, further preferably from 20 µm to 150 µm, particularly preferably from 25 µm to 106 µm. Moreover, the size of each second polymer block according to the present invention is also preferably from 1 µm to 700 µm, more preferably from 10 µm to 700 µm, further preferably from 10 µm to 300 µm, further preferably from 20 µm to 150 µm, particularly preferably from 25 µm to 106 µm.

The range of the thickness or diameter of the cell construct obtained by the method for producing the cell construct of the present invention is preferably from 400 µm to 3 cm, more preferably from 500 µm to 2 cm, further preferably from 720 µm to 1 cm.

For further adding second polymer blocks to the cell construct and incubating them, it is preferred that the pace at which the second polymer blocks are added should be selected appropriately according to the growth rate of the cells used. Specifically, if the second polymer blocks are added at a fast pace, the cells are moved toward the outer region of the cell construct to reduce uniform cell distribution. If they are added at a slow pace, sites with a high ratio of the cells are formed to reduce uniform cell distribution. Thus, the pace is selected in consideration of the growth rate of the cells used.

When cell transplantation is performed using the cell construct for cell transplantation of the present invention containing no vascular cell, even this cell construct for cell transplantation of the present invention, as described above, is capable of forming blood vessels at the transplantation site after transplantation. In the case of comprising both non-vascular cells and vascular cells, the cell construct is more capable of forming blood vessels than the cell construct containing only non-vascular cells as the constituent cells.

Examples of the method for producing the cell construct comprising both non-vascular cells and vascular cells can preferably include production methods (1) to (3) described below.

The production method (1) comprises the steps of forming a cell construct by the method described above using non-vascular cells and then adding vascular cells and polymer blocks thereto. In this context, the "step of vascular cells and polymer blocks" encompasses both of the method involving fusing prepared mosaic-pattern cell masses with each other and the method involving increasing the volume thereof under a differentiation medium or growth medium. This method enables production of (i) a cell construct in which the non-vascular cells are present in a larger area compared with the vascular cells in the central portion of the cell construct while the vascular cells are present in a larger area compared with the non-vascular cells in the peripheral portion, (ii) a cell construct for cell transplantation in which the area of the non-vascular cells in the central portion of the cell construct is larger than the area of the non-vascular cells in the peripheral portion, and (iii) a cell construct for cell transplantation in which the area of the vascular cells in the central portion of the cell construct is smaller than the area of the vascular cells in the peripheral portion.

The production method (2) comprises the steps of forming a cell construct by the method described above using vascular cells and then adding non-vascular cells and polymer blocks thereto. In this context, the "step of non-vascular cells and polymer blocks" encompasses both of the method involving fusing prepared mosaic-pattern cell masses with each other and the method involving increasing the volume thereof under a differentiation medium or growth medium. This method enables production of (i) a cell construct in which the vascular cells are present in a larger area compared with the non-vascular cells in the central portion of the cell construct while the non-vascular cells are present in a larger area compared with the vascular cells in the peripheral portion, (ii) a cell construct for cell transplantation in which the area of the vascular cells in the central portion of the cell construct is larger than the area of the vascular cells in the peripheral portion, and (iii) a cell construct for cell transplantation in which the area of the non-vascular cells in the central portion of the cell construct is smaller than the area of the non-vascular cells in the peripheral portion.

The production method (3) involves substantially simultaneously using non-vascular cells and vascular cells to form a cell construct by the method described above. This method enables production of a cell construct in which neither non-vascular cells nor vascular cells are largely maldistributed at any site of the cell construct.

From the viewpoint of forming blood vessels at a transplantation site after transplantation, it is preferred to be a cell construct in which the vascular cells are present in a larger area compared with the non-vascular cells in the central portion of the cell construct while the non-vascular cells are present in a larger area compared with the vascular cells in the peripheral portion, or a cell construct for cell transplantation in which the area of the vascular cells in the central portion is larger than the area of the vascular cells in the peripheral portion. Blood vessel formation can be further promoted by adopting such cell construct. The cell construct in which the number of the cells present in the central portion is larger can further promote blood vessel formation.

For similar reasons, the production method comprising the steps of forming a cell construct using vascular cells and then adding thereto non-vascular cells and polymer blocks is preferable. For the production method, it is further preferred that the number of the vascular cells should be increased.

The cell construct for cell transplantation of the present invention can be used for the purpose of cell transplantation at a diseased site in, for example, heart diseases such as severe heart failure and severe myocardial infarction, and cerebral ischemia/cerebral infarction. The cell construct can also be used for diseases such as diabetic kidney diseases, pancreas diseases, peripheral nerve diseases, eye diseases, or hematogenous disorder in the extremities. For example, incision, injection, or endoscopy may be used as a transplantation method. The cell construct of the present invention may be transplanted by a low invasive method such as transplantation by injection, because the size of the construct, unlike cell transplants such as cell sheets, can be decreased.

Moreover, the cell transplantation method of the present invention comprises using a cell construct for cell transplantation, which is the cell construct for cell transplantation of the present invention, comprising polymer blocks having biocompatibility and cells of at least one type, wherein the plural polymer blocks are placed in spaces between the plural cells. The preferable ranges of the cell construct for cell transplantation are as described above.

The cell aggregate for cell transplantation of the present invention is a cell aggregate for cell transplantation comprising non-vascular cells and vascular cells, wherein the cell aggregate for cell transplantation satisfies at least one of the requirements:

(1) the cell aggregate has a region wherein the volume of the vascular cells in the central portion of the cell aggregate is larger than the volume of the vascular cells in the peripheral portion, and
(2) the cell aggregate has a region in which the density of the vascular cells in the central portion is $1.0 \times 10^{-4}$ cells/$\mu m^3$ or more.

In this context, the cell aggregate for cell transplantation according to the present invention refers to a cell transplant comprising cells as constituents and is not intended to exclude those containing the other components. The cell aggregate for cell transplantation of the present invention may contain the polymer blocks used for the cell construct of the present invention or may not contain the polymer blocks used for the cell construct of the present invention.

Examples of the shape of the cell aggregate can preferably include, but not particularly limited to, a sheet-like shape and a spherical mass. It can be exemplified specifically by a cell sheet, layered product of plural cell sheets, a cell mass (spheroid), and fused product of plural cell masses.

Moreover, the non-vascular cells and the vascular cells are as described above.

The central portion of the cell aggregate refers to an area corresponding to a distance up to 80% from the center in the distance from the center to the surface of the cell aggregate. The peripheral portion of the cell aggregate refers to an area from the position of 80% from the center to the surface of the construct. In this context, the central portion of the cell aggregate is defined as follows:

With regard to any cross section that passes the center of the cell construct, a radius X is determined such that, when the center of a circle with the radius X is moved around the cross section along with the external margin of the cross section, the area of a portion except for the overlap between the moved circle and the cross section accounts for 64% of the cross-sectional area of the cross section. The center of a circle with the determined radius X is moved therearound, and a portion except for the overlap between the moved circle and the cross section is defined as the central portion of the cell aggregate. At this time, the cross section which gives largest cross-section area is most preferable. As to the center of the cell construct, with regard to the cross section which gives largest cross-section area, a radius Y is determined such that, when the center of a circle with the radius Y is moved around the cross section along with the external margin of the cross section, the area of a portion except for the overlap between the moved circle and the cross section becomes one point. The center of a circle with the determined radius Y is moved therearound, and one point except for the overlap between the moved circle and the cross section is defined as the center of the cell construct. When the area does not become one point, and becomes a line segment, or when there are plural such line segments, the middle point of each such line segment is defined as the center.

The cell aggregate wherein the distance from the central portion determined as mentioned above to the outermost part of the cell construct is 10 μm or more, is considered as the cell aggregate of the present invention.

Specifically, the cell aggregate preferably has a region wherein the ratio of the vascular cells in the central portion is 60% to 100%, more preferably 65% to 100%, further preferably 80% to 100%, further preferably 90% to 100%, to the whole areas of the vascular cells. Blood vessel formation can be further promoted by adopting this range.

It is also preferred that the cell aggregate should have a region in which the density of the vascular cells in the central portion is $1.0 \times 10^{-4}$ cells/$\mu m^3$ or more. It is more preferred that the whole central portion of the cell aggregate should have the cell density described above. In this context, the phrase "have a region in which the density is $1.0 \times 10^{-4}$ cells/$\mu m^3$ or more" specifically refers to that that there is a sample having the region with this density when section samples having a thickness of 2 μm are prepared. The cell density is more preferably $1.0 \times 10^{-4}$ to $1.0 \times 10^{-3}$ cells/$\mu m^3$, further preferably $1.0 \times 10^{-4}$ to $2.0 \times 10^{-4}$ cells/$\mu m^3$, further preferably $1.1 \times 10^{-4}$ to $1.8 \times 10^{-4}$ cells/$\mu m^3$, further preferably $1.4 \times 10^{-4}$ to $1.8 \times 10^{-4}$ cells/$\mu m^3$. Blood vessel formation can be further promoted by adopting this range. It is preferred that the cell aggregate should satisfy both of the requirements (1) and (2).

Hereinafter, the present invention will be described more specifically with reference to Examples. However, the present invention is not intended to be limited to Examples.

EXAMPLES

Example 1

Recombinant Peptide

CBE3 described below was prepared as a recombinant peptide (described in WO2008-103041).
CBE3
Molecular weight: 51.6 kD
Structure: GAP[(GXY)63]3G
The number of amino acids: 571
The number of RGD sequences: 12
Imino acid content: 33%
Substantially 100% of amino acids are derived from the GXY repeat structures. The amino acid sequence of CBE3 does not contain any of serine, threonine, asparagine, tyrosine, and cysteine. CBE3 has an ERGD sequence.
Isoelectric point: 9.34, GRAVY value: −0.682, 1/IOB value: 0.323
Amino acid sequence (SEQ ID NO: 1 in the Sequence Listing) (same as SEQ ID NO: 3 in WO2008/103041 except that X at the end was modified to "P")

GAP (GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP) 3G

Example 2

Preparation of Recombinant Peptide Micro-blocks

Amorphous micro-blocks were prepared as matrix blocks using the recombinant peptides CBE3. 1000 mg of the recombinant peptides was dissolved in 9448 μL of ultrapure water. After addition of 152 μL of 1 N HCl, 400 μL of 25% glutaraldehyde was added thereto at a final concentration of 1.0% and reacted at 50° C. for 3 hours to prepare a cross-linked gelatin gel. This cross-linked gelatin gel was dipped in 1 L of a 0.2 M glycine solution and shaken at 40° C. for 2 hours. Then, the cross-linked gelatin gel was shake-washed for 1 hour in 5 L of ultrapure water, and the ultrapure water was replaced by fresh one, followed by washing again for 1 hour. This procedure was repeated to complete a total of 6 washing operations. The cross-linked gelatin gel thus washed was frozen at −80° C. for 5 hours and then freeze-dried in a freeze dryer (EYELA, FDU-1000). The obtained freeze-dried product was pulverized with New Power Mill (Osaka Chemical Co., Ltd., New Power Mill PM-2005). The pulverization was performed at the maximum number of revolutions for a total of 5 minutes (1 minute×5 runs). The obtained particles were sized through a stainless sieve to obtain 25 to 53 μm and 53 to 106 μm recombinant peptide micro-blocks.

Example 3

Preparation of Natural Gelatin Micro-blocks

Amorphous micro-blocks were prepared as matrix blocks using natural gelatin (Nippi, Inc., Nippi gelatin/high grade gelatin APAT). 1000 mg of the natural gelatin was dissolved in 9448 μL of ultrapure water. After addition of 152 μL of 1 N HCl, 400 μL of 25% glutaraldehyde was added thereto at a final concentration of 1.0% and reacted at 50° C. for 3 hours to prepare a cross-linked gelatin gel. This cross-linked gelatin gel was dipped in 1 L of a 0.2 M glycine solution and shaken at 40° C. for 2 hours. Then, the cross-linked gelatin gel was shake-washed for 1 hour in 5 L of ultrapure water, and the ultrapure water was replaced by fresh one, followed by washing again for 1 hour. This procedure was repeated to complete a total of 6 washing operations. The cross-linked gelatin gel thus washed was frozen at −80° C. for 5 hours and then freeze-dried in a freeze dryer (EYELA, FDU-1000). The obtained freeze-dried product was pulverized with New Power Mill (Osaka Chemical Co., Ltd., New Power Mill PM-2005). The pulverization was performed at the maximum number of revolutions for a total of 5 minutes (1 minute×5 runs). The obtained particles were sized through a stainless sieve to obtain 25 to 53 μm and 53 to 106 μm natural gelatin micro-blocks.

Example 4

Preparation of Mosaic Cell Mass Using Recombinant Peptide Micro-blocks

Human bone marrow-derived mesenchymal stem cells (hMSCs) were adjusted to 500,000 cells/mL with a growth medium (Takara Bio Inc.; MSCGM-CD™ BulletKit™). After addition of recombinant peptide micro-blocks prepared in Example 2 to be 1.0 mg/mL, 100 μL of the mixture was inoculated to a Sumilon Celltight X96U plate (Sumitomo Bakelite Co., Ltd., U-shaped bottom) and left standing for 18 hours to prepare a spherical mosaic cell mass of approximately 1 mm in diameter consisting of the recombinant peptide micro-blocks and the hMSC cells (0.002 μg of the polymer blocks per cell). Then, the medium was replaced by a chondrogenic differentiation medium (Takara Bio Inc.; hMSC Differentiation BulletKit™, Chondrogenic, TGF-β3) (200 μL). At Day 7, a spherical mosaic cell mass of 1.54 mm in diameter (=thickness) was formed (FIG. 1). In this context, this mosaic cell mass was prepared in a spherical shape because of being prepared in the U-shaped plate. Medium replacement was performed at Days 3, 7, 10, 14, 17, and 21.

Example 5

Preparation of Mosaic Cell Mass Using Natural Gelatin Micro-blocks

Human bone marrow-derived mesenchymal stem cells (hMSCs) were adjusted to 500,000 cells/mL with a growth medium (Takara Bio Inc.; MSCGM-CD™ BulletKit™). After addition of natural gelatin micro-blocks prepared in Example 3 to be 1.0 mg/mL, 100 μL of the mixture was inoculated to a Sumilon Celltight X96U plate and left standing for 18 hours to prepare a spherical mosaic cell mass of approximately 1 mm in diameter consisting of the natural gelatin micro-blocks and the hMSC cells (0.002 μg of the polymer blocks per cell). Then, the medium was replaced by a chondrogenic differentiation medium (Takara Bio Inc.; hMSC Differentiation BulletKit™, Chondrogenic, TGF-β3) (200 μL). At Day 7, a spherical mosaic cell mass of 1.34 mm in diameter (=thickness) was formed (FIG. 2). In this context, this mosaic cell mass was prepared in a spherical shape because of being prepared in the U-shaped plate.

Human bone marrow-derived mesenchymal stem cells (hMSCs) were adjusted to 500,000 cells/mL with a growth medium (Takara Bio Inc.; MSCGM-CD™ BulletKit™). The natural gelatin micro-blocks prepared in Example 3 were prepared by changing the conditions to final concentrations of 0.005 mg/mL, 0.01 mg/mL, 0.1 mg/mL, 0.2 mg/mL, 1.0 mg/mL, and 2.0 mg/mL, 100 μL of each mixture was inoculated to a Sumilon Celltight X96U plate and left standing for 18 hours to successfully prepare spherical mosaic cell masses of a little less than 1 mm in diameter (0.00001, 0.0002, 0.0004, 0.002, and 0.004 μg of the polymer blocks per cell).

Example 6

Sample Analysis

A tissue slice was prepared for the mosaic cell mass prepared in Example 4 using the recombinant peptide microblocks. After medium removal from the mosaic cell mass in the medium prepared in Example 4, the resulting mosaic cell mass was washed by the addition of 200 L of PBS, and this PBS was removed. This washing step was repeated twice. Then, the washed mosaic cell mass was dipped in 10% formalin, and formalin fixation was performed for 2 days. Then, the resulting cell mass was embedded in paraffin to prepare a tissue slice. The slice was stained with HE (hematoxylineosin), and the states of the cells and the gelatin micro-blocks were analyzed. The results are shown in FIGS. 3, 4, and 5. It could thereby be confirmed that: a three-dimensional construct in which the gelatin micro-blocks and the cells were arranged in a mosaic pattern was prepared; and the cells were present in a normal state in the mosaic cell mass. Moreover, from this cross-sectional slice, it was shown that a mosaic cell mass of at least 720 μm or larger in thickness could be prepared.

Example 7

Fusion of Mosaic Cell Masses

Whether the mosaic cell masses prepared in Example 4 could be fused, i.e., whether the mosaic cell masses arranged were able to form a larger three-dimensional construct by natural fusion, was examined. Two, three, or four mosaic cell masses of the 6th day prepared in Example 4 were arranged in a Sumilon Celltight X96U plate and cultured for 5 days. As a result, it was revealed that the cells placed on the periphery of each mosaic cell mass bound the mosaic cell masses to each other, whereby the mosaic cell masses were naturally fused. FIG. 6 shows a photograph taken with a stereoscopic microscope. Regarding the mosaic cell masses at the fusion start date (referred to as Day 6), the mosaic cell masses were merely placed adjacently to each other. By contrast, at the 5th day from the start of fusion (referred to as Day 11), a new layer was formed between the mosaic cell masses, demonstrating the manner in which the mosaic cell masses were fused. Also, FIGS. 7, 8, 9, 10, and 11 show results of preparing a tissue slice of the fused mosaic cell masses and HE-staining the cross section thereof (fixation was performed using 10% formalin, and embedding was performed using paraffin embedding). As is evident from the drawings, a fusion layer was formed between the mosaic cell masses by the cells and extracellular matrices produced by the cells to fuse and bind the mosaic cell masses to each other. It was thereby shown that the mosaic cell masses prepared in the present invention could be naturally fused and were able to form a larger construct by this fusion. Thus, it is demonstrated that use of the present invention achieves both of the preparation of a cell sheet having a thickness and the preparation of a more steric three-dimensional construct.

Example 8

Preparation of Mosaic Cell Mass under Growth Medium Using Recombinant Peptide Micro-blocks Human bone marrow-derived mesenchymal stem cells (hMSCs) were adjusted to 500,000 cells/mL with a growth medium (Takara Bio Inc.; MSCGM-CD™ BulletKit™). After addition of recombinant peptide micro-blocks prepared in Example 2 to be 1.0 mg/mL, 100 μL of the mixture was inoculated to a Sumilon Celltight X96U plate and left standing for 18 hours to prepare a spherical mosaic cell mass of 1 mm in diameter (0.002 μg of the polymer blocks per cell). Then, the volume of the medium was increased to 200 μL, and the mosaic cell mass was cultured with the medium replaced every 3 days. At Day 7, a spherical mosaic cell mass of 1.34 mm in diameter (=thickness) was formed (in this context, this mosaic cell mass was prepared in a spherical shape because of being prepared in the U-shaped plate). A photograph of a slice of the mosaic cell mass of Day 7 is shown in FIGS. 16 and 17. As is evident from the drawings, the thickness of even a site with a small thickness reached at least 624 μm or larger on this cross-sectional slice.

Example 9

Increase in Volume of Mosaic Cell Mass (Under Growth Medium)

0.1 mg of the recombinant peptide micro-blocks prepared in Example 2 was suspended in a growth medium (Takara Bio Inc.; MSCGM-CD™ BulletKit™) and added during medium replacement to the mosaic cell mass of the 3rd day (Day 3) prepared in Example 8. Subsequently, 0.1 mg of the recombinant peptide micro-blocks was added at the time of medium replacement at Days 7, 10, 14, 17, and 21.

Time-dependent change in each of diameter (calculated as an average of two different diameters) in the observation of this mosaic cell mass under stereoscopic microscope, area of the photographed mosaic cell mass, and calculated volume (calculated according to $4/3\pi r^3$ from the diameter determined above) is shown in FIGS. 12, 13, 14, and 15. As a result, a spherical mosaic cell mass of 3.41 mm in average diameter (=thickness) was finally formed at Day 21. It is thereby demonstrated that a mosaic cell mass up to at least 3.41 mm in size can be prepared. It is also demonstrated that the size can be increased by continuing increase in volume by this approach.

A tissue slice (HE-stained) at this time is shown in FIGS. 18 and 19. As is evident from the drawings, the cells and the recombinant peptide micro-blocks were arranged in a mosaic pattern. Moreover, since the mosaic cell mass was approximately 3 mm in size and small as a sample, it was extremely difficult to correctly create a cross section through the center of the sphere. Thus, although the deepest portion of the sphere was not obtained in the slice, even a portion from which this slice was collected in the sample was shown to be at least 1.17 mm in thickness.

As shown in FIGS. 12, 13, and 14, diameter was not changed in a mosaic cell mass cultured without adding the recombinant peptide micro-blocks during medium replacement at Days 7, 10, 14, 17, and 21. In the mosaic cell mass cultured without adding the recombinant peptide micro-blocks, a layered structure consisting only of the cells and extracellular matrices produced by the cells is formed by the proliferated cells in the outermost layer of the mosaic cell mass. As a result, the state in which the diffusion of nutrition is blocked by the layer of the cells and the produced extracellular matrices is formed to prevent the cells from being further proliferated (sized up). This is the reason for no change in diameter. On the other hand, when the recombinant peptide micro-blocks are constantly added at the timing of medium replacement, these recombinant peptide micro-blocks are always fit in the mosaic pattern together with the proliferated cells, whereby the mosaic structure consisting of the cells and the recombinant peptide micro-blocks can continue to be maintained even after cell proliferation. As a result, the supply pathway of nutrition provided by the recombinant peptide micro-blocks is always secured, and the outer layer unintentionally formed by the cells and the produced extracellular matrices is not generated. The resulting mosaic cell mass can be sized up.

Example 10

Increase in Volume of Mosaic Cell Mass (Under Chondrogenic Differentiation Medium)

0.1 mg of the recombinant peptide micro-blocks (0.1 mg) prepared in Example 2 was suspended in a chondrogenic differentiation medium (Takara Bio Inc.; hMSC Differentiation BulletKit™, Chondrogenic, TGF-β3) and added during medium replacement to the mosaic cell mass of the 3rd day (Day 3) prepared in Example 4. Subsequently, 0.1 mg of the recombinant peptide micro-blocks was added at the time of medium replacement at Days 7, 10, 14, 17, and 21.

Time-dependent change in each of diameter (calculated as an average of two different diameters) in the observation of this mosaic cell mass under stereoscopic microscope, area of the photographed mosaic cell mass, and calculated volume (calculated according to $4/3\pi r^3$ from the diameter determined above) is shown in FIGS. 12, 13, 14, and 15. As a result, a spherical mosaic cell mass of 2.05 mm in average diameter (=thickness) was finally formed at Day 21. It is thereby demonstrated that a mosaic cell mass up to at least 2.05 mm in size can be prepared. It is also demonstrated that the size can be increased by continuing increase in volume by this approach.

A tissue slice (HE-stained) at this time is shown in FIGS. 20 and 21. As is evident from the drawings, the cells and the recombinant peptide micro-blocks were arranged in a mosaic pattern. Moreover, since the mosaic cell mass was approximately 2 mm in size and small as a sample, it was extremely difficult to correctly create a cross section through the center of the sphere. Thus, although the deepest portion of the sphere was not obtained in the slice, even a portion from which this slice was collected in the sample was shown to be at least 897 μm in thickness.

As shown in FIGS. 12, 13, and 14, diameter was not changed in a mosaic cell mass cultured without adding the recombinant peptide micro-blocks during medium replacement at Days 7, 10, 14, 17, and 21. In the mosaic cell mass cultured without adding the recombinant peptide micro-blocks, a layered structure consisting only of the cells and extracellular matrices produced by the cells is formed by the proliferated cells in the outermost layer of the mosaic cell mass. As a result, the state in which the diffusion of nutrition is blocked by the layer of the cells and the produced extracellular matrices is formed to prevent the cells from being further proliferated (sized up). This is the reason for no change in diameter. On the other hand, when the recombinant peptide micro-blocks are constantly added at the timing of medium replacement, these recombinant peptide micro-blocks are always fit in the mosaic pattern together with the proliferated cells, whereby the mosaic structure consisting of the cells and the gelatin micro-blocks can continue to be maintained even after cell proliferation. As a result, the supply pathway of nutrition provided by the recombinant peptide micro-blocks is always secured, and the outer layer unintentionally formed by the cells and the produced extracellular matrices is not generated. The resulting mosaic cell mass can be sized up.

Example 11

Determination of Amount of Gag Produced in Mosaic Cell Mass (Time-dependent Change)

The amount of glycosaminoglycan in each mosaic cell mass was determined for the mosaic cell masses prepared in Examples 4 and 5 (hMSC cells+recombinant peptide and hMSC cells+natural gelatin) and a cell mass prepared using only the cells (prepared by the same approach as in Example 4 without the gelatin blocks). Measurement was performed by a method using a Dimetylmethylene blue dye (Farndale et al., Improved quantitation and sulphated glycosaminoglycans by use of dimethylmethylene blue. Biochimica et Biophysica Acta 883 (1986) 173-177), and Sulfated GAG Quantification Kit (Seikagaku Biobusiness Corp.) was used as a reagent. Absorbance at 530 nm was measured for quantification. As shown in FIG. 21, it was confirmed that characteristic absorption peaks were seen at 525-530 nm by the approach.

Results of determining the amount of GAG over time are shown in the graph of FIG. 22. As a result, the amount of glycosaminoglycan (GAG) produced was low in the cell mass prepared without the gelatin micro-blocks or the recombinant peptide micro-blocks, whereas the amount of GAG produced was exceedingly high in the mosaic cell mass prepared with the natural gelatin micro-blocks and the mosaic cell mass prepared with the recombinant peptide micro-blocks. It could thereby be confirmed that: chondrogenic differentiation was promoted in the mosaic cell masses prepared in Examples 4 and 5; and the prepared mosaic cell masses had functions as cells (had the ability to produce GAG). Furthermore, the amount of GAG produced was significantly higher in the mosaic cell mass prepared with the recombinant peptide micro-blocks than the mosaic cell mass prepared with the natural gelatin micro-blocks. This demonstrated that the mosaic cell mass prepared with the recombinant peptide micro-blocks was able to maintain higher cell activity and substrate-producing activity than those brought about by the natural gelatin micro-blocks, and showed that use of the recombinant peptide was able to achieve the amount of the substrate produced, which was impossible to achieve with the natural gelatin.

Example 12

ATP Quantification for Mosaic Cell Mass

The amount of ATP (adenosine triphosphate) produced/retained by the cells in each mosaic cell mass was determined. ATP is known as an energy source for general organisms. The active metabolic state and activity state of cells can be known by determining the amount of ATP synthesized/retained. CellTiter-Glo (Promega Corp.) was used in measurement. For comparison, the amount of ATP in each mosaic cell mass was determined using CellTiter-Glo for the mosaic cell masses prepared in Examples 4 and 5 (hMSC cells+recombinant peptide and hMSC cells+natural gelatin) and a cell mass prepared using only the cells (prepared by the same approach as in Example 4 without the gelatin blocks), all of which were of Day 7.

The results are shown in FIG. 23. As is thereby evident, the amount of ATP produced/retained was significantly higher ($p<0.01$) in the mosaic cell mass prepared using the recombinant peptide micro-blocks or the gelatin micro-blocks than the cell mass prepared using only the cells. This suggests that the micro-blocks are fit in the mosaic pattern, whereby the nutrition supply pathway into the mosaic cell mass is provided by the micro-blocks and the highly active metabolic state of the cells is more maintained than in the mass consisting only of the cells. It was further demonstrated that the amount of ATP produced/retained was significantly higher in the mosaic cell mass prepared with the recombinant peptide micro-blocks than the mosaic cell mass prepared with the natural gelatin micro-blocks. It was thereby demonstrated that the mosaic cell mass prepared with the recombinant peptide micro-blocks exhibited higher cell survival than that brought about by the natural gelatin micro-blocks and the cells within this mosaic cell mass was alive. Use of the recombinant peptide was shown to be able to achieve improvement in cell survival, which was impossible to achieve with the natural gelatin.

Example 13

Preparation of PLGA Micro-blocks 0.3 g of PLGA (poly(lactic-co-glycolic acid); Wako Pure Chemical Industries, Ltd., PLGA7520) was dissolved in dichloromethane (3 mL). The PLGA solution was vacuum dried in a dryer (EYELA, FDU-1000) to obtain a dried product of PLGA. The dried product of PLGA was pulverized with New Power Mill (Osaka Chemical Co., Ltd., New Power Mill PM-2005). The pulverization was performed at the maximum number of revolutions for 10 seconds×20 runs. The obtained particles were sized through a stainless sieve to obtain 25 to 53 μm and 53 to 106 μm PLGA micro-blocks.

PLGA: "1/IOB" value: 0.0552

Example 14

Preparation of Mosaic Cell Mass Using PLGA

Human bone marrow-derived mesenchymal stem cells (hMSCs) were adjusted to 500,000 cells/mL with a growth medium (Takara Bio Inc.; MSCGM-CD™ BulletKit™). After addition of the PLGA micro-blocks prepared in Example 13 (prepared by changing the conditions to final concentrations of 0.1 mg/mL, 0.2 mg/mL, 1.0 mg/mL, and 2.0 mg/mL), 100 μL of each mixture was inoculated to a Sumilon Celltight X96U plate and left standing for 18 hours to prepare spherical mosaic cell masses of a little less than 1 mm in diameter (0.0002, 0.0004, 0.002, and 0.004 μg of the polymer blocks per cell). Then, the volume of the medium was increased to 200 μL, and each mosaic cell mass was cultured with the medium replaced every 3 days. In this context, this mosaic cell mass was prepared in a spherical shape because of being prepared in the U-shaped plate. A stereoscopic microscope photograph of the PLGA mosaic cell mass of Day 2 is shown in FIG. 24.

Example 15

Preparation of Agarose Micro-blocks

Ultrapure water (100 mL) was added to 5 g of agarose powders, and the powders were dissolved by heating using a microwave oven. The obtained 5% agarose solution was bought back to room temperature to obtain solid matter. The solid matter was frozen at −80° C. for 5 hours and then freeze-dried in a freeze dryer (EYELA, FDU-1000) to obtain a freeze-dried product of agarose. The freeze-dried product of agarose was pulverized with New Power Mill (Osaka Chemical Co., Ltd., New Power Mill PM-2005). The pulverization was performed at the maximum number of revolutions for 10 seconds×20 runs. The obtained particles were sized through a stainless sieve to obtain 25 to 53 μm and 53 to 106 μm agarose micro-blocks.

IOB value: 3.18

Example 16

Preparation of Mosaic Cell Mass Using Agarose

Human bone marrow-derived mesenchymal stem cells (hMSCs) were adjusted to 500,000 cells/mL with a growth medium (Takara Bio Inc.; MSCGM-CD™ BulletKit™). After addition of the agarose micro-blocks prepared in Example 15 (prepared by changing the conditions to final concentrations of 0.1 mg/mL and 1.0 mg/mL), 100 μL of each mixture was inoculated to a Sumilon Celltight X96U plate and left standing for 18 hours to prepare spherical mosaic cell masses of a little less than 1 mm in diameter (0.0002 and 0.002 μg of the polymer blocks per cell). Then, the volume of the medium was increased to 200 μL, and each mosaic cell mass was cultured with the medium replaced every 3 days. In this context, this mosaic cell mass was prepared in a spherical shape because of being prepared in the U-shaped plate.

Example 17

Preparation of Mosaic Cell Mass Using Cardiac Muscle Cells

New-born SD rat cardiac muscle cells (rCMCs) were adjusted to 500,000 cells/mL with a medium for cardiac muscle cells (Primary Cell Co., Ltd; CMCM culture medium for cardiac muscle cells). After addition of recombinant peptide micro-blocks prepared in Example 2 to be 0.5, 1.0 or 3.0 mg/mL, 100 μL of each mixture was inoculated to a Sumilon Celltight X96U plate (Sumitomo Bakelite Co., Ltd., U-shaped bottom) and left standing for 18 hours to prepare mosaic cell masses of approximately 1 to 2 mm in diameter consisting of the recombinant peptide micro-blocks and the rCMC cells (0.001, 0.002, and 0.006 μg of the polymer blocks per cell). Medium replacement was performed at Days 3, 7, 10, 14, 17, and 21.

At the stages of Days 1 and 3, the rCMC mosaic cell mass could already be confirmed to beat in synchronization as the whole construct (FIG. 25). Since moving images are difficult to show in the specification, FIG. 25 is an image taken by capturing still images of the same spot after 0.2 seconds from the moving images. As is evident from the site marked with the triangle, the whole construct moved in two pictures.

This could show that even use of cardiac muscle cells was able to form the three-dimensional cell construct (mosaic cell mass) of the present invention, and also demonstrated that the mosaic cell mass containing the cardiac muscle cells was obtained as a cell construct that beat in synchronization as the whole construct.

Example 18

Preparation of Mosaic Cell Mass Using GFP-expressing HUVECs (Human Umbilical Vein Endothelial Cells)

GFP-expressing human umbilical vein endothelial cells (GFP-HUVECs; Angio-Proteomie) were adjusted to 500,000 cells/mL with a medium for endothelial cells (Kurabo Industries Ltd.; Medium 200S, LSGS, antimicrobial agent GA solution). After addition of recombinant peptide micro-blocks prepared in Example 2 to be 0.3, 1.0 or 3.0 mg/mL, 100 µL of each mixture was inoculated to a Sumilon Celltight X96U plate (Sumitomo Bakelite Co., Ltd., U-shaped bottom) (0.0006, 0.002, and 0.006 µg of the polymer blocks per cell). Likewise, the cells were also adjusted to 1,500,000 cells/mL, and after addition of recombinant peptide micro-blocks prepared in Example 2 to be 1.0 mg/mL, 100 µL or 200 µL of the mixture was inoculated to a Sumilon Celltight X96U plate (Sumitomo Bakelite Co., Ltd., U-shaped bottom) and prepared. All of them were separately left standing for 18 hours to prepare mosaic cell masses of approximately 1 to 2 mm in diameter consisting of the recombinant peptide micro-blocks and the GFP-HUVEC cells. Medium replacement was performed at Days 3, 7, 10, 14, 17, and 21.

Figure 26:
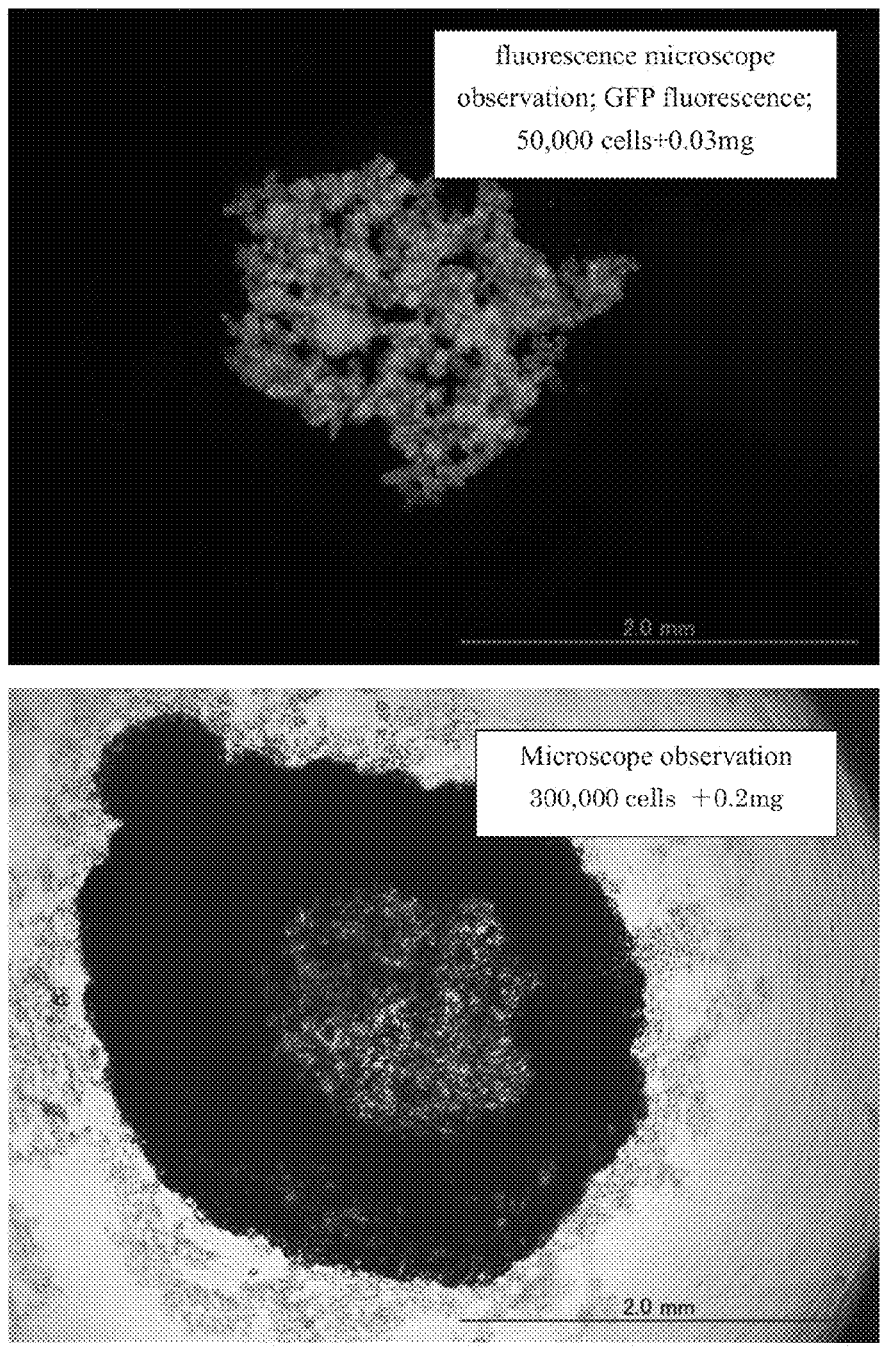
FIG. 26 shows microscope photographs and fluorescence microscope photographs of mosaic cell masses consisting of GFP-expressing HUVEC and the recombinant peptide micro-blocks (a mosaic cell mass of 50000 cells+0.03 mg of the micro-blocks and a mosaic cell mass of 300000 cells+0.2 mg of the micro-blocks).

FIG. 26 shows microscope photographs and fluorescence microscope photographs of a mosaic cell mass of 50,000 cells+0.03 mg of the micro-blocks and a mosaic cell mass of 300,000 cells+0.2 mg of the micro-blocks. Since the GFP-HUVEC cells emit the fluorescence of GFP, distribution in the mosaic cell mass is easily understood by means of the fluorescence microscope. Even use of vascular endothelial cells was thereby shown to be able to prepare the three-dimensional cell construct (mosaic cell mass) of the present invention.

It was also demonstrated that the cell construct (mosaic cell mass) of the present invention could be formed with diverse cells, such as mesenchymal stem cells, cardiac muscle cells, and vascular endothelial cells. At the same time, it was shown that the cell construct (mosaic cell mass) of the present invention could be formed with diverse polymer blocks, such as recombinant peptide blocks, animal gelatin blocks, PLGA blocks, and agarose blocks. This proved that the three-dimensional cell construct (mosaic cell mass) of the present invention could be formed with diverse cell species and diverse polymer block species.

Example 19-(1)

Preparation of Mosaic Cell Mass Using Recombinant Peptide Micro-blocks (hMSCs)

Human bone marrow-derived mesenchymal stem cells (hMSCs) were adjusted to 100,000 cells/mL with a growth medium (Takara Bio Inc.; MSCGM BulletKit™). After addition of recombinant peptide micro-blocks prepared in Example 2 to be 0.1 mg/mL, 200 µL of the mixture was inoculated to a Sumilon Celltight X96U plate (Sumitomo Bakelite Co., Ltd., U-shaped bottom), centrifuged (600 g, 5 minutes) with a tabletop plate centrifuge, and left standing for 24 hours to prepare a spherical mosaic cell mass of approximately 1 mm in diameter consisting of the recombinant peptide micro-blocks and the hMSC cells (0.001 µg of the polymer blocks per cell). In this context, this mosaic cell mass was prepared in a spherical shape because of being prepared in the U-shaped plate.

Example 19-(2)

Larger Size by Fusion of Mosaic Cell Masses

Figure 27:
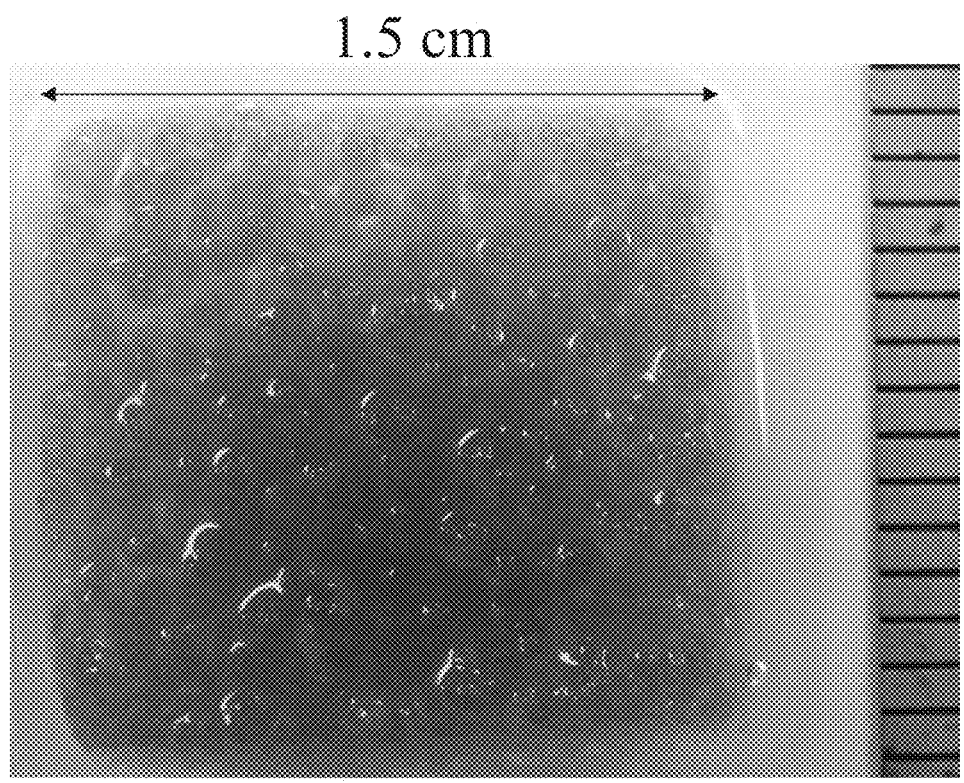
FIG. 27 shows a stereoscopic microscope photograph of a fused form of larger mosaic cell masses.

Whether the mosaic cell masses prepared in Example 19-(1) could be fused, i.e., whether the mosaic cell masses arranged were able to form a larger three-dimensional construct by natural fusion, was examined. First, a rectangular silicon sheet (3 mm thick) suitable for the size of PrimeSurface 90 mm dish was prepared, and a piece of 1.5 cm square was hollowed out of the central portion. The resulting silicon sheet was sterilized with ethanol, washed with PBS, and used. It was put in PrimeSurface 90 mm dish, and 1,500 mosaic cell masses prepared in Example 19-(1) were placed thereon, so that they were arranged in the site of 1.5 cm square. 50 ml of a growth medium (Takara Bio Inc.; MSCGM BulletKit™) was gently added thereto, and the mosaic cell masses were cultured for 2 days. As a result, a fused form of the mosaic cell masses of 1.5 cm square and 2 mm in thickness could be prepared. FIG. 27 shows a photograph taken with a stereoscopic microscope. From a HE-stained cross sectional slice of this fused form, it could also be confirmed that the cells inside thereof survived. It was thereby shown that the mosaic cell masses could be naturally fused and were able to form a larger construct of cm order by this fusion. Thus, it is demonstrated that the mosaic cell mass can be prepared into a cell sheet having a thickness as used in cell transplantation and can be prepared into a more steric three-dimensional construct.

Example 20

Preparation of Mosaic Cell Mass Using Recombinant Peptide Micro-blocks (hMSCs+hECFCs)

Example 20-(1)

Human bone marrow-derived mesenchymal stem cells (hMSCs) were adjusted to 100,000 cells/mL with a growth medium (Takara Bio Inc.; MSCGM BulletKit™). After addition of recombinant peptide micro-blocks prepared in Example 2 to be 0.1 mg/mL, 200 µL of the mixture was inoculated to a Sumilon Celltight X96U plate, centrifuged (600 g, 5 minutes) with a tabletop plate centrifuge, and left standing for 24 hours to prepare a spherical mosaic cell mass of approximately 1 mm in diameter consisting of the recombinant peptide micro-blocks and the hMSC cells. Then, the medium was removed, and human vascular endothelial precursor cells (hECFCs) were adjusted to 100,000 cells/mL with a growth medium (Lonza; EGM-2+ECFC serum supplement). After addition of recombinant peptide micro-blocks prepared in Example 2 to be 0.025 mg/mL, 200 µL of the mixture with the mosaic cell mass containing the hMSC cells was inoculated to the Sumilon Celltight X96U plate, centrifuged (600 g, 5 minutes) with a tabletop plate centrifuge, and left standing for 24 hours to prepare a mosaic cell mass in which a layer of hECFCs and the recombinant peptide micro-blocks was formed to surround the spherical mosaic cell mass of approximately 1 mm in diameter consisting of the recombinant peptide micro-blocks and the hMSC cells. In this context, this mosaic cell mass was prepared in a spherical shape because of being prepared in the U-shaped plate.

Example 20-(2)

Human vascular endothelial precursor cells (hECFCs) were adjusted to 100,000 cells/mL with a growth medium (Lonza; EGM-2+ECFC serum supplement). After addition of recombinant peptide micro-blocks prepared in Example 2 to be 0.05 mg/mL, 200 μL of the mixture was inoculated to a Sumilon Celltight X96U plate, centrifuged (600 g, 5 minutes) with a tabletop plate centrifuge, and left standing for 24 hours to prepare a flat mosaic cell mass consisting of ECFCs and the recombinant peptide micro-blocks. Then, the medium was removed, and human bone marrow-derived mesenchymal stem cells (hMSCs) were adjusted to 100,000 cells/mL with a growth medium (Takara Bio Inc.; MSCGM BulletKit™). After addition of recombinant peptide micro-blocks prepared in Example 2 to be 0.1 mg/mL, 200 μL of the mixture with the hECFC mosaic cell mass was inoculated to the Sumilon Celltight X96U plate, centrifuged (600 g, 5 minutes) with a tabletop plate centrifuge, and left standing for 24 hours to prepare a spherical mosaic cell mass of approximately 1 mm in diameter that consisted of the recombinant peptide micro-blocks and the hMSC cells and incorporated the mosaic cell mass consisting of ECFCs and the recombinant peptide micro-blocks. In this context, this mosaic cell mass was prepared in a spherical shape because of being prepared in the U-shaped plate (the mosaic cell mass obtained here is designated as A). Furthermore, when the amounts of the human vascular endothelial precursor cells (hECFCs) and the recombinant peptide micro-blocks were changed to 200,000 cells/mL and 0.1 mg/mL, respectively, and the amounts of the human bone marrow-derived mesenchymal stem cells (hMSCs) and the recombinant peptide micro-blocks were changed to 200,000 cells/mL and 0.2 mg/mL, respectively, a mosaic cell mass of approximately 1 mm in thickness and approximately 1.5 mm in diameter was also successfully prepared (the mosaic cell mass obtained here is designated as B).

Example 20-(3)

Human bone marrow-derived mesenchymal stem cells (hMSCs) were adjusted to 100,000 cells/mL with a growth medium (Takara Bio Inc.; MSCGM BulletKit™), and human vascular endothelial precursor cells (hECFCs) were adjusted to 100,000 cells/mL with a growth medium (Lonza; EGM-2+ECFC serum supplement). After addition of recombinant peptide micro-blocks prepared in Example 2 to be 0.15 mg/mL, 200 μL of the mixture was inoculated to a Sumilon Celltight X96U plate, centrifuged (600 g, 5 minutes) with a tabletop plate centrifuge, and left standing for 48 hours to prepare a spherical mosaic cell mass of approximately 1 mm in diameter consisting of the recombinant peptide micro-blocks, hMSCs, and hECFCs. In this context, this mosaic cell mass was prepared in a spherical shape because of being prepared in the U-shaped plate.

Comparative Example 1

Preparation of Cell Mass Using Only Cells (hMSCs)

Human bone marrow-derived mesenchymal stem cells (hMSCs) were adjusted to 375,000 cells/mL with a growth medium (Takara Bio Inc.; MSCGM BulletKit™). 200 μL thereof was inoculated to a Sumilon Celltight X96U plate (Sumitomo Bakelite Co., Ltd., U-shaped bottom), centrifuged (600 g, 5 minutes) with a tabletop plate centrifuge, and left standing for 24 hours to prepare a spherical cell mass of approximately 1 mm in diameter consisting of the hMSC cells. In this context, this mosaic cell mass was prepared in a spherical shape because of being prepared in the U-shaped plate.

Comparative Example 2

Preparation of Cell Mass Using Only Cells (hMSCs+hECFCs)

Human vascular endothelial precursor cells (hECFCs) were adjusted to 100,000 cells/mL with a growth medium (Lonza; EGM-2+ECFC serum supplement). 200 μL thereof was inoculated to a Sumilon Celltight X96U plate, centrifuged (600 g, 5 minutes) with a tabletop plate centrifuge, and left standing for 24 hours to prepare a hECFC cell mass. Then, the medium was removed, and human bone marrow-derived mesenchymal stem cells (hMSCs) were adjusted to 300,000 cells/mL with a growth medium (Takara Bio Inc.; MSCGM BulletKit™). 200 μL thereof with the hECFC mosaic cell mass was inoculated to the Sumilon Celltight X96U plate, centrifuged (600 g, 5 minutes) with a tabletop plate centrifuge, and left standing for 24 hours to prepare a spherical cell mass of approximately 1 mm in diameter consisting of hECFCs and hMSCs (the cell mass obtained here is designated as A). Moreover, human vascular endothelial precursor cells (hECFCs) were adjusted to 200,000 cells/mL with a growth medium (Lonza; EGM-2+ECFC serum supplement). 200 μL thereof was inoculated to a Sumilon Celltight X96U plate, centrifuged (600 g, 5 minutes) with a tabletop plate centrifuge, and left standing for 24 hours to prepare a hECFC cell mass. Then, the medium was removed, and human bone marrow-derived mesenchymal stem cells (hMSCs) were adjusted to 200,000 cells/mL with a growth medium (Takara Bio Inc.; MSCGM BulletKit™). 200 μL thereof with the hECFC mosaic cell mass was inoculated to the Sumilon Celltight X96U plate, centrifuged (600 g, 5 minutes) with a tabletop plate centrifuge, and left standing for 24 hours to prepare a spherical cell mass of approximately 1 mm in diameter consisting of hECFCs and hMSCs (the cell mass obtained here is designated as B).

Sample Analysis

Figure 28:
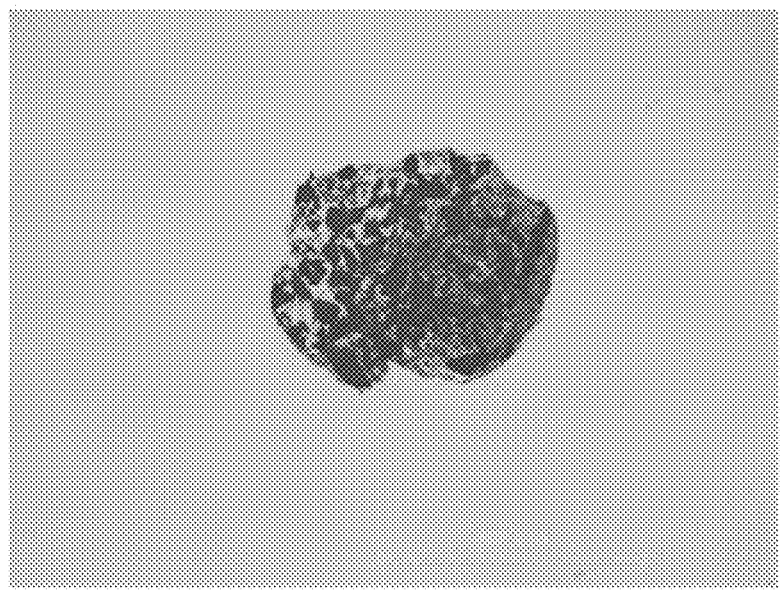
FIG. 28 shows a photograph of a slice (HE-stained) of a mosaic cell mass containing the recombinant peptide micro-blocks.
Figure 29:
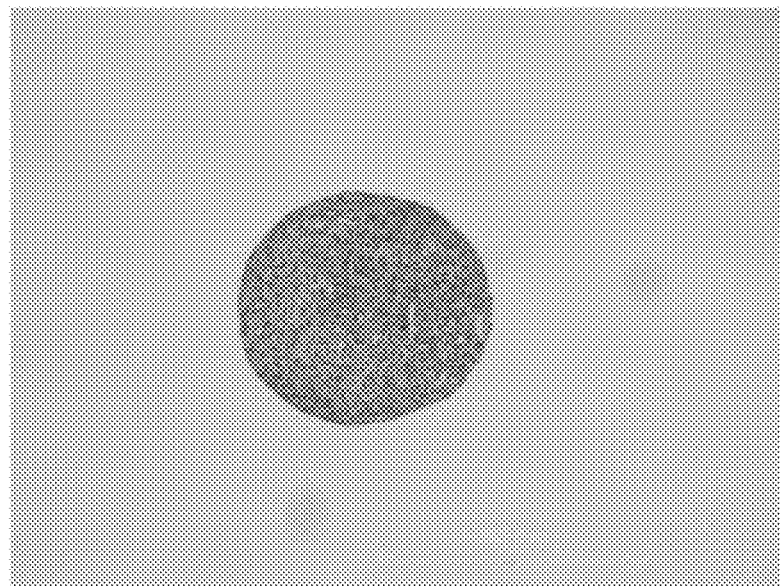
FIG. 29 shows a photograph of a slice (HE-stained) of a hMSC cell mass.
Figure 32:
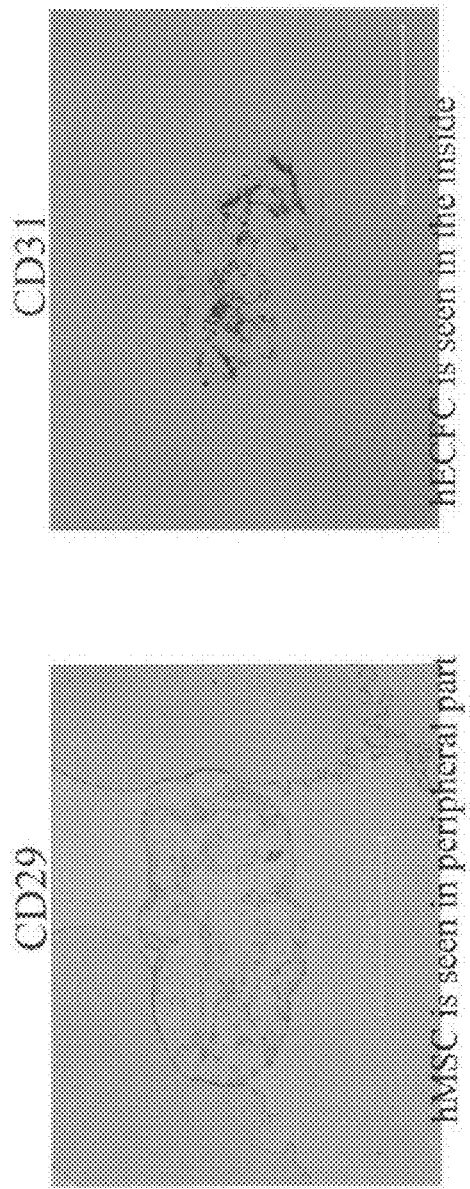
FIG. 32 shows a photograph of a slice (immunostained with an anti-CD29 antibody and an anti-CD31 antibody) of a mosaic cell mass produced in Example 20-(2)B using the recombinant peptide.

A tissue slice was prepared for the mosaic cell masses prepared in Examples 19-(1) and 20 and Comparative Example 1 using the recombinant peptide micro-blocks. The thickness of the slice was set to 2 μm. After medium removal from each prepared mosaic cell mass in the medium, the resulting mosaic cell mass was washed by the addition of 200 μL of PBS, and this PBS was removed. This washing step was repeated twice. Then, the washed mosaic cell mass was dipped in 10% formalin, and formalin fixation was performed. Then, the resulting cell mass was embedded in paraffin to prepare a tissue slice. For Example 19-(1) and Comparative Example 1, the slice was stained with HE (hematoxylin-eosin), and the states of the cells and the recombinant peptide micro-blocks were analyzed. The results are shown in FIGS. 28 and 29. It could thereby be confirmed that: a three-dimensional construct in which the recombinant peptide micro-blocks and the cells were arranged in a mosaic pattern was prepared in the mosaic cell mass; and the cells were present in a normal state in the mosaic cell mass. Moreover, from this cross-sectional slice, it was shown that a mosaic cell mass and a cell mass of at least 500 µm in thickness could be prepared.

Furthermore, the slice of each mosaic cell mass of Example 20 was immunostained with an anti-CD31 antibody (EPT, Anti CD31/PECAM-1) for hECFC staining or with an anti-CD29 antibody (EPT, Anti Integrin β-1 (CD29)) for hMSC/hECFC staining using a kit using DAB color development (Dako LSAB2 kit, Universal, K0673 Dako LSAB2 kit/HRP (DAB), for use with both rabbit and mouse primary antibodies) (FIGS. 30, 31, 32, and 33). The ratio of the area of hECFCs (vascular cells) in the central portion was determined for the mosaic cell masses prepared in Examples 20-(1) to 20-(3) using the image processing software ImageJ described above and the staining method using an anti-CD31 antibody. In this context, the "central portion" is as defined above.

As a result, the ratio of the area of hECFCs (vascular cells) in the central portion of the mosaic cell mass of Example 20-(1) was 24%; the ratio of the area of hECFCs in the central portion of the mosaic cell mass of Example 20-(2) was 91% for both A and B; and the ratio of the area of hECFCs in the central portion of the mosaic cell mass of Example 20-(3) was 67%.

Furthermore, the density of the hECFC cells present in the central portion was calculated for each mosaic cell mass of Example 20 by superimposing the anti-CD31 antibody staining image and the HE staining (hematoxylin-eosin staining) image. The density of the vascular cells in the central portion can be determined by actually counting the number of cells in a thin section sample and dividing the number of cells by volume. First, these two images were superimposed using Photoshop, and the number of anti-CD31 antibody-stained cell nuclei overlapping with HE stained cell nuclei was counted to calculate the number of cells. Meanwhile, the volume was determined by determining the area of the central portion using ImageJ and multiplying the area by 2 µm as the thickness of the thin section sample.

As a result, the number of the hECFC cells (vascular cells) in the central portion of the mosaic cell mass of Example 20-(1) was $1.58 \times 10^{-5}$ cells/µm$^3$; the number of the hECFC cells in the central portion of the mosaic cell mass A of Example 20-(2) was $1.12 \times 10^{-4}$ cells/µm$^3$; and the number of the hECFC cells in the central portion of the mosaic cell mass of Example 20-(3) was $1.06 \times 10^{-4}$ cells/µm$^3$. In the case of B of Example 20-(2) in which the number of cells and the weight of the blocks were doubled, the number of the hECFC cells in the central portion was $1.72 \times 10^{-4}$ cells/µm$^3$.

Example 21

In vivo Survival Difference Evaluation Test in Mice Using hMSC Mosaic Cell Mass

A test was conducted in vivo in mice to confirm that hMSCs at the center of the mosaic cell mass survived.
Transplantation of Mosaic Cell Mass and Cell Mass Five-week-old male Balb/c Nude mice (Charles River Laboratories Japan, Inc.) were raised for approximately 5 weeks and used in the test when they were approximately 10 weeks old. First, the skin between the first and second ankle joints (hereinafter, this region is referred to as the lower leg) from the edge of the limb of each mouse was incised under anesthesia with scissors and opened up. Then, the muscle in the lower leg was incised by approximately 5 mm with a knife, and the hMSC mosaic cell mass prepared in Example 19-(1) or the hMSC cell mass prepared in Comparative Example 1 was implanted in the incision site using tweezers. The incision site in the muscle was sutured with suture thread, and the skin was further sutured.

In addition, a transplantation method involving muscular injection into the lower leg was also performed as another approach. Ten hMSC mosaic cell masses prepared in Example 19-(1) or ten hMSC cell masses prepared in Comparative Example 1 were placed together with 200 µl of a hMSC growth medium (Takara Bio Inc.; MSCGM Bullet-Kit™) in a 1-mm syringe and injected to the muscle in the lower leg using a 18 G injection needle (Terumo Corp.).
Collection of Mosaic Cell Mass Anatomy was performed 2 days, 5 days, 8 days, and 13 days after transplantation. In the case of the transplantation by muscle incision, the skin in the lower leg of each mouse was taken off, and the suture thread in the muscle in the lower leg was removed. The incision site was opened with a knife. After visual confirmation of the transplanted hMSC mosaic cell mass and hMSC cell mass, the femoral region together with bone was cut with scissors and further cut off at the ankle.

In the case of the transplantation by muscular injection, the skin in the lower leg of each mouse was taken off, and the muscle in the lower leg was incised with a knife. After visual confirmation of the transplanted hMSC mosaic cell mass and hMSC cell mass, the muscle to which each cell mass was attached was cut out.
Sample Analysis A tissue slice was prepared for the lower leg containing the mosaic cell mass or the cell mass, the muscle to which the hMSC mosaic cell mass or the hMSC cell mass was attached, and the mosaic cell mass and cell mass before transplantation. The femoral region was dipped in 4% paraformaldehyde, and formalin fixation was performed. Then, the resulting product was embedded in paraffin to prepare a tissue slice of the lower leg containing the hMSC mosaic cell mass or the hMSC cell mass. The slice was stained with HE (hematoxylin-eosin) and immunostained with an anti-CD29 antibody for hMSC cell staining using a DAB color development method to analyze cell distribution. An image of the HE-stained slice at the 5th day after transplantation is shown (FIGS. 34 and 35).

Figure 34:
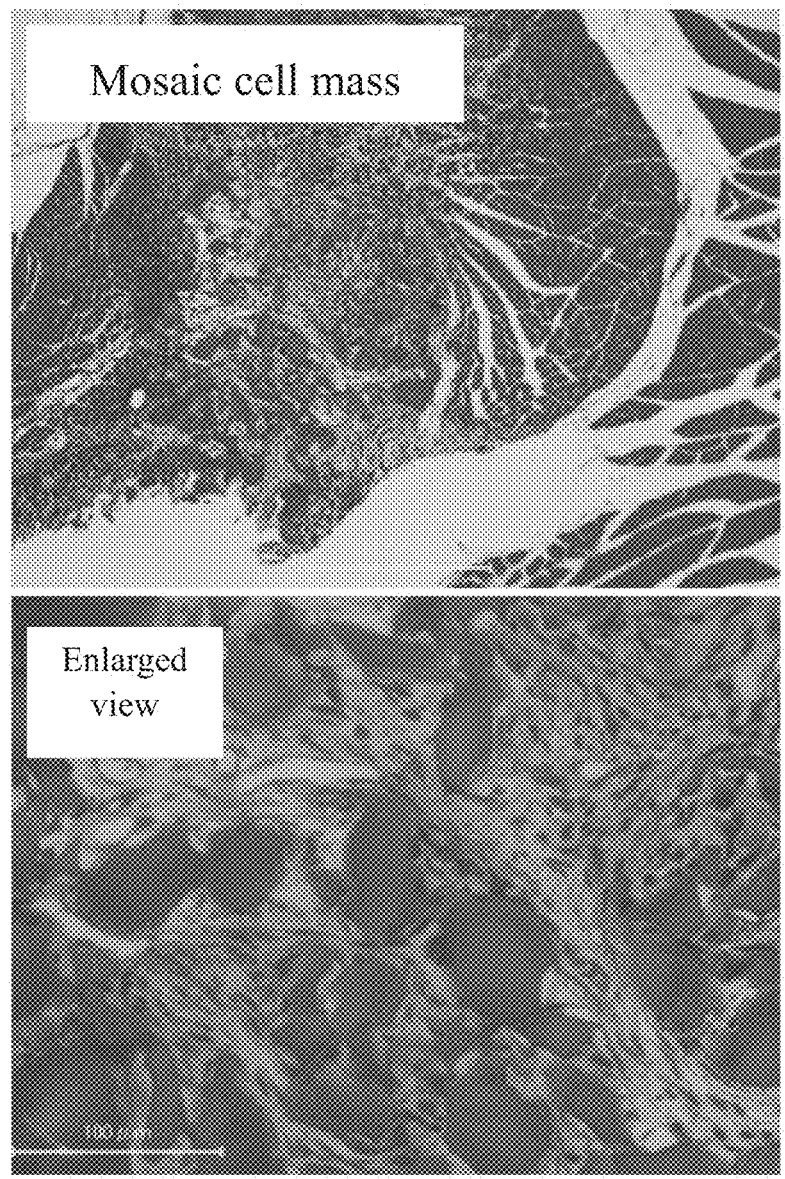
FIG. 34 shows a photograph of a tissue slice (HE-stained) of a transplantation site after transplantation of the mosaic cell mass (Example 19-(1)) containing the recombinant peptide micro-blocks.
Figure 35:
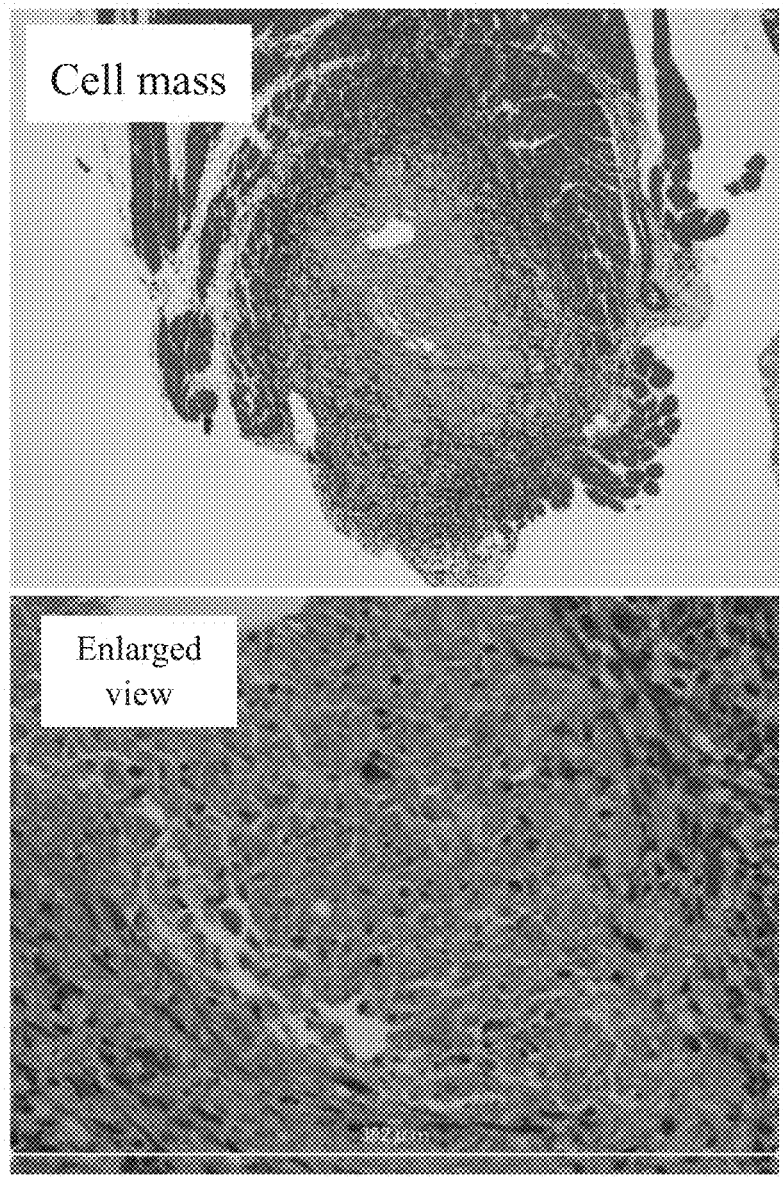
FIG. 35 shows a photograph of a tissue slice (HE-stained) of a transplantation site after transplantation of a hMSC cell mass (Comparative Example 1).

Referring to FIG. 34, the nuclei of the hMSC cells at the center of the mosaic cell mass were clearly shown, and 100% of hMSCs in the whole mosaic cell mass survived. By contrast, referring to FIG. 35, nuclear pyknosis and obscuration occurred at the center of the mass consisting only of the cells, and the hMSC cells necrotized while 62.7% cells survived in the whole cell mass. It could be confirmed that hMSCs necrotized at the center of the hMSC cell mass in vivo, whereas hMSCs were able to survive even at the center of the hMSC mosaic cell mass.

Moreover, it could be confirmed that blood vessels were formed within the hMSC mosaic cell mass at the 5th day. The number of blood vessels was 6 per area. By contrast, no blood vessel formation was seen within the hMSC cell mass, and the number of blood vessels per area was 0. The hMSC mosaic cell mass was shown to form blood vessels therewithin in vivo and create an environment suitable for cell survival.

Example 22-(1)

In vivo Blood Vessel Formation Difference Evaluation Test in Mice Using Mosaic Cell Mass of hMSCs and hECFCs Transplantation of Mosaic Cell Mass
Four-week-old male NOD/SCID mice (Charles River Laboratories Japan, Inc.) were raised for approximately 8 weeks and used in the test when they were approximately 12 weeks old. The abdominal hair of each mouse was removed under anesthesia. The upper abdominal region was subcutaneously slit up, and scissors were inserted through the slit to take off the skin from the muscle. Then, each of 3 types of hMSC+hECFC mosaic cell masses prepared in Examples 20(1) to 20(3) was scooped with tweezers and subcutaneously transplanted in the abdominal region 1.5 cm below the slit, and the slit in the skin was sutured.

Collection of Mosaic Cell Mass

Anatomy was performed 5 days, 14 days, and 28 days after transplantation. The skin in the abdominal region was taken off, and the skin to which each mosaic cell mass was attached was cut into a square of approximately 1 cm² in size. In the case where the mosaic cell mass was also attached to the muscle in the abdominal region, the mosaic cell mass was collected together with the muscle.

A tissue slice was prepared for the skin slice to which the mosaic cell mass was attached and the mosaic cell masses before transplantation. The skin was dipped in 4% paraformaldehyde, and formalin fixation was performed. Then, the resulting product was embedded in paraffin to prepare a tissue slice of the skin containing each mosaic cell mass. The slice was stained with HE (hematoxylin-eosin) and immunostained with an anti-CD31 antibody for hECFC staining using a DAB color development method to analyze blood vessel formation and the states of hMSC and hECFC behaviors within the mosaic cell mass. An image of the HE-stained slice at the 5th day after transplantation is shown.

Figure 36:
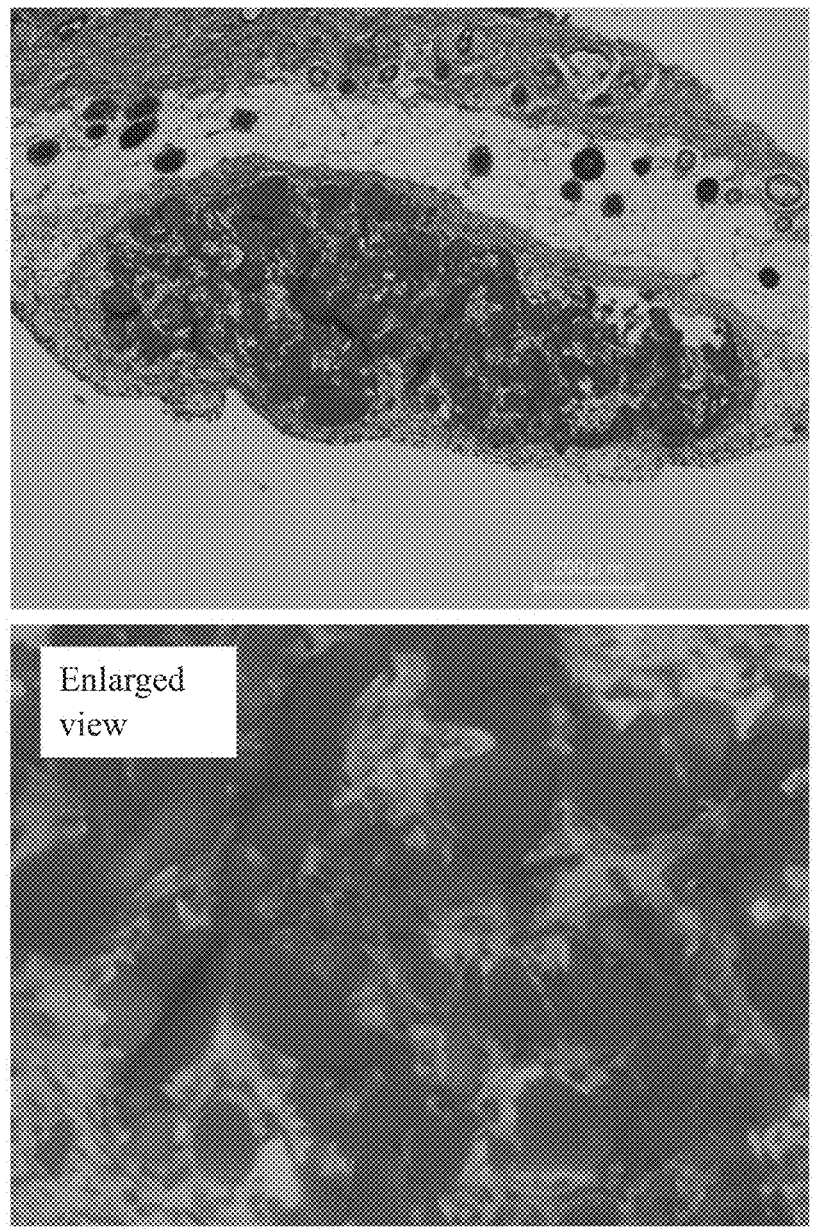
FIG. 36 shows a photograph of a tissue slice (HE-stained) of a transplantation site after transplantation of the mosaic cell mass (Example 20-(1)) containing the recombinant peptide micro-blocks.
Figure 38:
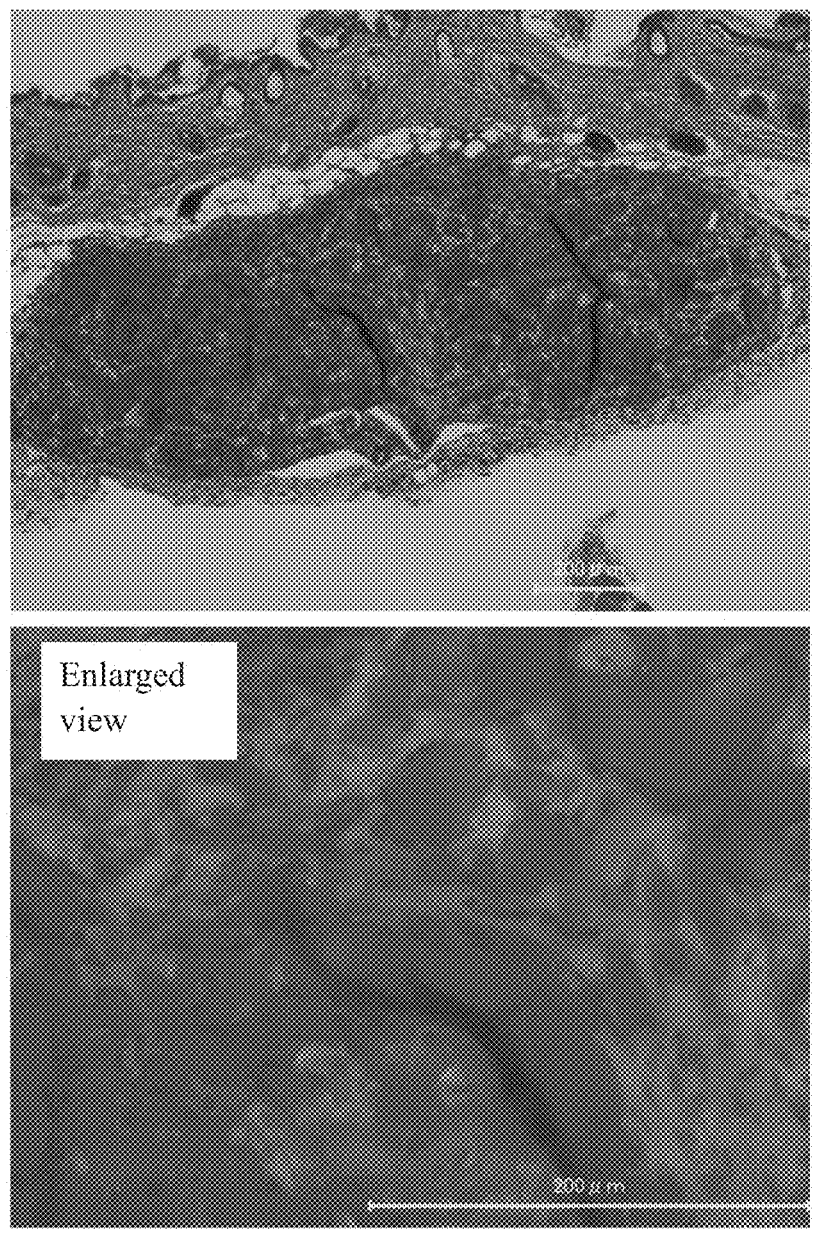
FIG. 38 shows a photograph of a tissue slice (HE-stained) of a transplantation site after transplantation of the mosaic cell mass (Example 20-(3)) containing the recombinant peptide micro-blocks.

FIG. 36 is an image of the HE-stained slice using the mosaic cell mass produced in Example 20-(1). FIG. 37 is an image of the HE-stained slice using the mosaic cell mass produced in Example 20-(2). FIG. 38 is an image of the HE-stained slice using the mosaic cell mass produced in Example 20-(3). As is evident from all the images, blood vessels were formed within the mosaic cell mass at the 5th day after transplantation. The formation of blood vessels in larger amounts was seen in the mosaic cell mass A produced in Example 20-(2), the mosaic cell mass produced in Example 20-(3), and the mosaic cell mass produced in Example 20-(1) in this order, demonstrating that in vivo cell survival in the central portion of the mosaic cell mass was evidently more favorable than that of the cell mass. It was also demonstrated that: the mosaic cell mass was able to form blood vessels therewithin; and the ability to form blood vessels was rendered higher by particularly allowing hECFCs to exist therewithin.

Example 22-(2)

In vivo Blood Vessel Formation Difference Evaluation Test in Mice Using Mosaic Cell Mass of hMSCs and hECFCs Transplantation of Mosaic Cell Mass Four-week-old male NOD/SCID mice (Charles River Laboratories Japan, Inc.) were used. The abdominal hair of each mouse was removed under anesthesia. The upper abdominal region was subcutaneously slit up, and scissors were inserted through the slit to take off the skin from the muscle. Then, each of 2 patterns of hMSC+hECFC mosaic cell masses (A and B) prepared in Examples 20(2) and 2 patterns of hMSC+hECFC cell masses (A and B) of Comparative Example 2 was scooped with tweezers and subcutaneously transplanted in the later abdominal region 1.5 cm below the slit, and the slit in the skin was sutured.

Collection of Mosaic Cell Mass

Anatomy was performed 6 days, 14 days, and 28 days after transplantation. The skin in the abdominal region was taken off, and the skin to which each mosaic cell mass was attached was cut into a square of approximately 1 cm² in size. In the case where the mosaic cell mass was also attached to the muscle in the abdominal region, the mosaic cell mass was collected together with the muscle.

A tissue slice was prepared for the skin slice to which the mosaic cell mass was attached and the mosaic cell masses before transplantation. The skin was dipped in 4% paraformaldehyde, and formalin fixation was performed. Then, the resulting product was embedded in paraffin to prepare a tissue slice of the skin containing each mosaic cell mass. The slice was stained with HE (hematoxylin-eosin) and immunostained with an anti-CD31 antibody for hECFC staining using a DAB color development method to analyze blood vessel formation and the states of hMSC and hECFC behaviors within the mosaic cell mass. An image of the HE-stained slice at the 14th day after transplantation is shown.

FIG. 39 is an image of the HE-stained slice using the mosaic cell mass A of Example 20-(2). FIG. 40 is an image of the HE-stained slice using the mosaic cell mass B of Example 20-(2). As is evident from all the images, blood vessels were formed within the mosaic cell mass at the 14th day after transplantation. The formation of blood vessels in larger amounts was seen in the mosaic cell mass B of Example 20-(2) than the mosaic cell mass A of Example 20-(2). It was demonstrated that the ability to form blood vessels was rendered higher by allowing hECFCs to exist within the mosaic cell mass and further increasing the number of hECFCs. On the other hand, FIG. 41 is an image of the HE-stained slice using the cell mass B of Comparative Example 2. The cell mass A of Comparative Example 2 failed to be collected at the 14th day after transplantation. By contrast, the cell mass B of Comparative Example 2 became small, and no blood vessel was seen therein while cell death was also observed. It could thereby be confirmed that the cell mass without the blocks failed to form blood vessels and exhibited cell death even though it contained hECFCs.

The invention claimed is:

1. A cell construct for cell transplantation, which comprises polymer blocks of biodegradable material and cells, wherein said cells comprise two or more types of cells, said cells comprise both non-vascular cells and vascular cells, and said cells are selected from the group consisting of pluripotent cells, somatic stem cells, precursor cells, and mature cells, wherein the plural polymer blocks are arranged in spaces between the plural cells, wherein the polymer blocks each have a size from 1 μm to 700 μm, and wherein the cells are isolated cells which were grown in vitro, wherein said cell construct has a region in which the volume of the vascular cells in the central portion of the cell construct is larger than the volume of the vascular cells in the peripheral portion, wherein said central portion of the cell construct refers to a volume corresponding to a distance 80% from the center of mass in distance from the center of mass to the surface of the cell construct, and wherein said peripheral portion of the cell construct refers to a volume from the position of 80% from the center to the surface of the construct, and wherein the number of vascular cells in the central portion is 60% to 100% to the total vascular cells in the implant.

2. The cell construct for cell transplantation according to claim 1, wherein the biodegradable material is polypeptide, polylactic acid, polyglycolic acid, PLGA, hyaluronic acid, glycosaminoglycan, proteoglycan, chondroitin, cellulose, agarose, carboxymethylcellulose, chitin, or chitosan.

3. The cell construct for cell transplantation according to claim 1, wherein the biodegradable material is a recombinant peptide.

4. The cell construct for cell transplantation according to claim 1, wherein the biodegradable material has two or more cell adhesion signals in a molecule.

5. The cell construct for cell transplantation according to claim 3, wherein the recombinant peptide is represented by the formula:

$$A\text{-}[(Gly\text{-}X\text{-}Y)_n]_m\text{-}B$$

wherein A represents any amino acid or amino acid sequence; B represents any amino acid or amino acid sequence; each X of total n independently represents any amino acid; each Y of total n independently represents any amino acid; n represents an integer of 3 to 100; m represents an integer of 2 to 10; and each Gly-X-Y of total n may be the same as or different from each other.

6. The cell construct for cell transplantation according to claim 3, wherein the recombinant peptide has (1) the amino acid sequence represented by SEQ ID NO: 1, or (2) an amino acid sequence having 80% or higher homology to the amino acid sequence represented by SEQ ID NO: 1 and having biodegradability.

7. The cell construct for cell transplantation according to claim 1, which further comprises an angiogenesis factor.

8. The cell construct for cell transplantation according to claim 1, which has a region wherein the density of the vascular cells in the central portion is $1.0 \times 10^{-4}$ cells/$\mu m^3$ or more.

9. A cell construct for cell transplantation in which blood vessels have been formed by using a cell construct for cell transplantation according to claim 1.

10. The cell construct for cell transplantation according to claim 1, wherein the polymer blocks each have a size from 10 µm to 300 µm.

11. A cell aggregate for cell transplantation which comprises non-vascular cells and vascular cells, wherein said cell aggregate satisfies at least one of the following requirements (1) and (2):

(1) the cell aggregate has a region wherein the volume of the vascular cells in the central portion of the cell aggregate is larger than the volume of the vascular cells in the peripheral portion; and (2) the cell aggregate has a region wherein the density of the vascular cells in the central portion is $1.0 \times 10^{-4}$ cells/$\mu m^3$ or more, wherein said central portion of the cell construct refers to a volume corresponding to a distance 80% from the center of mass in distance from the center to the surface of the cell construct, and wherein said peripheral portion of the cell construct refers to a volume from the position of 80% from the center of mass to the surface of the construct, and wherein the number of vascular cells in the central portion is 60% to 100% of the total vascular cells in the implant.

12. The cell aggregate for cell transplantation according to claim 11, wherein the cell aggregate satisfies both of the requirement (1) and (2).

* * * * *

SEQUENCE LISTING

```
<160> NUMBER OF SEQ ID NOS: 10

<210> SEQ ID NO 1
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 1
```

-continued

```
Gly Ala Pro Gly Ala Pro Gly Leu Gln Gly Ala Pro Gly Leu Gln Gly
 1               5                  10                  15
Met Pro Gly Glu Arg Gly Ala Ala Gly Leu Pro Gly Pro Lys Gly Glu
             20                  25                  30
Arg Gly Asp Ala Gly Pro Lys Gly Ala Asp Gly Ala Pro Gly Ala Pro
         35                  40                  45
Gly Leu Gln Gly Met Pro Gly Glu Arg Gly Ala Ala Gly Leu Pro Gly
     50                  55                  60
Pro Lys Gly Glu Arg Gly Asp Ala Gly Pro Lys Gly Ala Asp Gly Ala
 65                  70                  75                  80
Pro Gly Lys Asp Gly Val Arg Gly Leu Ala Gly Pro Ile Gly Pro Pro
                 85                  90                  95
Gly Glu Arg Gly Ala Ala Gly Leu Pro Gly Pro Lys Gly Glu Arg Gly
             100                 105                 110
Asp Ala Gly Pro Lys Gly Ala Asp Gly Ala Pro Gly Lys Asp Gly Val
         115                 120                 125
Arg Gly Leu Ala Gly Pro Ile Gly Pro Pro Gly Pro Ala Gly Ala Pro
     130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Ala Gly Pro Lys Gly Ala
                 165                 170                 175
Asp Gly Ala Pro Gly Lys Asp Gly Val Arg Gly Leu Ala Gly Pro Pro
             180                 185                 190
Gly Ala Pro Gly Leu Gln Gly Ala Pro Gly Leu Gln Gly Met Pro Gly
         195                 200                 205
Glu Arg Gly Ala Ala Gly Leu Pro Gly Pro Lys Gly Glu Arg Gly Asp
     210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
                 245                 250                 255
Glu Arg Gly Asp Ala Gly Pro Lys Gly Ala Asp Gly Ala Pro Gly Lys
             260                 265                 270
Asp Gly Val Arg Gly Leu Ala Gly Pro Ile Gly Pro Pro Gly Glu Arg
         275                 280                 285
Gly Ala Ala Gly Leu Pro Gly Pro Lys Gly Glu Arg Gly Asp Ala Gly
     290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                 325                 330                 335
Gly Leu Gln Gly Met Pro Gly Glu Arg Gly Ala Ala Gly Leu Pro Gly
             340                 345                 350
Pro Lys Gly Glu Arg Gly Asp Ala Gly Pro Lys Gly Ala Asp Gly Ala
         355                 360                 365
Pro Gly Lys Asp Gly Val Arg Gly Leu Ala Gly Pro Pro Gly Ala Pro
     370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                 405                 410                 415
Lys Gly Ala Asp Gly Ala Pro Gly Ala Pro Gly Leu Gln Gly Met Pro
```

```
                    420                 425                 430
Gly Glu Arg Gly Ala Ala Gly Leu Pro Gly Pro Lys Gly Glu Arg Gly
                435                 440                 445
Asp Ala Gly Pro Lys Gly Ala Asp Gly Ala Pro Gly Lys Asp Gly Val
            450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
            515                 520                 525
Gly Met Pro Gly Glu Arg Gly Ala Ala Gly Leu Pro Gly Pro Lys Gly
                530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 5

Arg Tyr Val Val Leu Pro Arg
```

-continued

```
<210> SEQ ID NO 6
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Glu Arg Gly Asp
1
```